United States Patent
Dragovich et al.

(10) Patent No.: US 6,531,452 B1
(45) Date of Patent: Mar. 11, 2003

(54) ANTIPICORNAVIRAL COMPOUNDS AND COMPOSITIONS, THEIR PHARMACEUTICAL USES, AND MATERIALS FOR THEIR SYNTHESIS

(75) Inventors: Peter Scott Dragovich, Encinitas, CA (US); Stephen Evan Webber, San Diego, CA (US); Thomas Jay Prins, Cardiff, CA (US); Ru Zhou, Carlsbad, CA (US); Joseph Timothy Marakovits, Encinitas, CA (US); Theodore O. Johnson, Jr., San Diego, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/301,977

(22) Filed: Apr. 29, 1999

Related U.S. Application Data

(63) Continuation of application No. PCT/US99/00260, filed on Jan. 5, 1999.
(60) Provisional application No. 60/098,358, filed on Aug. 28, 1998, and provisional application No. 60/083,828, filed on Apr. 30, 1998.

(51) Int. Cl.$^7$ ................................................. C07K 5/06

(52) U.S. Cl. ......................... 514/19; 514/351; 514/378; 514/423; 546/329; 548/248

(58) Field of Search ........................ 514/19, 351, 378, 514/423; 560/19; 546/329; 548/248

(56) References Cited

U.S. PATENT DOCUMENTS 5,856,530 A   1/1999   Webber et al. ............... 549/478

FOREIGN PATENT DOCUMENTS

| WO | WO9523222 | 8/1995 |
| WO | WO9531433 | 11/1995 |
| WO | WO9743305 | 11/1997 |
| WO | WO9843950 | 10/1998 |
| WO | WO9931122 | 6/1999 |

OTHER PUBLICATIONS

Turner, Annals of Allergy, Asthma, and Immunology 78, 531, 1997.*
Ikuta et al., "Synthesis and Antiinflammatory Activities of 3–(3,5–Di–tert–butyl–4–hydroxybenzylidene) pyrrolidin–2–ones", *J. Med. Chem*, vol. 30 (1987) p. 1995–1998.
Jackson et al., "Preparation of Enantiomerically Pure Protected 4–Oxo–α–amino Acids and 3–Aryl–α amino Acids from Serine", *J. Org. Chem.*, vol. 57 (1992) p. 3397–3404.
Baldwin, "Diarylmethylene–Tetracyanoethylene Cycloadditions", *J. Org. Chem.*, vol. 36 (1971) p. 1441–1443.
Bischofberger et al., "Sythesis of Analogues of 1,3–Dihydroxyacetone Phosphate and Glyceraldehyde 3–Phosphate for Use in Studies of Fructose–1,6–diphosphate Aldolase", *J. Org. Chem.*, vol. 53 (1988) p. 3457–3465.
Weislow et al., "New Soluble–Formazan Assay for HIV–1 Cytopathic Effects: Application to High–Flux Screening of Synthetic and Natural Products for IDS–Antiviral Activity", *J. Natl. Cancer Inst.*, vol. 81, No. 8 (1989) pp. 577–586.
Hoffman et al., "Preparation of (R)–2–Azidoesters from 2–((p–Nitrobenzene) sulfonyl)oxy Esters and Their Use as Protected Amino Acid Equivalents for the Synthesis of Di– and Tripeptides Containing D–Amino Acid Constituents", *Tetrahedron*, vol. 48 (1992) p. 3007–3020.
Birch et al., "Purification of Recombinant Human Rhinovirus 14 3C Protease Expressed in *Escherichia coli*", *Protein Expression and Purification*, 6, 609–618 (1995).
Kaldor et al., "Glutamine–Drived Aldehydes For The Inhibition Of Human Rhinovirus 3C Protease", *Bioorganic & Medicinal Chemistry Letters*, 5(17), 2021–2026 (1995).
Kong et al., "Synthesis and Evaluation of Peptidyl Michael Acceptors That Inactivate Human Rhinovirus 3C Protease and Inhibit Virus Replication", *J. Med. Chem.*, 41, 2579–2587 (1998).
Murray et al., "The Enantiospecific Synthesis Of Novel Lysine Analogues Incorporating a Pyrrolidine Containing Side Chain", *Tetrahedron Letters*, 39, 6721–6724 (1998).
Webber et al., "Design, Synthesis, and Evaluation of Nonpeptidic Inhibitors of Human Rhinovirus 3C Protease", *J. Med. Chem.*, 39, 5072–5082 (1996).
Webber et al., "Tripeptide Aldehyde Inhibitors of Human Rhinovirus 3C Protease: Design, Synthesis, Biological Evaluation, and Cocrystal Structure Solution of $P_1$ Glutamine Isosteric Replacements", *J. Med. Chem.*, 41, 2786–2805 (1998).

(List continued on next page.)

*Primary Examiner*—Christopher S. F. Low
*Assistant Examiner*—David Lukton
(74) *Attorney, Agent, or Firm*—Peter Richardson; Gregg C. Benson; Karl Neidert

(57) ABSTRACT

Peptido and peptidomimetic compounds of the formula:

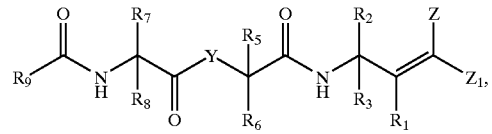

wherein the formula variables are as defined in the disclosure, advantageously inhibit or block the biological activity of the picornaviral 3C protease. These compounds, as well as pharmaceutical compositions containing these compounds, are useful for treating patients or hosts infected with one or more picornaviruses, such as RVP. Intermediates and synthetic methods for preparing such compounds are also provided.

50 Claims, No Drawings

OTHER PUBLICATIONS

Askin et al., "Highly Diastereoselective Alkylations of Chiral Amide Enolates: New Routes to Hydroxyethylene Dipeptide Isostere Inhibitors of HIV–1 Protease", *J. Org. Chem.*, 57, 2771–2773 (1992).

Bradbury et al., "1,2,4–Triazolo[4,3–a]pyrazine Derivatives with Human Renin Inhibitory Activity. 2. Synthesis, Biological Properties and Molecular Modeling of Hydroxyethylene Isostere Derivatives", *J. Med. Chem.*, 33, 2335–2342 (1990).

Bradbury et al., "An Efficient Synthesis of the γ–Latone Corresponding to a Hydroxyethylene Dipeptide Isostere Using Stereoelective Bromolactonisation of a Chiral Acyloxazolidinone", *Tetrahedron Letters*, 30, 3845–3848 (1989).

Chida et al., "Total Synthesis and Absolute Configuration of Bengamide A", *J. Chem. Soc. Commun.*, 1064–1066 (1992).

Diana et al., "Picornavirus Inhibitors: Trifluoromethyl Substitution Provides a Global Protective Effect against Hepatic Metabolism", *J. Med. Chem.*, 38, 1355–1371 (1995).

Dondoni et al., Thiazole–Based Stereoselective Routes to Leucine and Phenylalanine Hydroxyethylene Dipeptide Isostere Inhibitors of Renin and HIV–1 Aspartic Protease†, *J. Org. Chem.*, 60, 7927–7933 (1995).

Herold et al., "A Versatile and Stereocontrolled Synthesis of Hydroxyethylene Dipeptide Isosteres", *J. Org. Chem.*, 54, 1178–1185 (1989).

Hoffman et al., "A Simple Stereoselective Synthesis of Ketomethylene Dipeptide Isosteres" (Department of Chemistry and Biochemistry, New Mexico State University), Tetrahedron, 53, 7119–7126 (1997).

Jones et al., "A Short Stereocontrolled Synthesis of Hydroxyethylene Dipeptide Isosteres", *J. Org. Chem.*, 58, 2286–2290 (1993).

Liu et al., "Structure–Activity Relationships for Inhibition of Papain by Peptide Michael Acceptors", *J. Med. Chem.*, 35, 1067–1075 (1992).

Luly et al., "A Synthesis of Protected Aminoalkyl Epoxides from α–Amino Acids", *J. Org. Chem.*, 52, 1487–1492 (1987).

McWilliams et al., "Tandem Asymmetric Transformations: An Asymmetric 1,2–Migration from a Higher Order Zincate Coupled with a Stereoslective Homoaldol Reaction", *J. Am. Chem. Soc.*, 118, 11970–11971 (1996).

Palmer et al., "Vinyl Sulfones as Mechanism–Based Cysteine Protease Inhibitors", *J. Med. Chem.*, 38, 3193–3196 (1995).

Pegorier et al., "A General Stereocontrolled Synthesis of Hydroxethylene Dipeptide Isosteres", *Tetrahedron Letters*, 36, 2753–2756 (1995).

Thompson et al., "Carboxyl–Modified Amino Acids and Peptides as Protease Inhibitors", *J. Med. Chem.*, 29, 104–111 (1986).

Wuts et al., "Synthesis of the Hydroxyethylene Isostere of Leu–Val", *J. Org. Chem.*, 57, 6696–6700 (1992).

Hanzlik et al., "Communications to the Editor", *Journal of Medicinal Chemistry*, 27(6), 711–712 (1984).

Venkatraman et al., "Synthesis of Potential Inhibitors for Human Rhinovirus 3C Protease", The Second Winter Conference on Medicinal and Bioorganic Chemistry, Jan. 26–31, 1997, Steamboat Springs, Colorado.

Palmer et al., "Mechanism–Based Cysteine Protease Inhibitors", Paper #68, 210$^{th}$ Meeting of the American Chemical Society, Aug. 20–24, 1995, Chicago, Illinois.

* cited by examiner

SEQUENCE LISTING

<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: A forced amino acid consensus sequence of the rhinovirus 3C protease cleavage site wherein certain amino acids have been substituted.

<400> SEQUENCE: 1

Gly Arg Ala Val Phe Gln Gly Pro Val Gly
1               5                   10

ANTIPICORNAVIRAL COMPOUNDS AND COMPOSITIONS, THEIR PHARMACEUTICAL USES, AND MATERIALS FOR THEIR SYNTHESIS

This application claims benefit of U.S. Provisional Application No. 60/098,358, filed Aug. 28, 1998, and U.S. Provisional Application No. 60/083,828, filed Apr. 30, 1998, which is a continuation of PCT/US99/00260 filed Jan. 5, 1999.

FIELD AND INDUSTRIAL APPLICABILITY OF THE INVENTION

The invention pertains to peptide-like and peptidomimetic compounds that advantageously inhibit the enzymatic activity of picornaviral 3C proteases, especially rhinovirus 3C proteases (RVPs), and that retard viral growth in cell culture. The invention also relates to the use of such compounds in pharmaceutical compositions and therapeutic treatments for rhinoviral infections. The invention further relates to processes for synthesizing such compounds and compounds useful in such syntheses.

BACKGROUND OF THE INVENTION

The picornaviruses are a family of tiny non-enveloped positive-stranded RNA-containing viruses that infect humans and other animals. These viruses include the human rhinoviruses, human polioviruses, human coxsackieviruses, human echoviruses, human and bovine enteroviruses, encephalomyocarditis viruses, meningitis virus, foot and mouth viruses, hepatitis A virus, and others. The human rhinoviruses are a major cause of the common cold. To date, there are no effective therapies on the market that cure the common cold, only treatments that relieve the symptoms.

Picornaviral infections may be treated by inhibiting the proteolytic 3C enzymes. These enzymes are required for the natural maturation of the picornaviruses. They are responsible for the autocatalytic cleavage of the genomic, large polyprotein into the essential viral proteins. Members of the 3C protease family are cysteine proteases, where the sulfhydryl group most often cleaves the glutamine-glycine amide bond. Inhibition of 3C proteases is believed to block proteolytic cleavage of the polyprotein, which in turn can retard the maturation and replication of the viruses by interfering with viral particle production. Therefore, inhibiting the processing of this cysteine protease with selective small molecules that are specifically recognized should represent an important and useful approach to treat and cure viral infections of this nature and, in particular, the common cold.

Some small-molecule inhibitors of the enzymatic activity of picornaviral 3C proteases (i.e., antipicornaviral compounds) have been recently discovered. See, for example: U.S. patent application Ser. No. 08/850,398, filed May 2, 1997, now U.S. Pat. No. 5,856,530 by Webber et al.; U.S. patent application Ser. No. 08/991,282, filed Dec. 16, 1997, U.S. Pat. No. 6,020,371 by Dragovich et al.; and U.S. patent application Ser. No. 08/991,739, filed Dec. 16, 1997, U.S. Pat. No. 5,962,487 by Webber et al. These U.S. patent applications, the disclosures of which are incorporated herein by reference, describe certain antipicornaviral compounds. There is still a desire to discover small-molecule compounds that are especially potent antipicornaviral agents.

SUMMARY OF THE INVENTION

Thus, an object of this invention is to discover small-molecule compounds that are especially potent antipicornaviral agents. A further object of the invention is to provide intermediates useful for the synthesis of said protease-inhibiting compounds and synthetic methods useful for such syntheses. A yet further object of the invention is to achieve pharmaceutical compositions that are highly effective for treating maladies mediated by inhibition of picornaviral 3C proteases, such as the common cold.

Such objects have been attained through the discovery of compounds of the invention, which are picornaviral 3C protease inhibitors displaying particularly strong antiviral activity. It has surprisingly been discovered that peptido and peptidomimetic compounds containing a five-membered heterocyclic group have high rhinoviral-protease-inhibiting activity. It has further been surprisingly found that the rhinoviral-protease-inhibiting activity of peptido and peptidomimetic compounds may be significantly enhanced by replacing a glutamine-like moiety found in some known rhinoviral-protease-inhibiting compounds with a side-chain comprising a gamma- or delta-lactam.

The inhibitors of the present invention are of the following general formula (I):

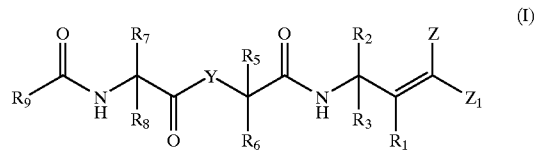

wherein:

Y is —N($R_y$)—, —C($R_y$)($R_y$)—, or —O—, where each $R_y$ is independently —H or lower alkyl;

$R_1$ is —H, —F, -alkyl, —OH, —SH, or an O-alkyl group;

$R_2$ and $R_3$ are each independently H;

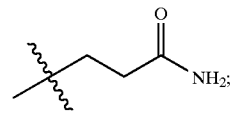

or

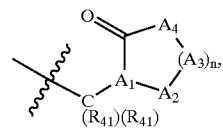

where n is an integer from 0 to 5, $A_1$ is CH or N, $A_2$ and each $A_3$ are independently selected from C($R_{41}$)($R_{41}$), N$R_{41}$), S, S(O), S(O)$_2$, and O, and $A_4$ is NH or N$R_{41}$, where each $R_{41}$ is independently H or lower alkyl, provided that no more than two heteroatoms occur consecutively in the above-depicted ring formed by $A_1$, $A_2$, ($A_3$)$_n$, $A_4$ and C=O, and at least one of $R_2$ and $R_3$ is

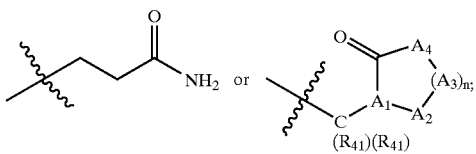

R₅ and R₆ are each independently H, F, an alkyl group, a cycloalkyl group, a heterocycloalkyl group, an aryl group, or a heteroaryl group;

R₇ and R₈ are each independently H, an alkyl group, a cycloalkyl group, a heterocycloalkyl group, an aryl group, a heteroaryl group, —OR₁₇, —SR₁₇, —NR₁₇R₁₈, —NR₁₉NR₁₇R₁₈, or —NR₁₇OR₁₈, where R₁₇, R₁₈, and R₁₉ are each independently H, an alkyl group, a cycloalkyl group, a heterocycloalkyl group, an aryl group, a heteroaryl group, or an acyl group, provided that at least one of R₇ and R₈ is an alkyl group, a cycloalkyl group, a heterocycloalkyl group, an aryl group, a heteroaryl group, —OR₁₇, —SR₁₇, —NR₁₇R₁₈, —NR₁₉NR₁₇R₁₈, or —NR₁₇OR₁₈;

R₉ is a suitable organic moiety; and

Z and Z₁ are each independently H, F, an alkyl group, a cycloalkyl group, a heterocycloalkyl group, an aryl group, a heteroaryl group, —C(O)R₂₁, —CO₂R₂₁, —CN, —C(O)NR₂₁R₂₂, —C(O)NR₂₁OR₂₂, —C(S)R₂₁, —C(S)NR₂₁R₂₂, —NO₂, —SOR₂₁, —SO₂R₂₁, —SO₂NR₂₁R₂₂, —SO(NR₂₁)(OR₂₂), —SONR₂₁, —SO₃R₂₁, —PO(OR₂₁)₂, —PO(R₂₁)(R₂₂), —PO(NR₂₁R₂₂)(OR₂₃), —PO(NR₂₁R₂₂)(NR₂₃R₂₄), —C(O)NR₂₁NR₂₂R₂₃, or —C(S)NR₂₁NR₂₂R₂₃, where R₂₁, R₂₂, R₂₃, and R₂₄ are each independently H, an alkyl group, a cycloalkyl group, a heterocycloalkyl group, an aryl group, a heteroaryl group, an acyl group, or a thioacyl group, or where any two of R₂₁, R₂₂, R₂₃, and R₂₄, together with the atom(s) to which they are bonded, form a heterocycloalkyl group, provided that Z and Z₁ are not both H;

or Z₁ and R₁, together with the atoms to which they are bonded, form a cycloalkyl or heterocycloalkyl group, where Z₁ and R₁ are as defined above except for moieties that cannot form the cycloalkyl or heterocycloalkyl group;

or Z and Z₁, together with the atoms to which they are bonded, form a cycloalkyl or heterocycloalkyl group, where Z and Z₁ are as defined above except for moieties that cannot form the cycloalkyl or heterocycloalkyl group.

The invention also pertains to prodrugs, pharmaceutically acceptable salts, pharmaceutically active metabolites, and pharmaceutically acceptable solvates of compounds of the formula I.

In preferred embodiments of the compounds of the formula I, R₂ and R₃ are each independently H;

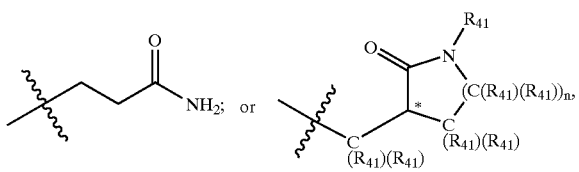

where n is an integer from 0 to 5, each R₄₁ is independently H or lower alkyl, and the stereochemistry at the carbon denoted with an asterisk may be R or S; provided that at least one of R₂ and R₃ is

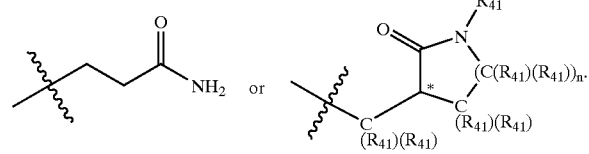

Preferably, R₉ is a five-membered heterocycle having one to three heteroatoms selected from O, N, and S. Alternatively, R₉ is

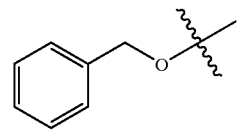

where R₂ is

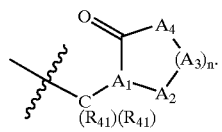

In other preferred embodiments, the variables of formula I are as follows. Z and Z₁ are each independently selected from H, F, lower alkyl, —CO₂R₂₁, and —C(O)NR₂₁R₂₂, provided that Z and Z₁ are not both H, where R₂₁ and R₂₂ are each independently H, an alkyl group, a cycloalkyl group, a heterocycloalkyl group, an aryl group, a heteroaryl group, an acyl group, or a thioacyl group, or R₂₁ and R₂₂, together with the atom(s) to which they are bonded, form a heterocycloalkyl group. At least one of R₂ or R₃ is

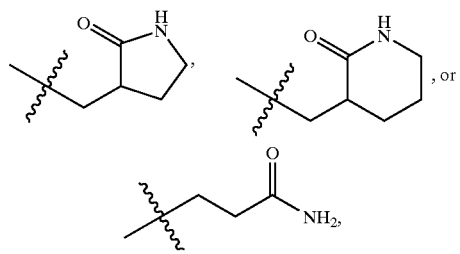

and the other is H. R₅ and R₆ are each independently selected from H, F, an alkyl group, a cycloalkyl group, a heterocycloalkyl group, an aryl group, and a heteroaryl group, more preferably one of R₅ and R₆ is H and the other is alkyl or aryl (e.g., unsubstituted or substituted phenylmethyl). R₇ and R₈ are each independently H, an alkyl group, a cycloalkyl group, a heterocycloalkyl group, an aryl group, or a heteroaryl group; and more preferably one of R₇ and R₈ is H and the other is alkyl (e.g., 2-propyl, 2-methyl-2-propyl, or 2-methyl-1-propyl) or arylmethyl (e.g., unsubstituted or substituted phenylmethyl or naphthylmethyl). R₉ is a five-membered heterocycle having from one to three heteroatoms selected from O, N, and S, more preferably a five-membered heterocycle having at least one nitrogen heteroatom and at least one oxygen heteroatom (e.g., unsubstituted or substituted 1,2-oxazolyl (i.e., isoxazolyl), 1,3-oxazolyl (i.e., oxazolyl), or oxadiazolyl (1,2,3-oxadiazolyl, 1,2,4-oxadiazolyl, or 1,2,5-oxadiazolyl). When $R_9$ is oxadiazolyl, unsubstituted and monomethyl-substituted 1,2,4-oxadiazolyl are preferred. In especially preferred embodiments, $R_9$ is 3-isoxazolyl or 5-isoxazolyl, either unsubstituted or substituted with one or two methyl groups and/or halogens, with chlorine and fluorine being preferred halogen substituents.

In a preferred embodiment, the compounds, prodrugs, pharmaceutically acceptable salts, pharmaceutically active metabolites, and solvates have an antipicornaviral activity with an $EC_{50}$ less than or equal to 100 $\mu$M in the H1-HeLa cell culture assay, and more preferably an antirhinoviral activity with an $EC_{50}$ less than or equal to 10 $\mu$M in the H1-HeLa cell culture.

In another aspect, the invention is directed to intermediates of formula II, preferably of the formula II', which are useful in the synthesis of certain compounds:

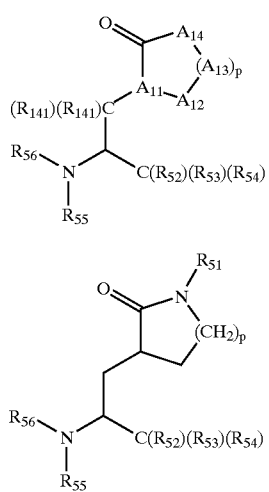

wherein:
p is an integer of from 0 to 5;
$A_{11}$ is CH or N, $A_{12}$ and each $A_{13}$ are independently selected from $C(R_{61})(R_{61})$, $N(R_{61})$, S, S(O), S(O)$_2$, and O, and $A_{14}$ is NH or $NR_{61}$, where each $R_{61}$ is independently H, alkyl, acyl, or aryl, provided that no more than two heteroatoms occur consecutively in the above-depicted ring in formula II formed by $A_{11}$, $A_{12}$, $(A_{13})_n$, $A_{14}$ and C=O;
each $R_{141}$ is independently H or lower alkyl;
$R_5$, is H, alkyl, acyl, or aryl;
$R_{52}$, $R_{53}$, and $R_{54}$ are each independently selected from H, hydroxyl, alkyl, acyl, and aryl; or any two of $R_{52}$, $R_{53}$, and $R_{54}$ together form =O or =$C(R_{57})(R_{58})$, where $R_{57}$ and $R_{58}$ are each independently selected from H, alkyl, $CO_2(C_1-C_6)$alkyl, $C(O)N(C_1-C_6)$alkyl, and $CO_2$(aryl); and
$R_{55}$ and $R_{56}$ are each independently H or a suitable protecting group for nitrogen.

The invention is also directed to pharmaceutically acceptable salts of the compounds of formulae II and II'.

The invention also relates to pharmaceutical compositions containing a therapeutically effective amount of at least one compound of the formula I, or a prodrug, pharmaceutically acceptable salt, pharmaceutically active metabolite, or solvate thereof. Additionally, the invention relates to methods of inhibiting picornaviral 3C protease by administering a therapeutically effective amount of at least one compound of the formula I, or a prodrug, pharmaceutically acceptable salt, pharmaceutically active metabolite, or solvate thereof.

DETAILED DESCRIPTION AND PREFERRED EMBODIMENTS

The present invention relates to compounds of the formula I:

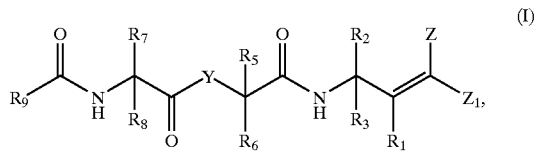

wherein Y, $R_1$, $R_2$, $R_3$, $R_5$, $R_6$, $R_7$, $R_8$, $R_9$, Z, and $Z_1$ are as defined above, and to pharmaceutically acceptable salts, prodrugs, active metabolites, and solvates thereof. Preferably, such compounds, pharmaceutically acceptable salts, prodrugs, active metabolites, and solvates have antipicornaviral activity, more preferably antirhinoviral activity, corresponding to an $EC_{50}$ less than or equal to 100 $\mu$M in the H1-HeLa cell culture assay, more preferably corresponding to an $EC_{50}$ less than or equal to 10 $\mu$M in the H1-HeLa cell culture assay.

The present invention additionally relates to preferred compounds of the formulas I-A, I-B, and I-C:

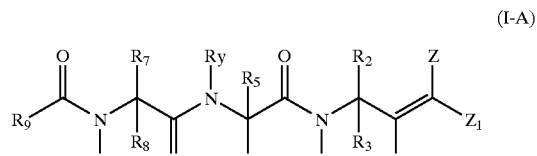

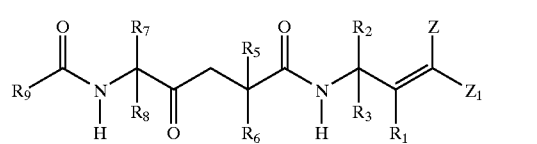

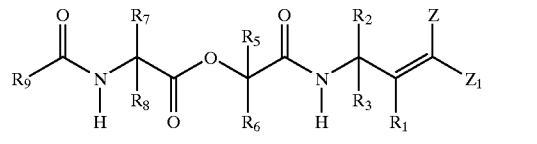

wherein $R_y$ (in formula I-A) is H or lower alkyl, and $R_1$, $R_2$, $R_3$, $R_5$, $R_6$, $R_7$, $R_8$, $R_9$, Z, and $Z_1$ are as defined above, and to pharmaceutically acceptable salts, prodrugs, active metabolites, and solvates thereof.

The inventive compounds of formulas I-A, which are referred to herein as "peptide-like" compounds, I-B, which are referred to herein as "ketomethylene-type" compounds, and I-C, which are referred to herein as "depsipeptide" compounds, differ in their backbones, which may affect the specific biodistribution or other physical properties; nonetheless each possesses a strong rhinoviral-protease-inhibiting activity.

In preferred embodiments of compounds of formulas I-A, I-B, and I-C above:
$R_1$ is H, F, or an alkyl group;
$R_y$ (in formula I-A) is H or methyl;
$R_3$, $R_5$, and $R_8$ are each H;

$R_2$ is selected from one of the following moieties:

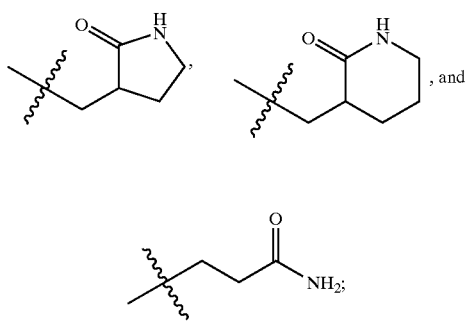

$R_6$ is an alkyl group, which has as a preferred optional substituent an aryl group;

$R_7$ is an alkyl group, a cycloalkyl group, a heterocycloalkyl group, an aryl group, or a heteroaryl group;

$R_9$ is a five-membered heterocycle having from one to three heteroatoms selected from O, N, and S, preferably where at least one of the heteroatoms is nitrogen, that is unsubstituted or substituted, where the optional substituents are preferably halogen or lower alkyl, and more preferably mono-chloro or -fluoro or a methyl group; and Z and $Z_1$ are each independently H, F, an alkyl group, a cycloalkyl group, a heterocycloalkyl group, an aryl group, a heteroaryl group, —C(O)$R_{21}$, —CO$_2R_{21}$, —CN, —C(O)NR$_{21}R_{22}$, —C(O)NR$_{21}$OR$_{22}$, —C(S)$R_{21}$, —C(S)NR$_{21}R_{22}$, —NO$_2$, —SOR$_{21}$, —SO$_2R_{21}$, —SO$_2$NR$_{21}R_{22}$, —SO(NR$_{21}$)(OR$_{22}$), —SONR$_{21}$, —SO$_3R_{21}$, —PO(OR$_{21}$)$_2$, —PO(R$_{21}$)(R$_{22}$), —PO(NR$_{21}R_{22}$)(OR$_{23}$), —PO(NR$_{21}R_{22}$)(NR$_{23}R_{24}$), —C(O)NR$_{21}$NR$_{22}R_{23}$, or —C(S)NR$_{21}$NR$_{22}R_{23}$, where Z and $Z_1$ are not both H, and where $R_{21}$, $R_{22}$, $R_{23}$, and $R_{24}$ are each independently H, an alkyl group, a cycloalkyl group, a heterocycloalkyl group, an aryl group, a heteroaryl group, an acyl group, or a thioacyl group, or where any two of $R_{21}$, $R_{22}$, $R_{23}$, and $R_{24}$, together with the atom(s) to which they are bonded, form a heterocycloalkyl group, or Z and $Z_1$ (both as defined above), together with the atoms to which they are attached, form a heterocycloalkyl group.

In preferred embodiments, the compounds of the invention are of the formulae I-A', I-B', and I-C':

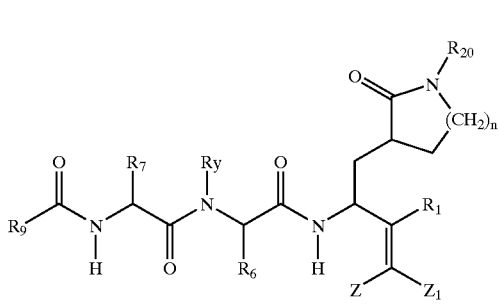

(I-A')

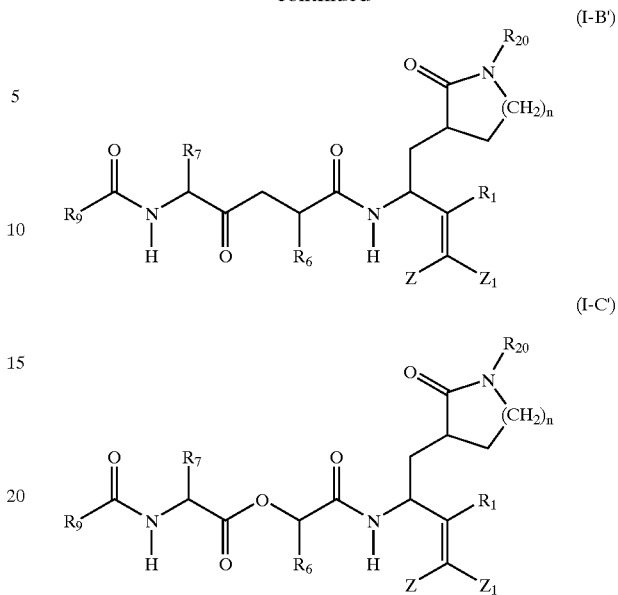

wherein:

$R_1$, Z, and $Z_1$ are as defined above;

n is 1 or 2;

$R_y$ (in formula I-A') is H or lower alkyl;

$R_6$ is alkyl, cycloalkyl, heterocycloalkyl, aryl, or heteroaryl;

$R_7$ is alkyl, cycloalkyl, heterocycloalkyl, aryl, heteroaryl, —OR$_{17}$, —SR$_{17}$, —NR$_{17}R_{18}$, —NR$_{19}$NR$_{17}R_{18}$, or —NR$_{17}$OR$_{18}$, where $R_{17}$, $R_{18}$, and $R_{19}$ are each independently H, alkyl, cycloalkyl, heterocycloalkyl, aryl, heteroaryl, or acyl;

$R_9$ is a five-membered heterocycle having one to three heteroatoms selected from O, N, and S, that is unsubstituted or substituted, where the optional substituents are preferably one or two lower alkyl groups and/or halogens; and $R_{20}$ is H.

The invention also relates to prodrugs, pharmaceutically acceptable salts, pharmaceutically active metabolites, and solvate of such compounds.

In preferred embodiments, the RVP-inhibiting agents of the invention are compounds of any of the stereospecific formulas I-A", I-B", and I-C":

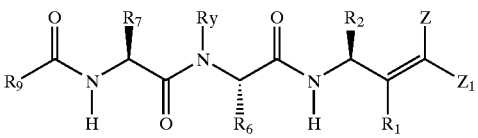

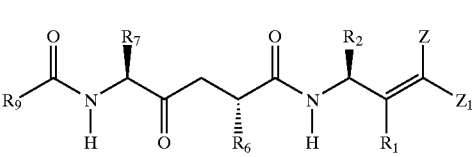

(I-C")

wherein $R_y$, $R_1$, $R_2$, $R_6$, $R_7$, $R_9$, Z, and $Z_1$ are as defined above, and pharmaceutically acceptable salts, prodrugs, active metabolites, and solvates thereof.

In preferred embodiments of compounds of the formula I-A", I-B", or I-C":

$R_1$ is H, F, or methyl;

$R_y$ (in formula I-A') is H or methyl;

$R_2$ is selected from one of the following moieties:

$R_6$ is arylmethyl or arylthiomethyl, where aryl is preferably an optionally substituted phenyl group;

$R_7$ is an alkyl group, more preferably selected from 2-propyl, 2-methyl-2-propyl, 2-methyl-1-propyl, and arylmethyl, where the aryl group is preferably phenyl or naphthyl;

$R_9$ is isoxazolyl, oxazolyl, or oxadiazolyl, optionally substituted with one or two lower alkyl groups and/or halogens; and Z is H, and $Z_1$ is —$CO_2R_{21}$, —CN, or —$C(O)NR_{21}R_{22}$, where $R_{21}$ and $R_{22}$ are as defined above, or Z and $Z_1$ together form a cyclic ester or amide.

Even more preferably, the RVP-inhibiting agents of the invention are compounds of any of the formulas I-A''', I-B''', and I-C''':

(I-A''')

(I-B''')

(I-C''')

wherein n, $R_y$, $R_1$, $R_{20}$, $R_6$, $R_7$, $R_9$, Z, and $Z_1$ are as defined above, and pharmaceutically acceptable salts, prodrugs, active metabolites, and solvates thereof.

In preferred compounds of the formula (I-A'''), (I-B'''), or (I-C'''):

$R_1$ is H, F, or methyl;

$R_y$ (in formula I-A') is H or methyl;

$R_{20}$ is hydrogen;

$R_6$ is arylmethyl or arylthiomethyl, where aryl is preferably phenyl unsubstituted or substituted with halogen, lower alkyl, and/or lower alkoxy;

$R_7$ is an alkyl group, and more preferably is selected from 2-propyl, 2-methyl-2-propyl, 2-methyl-1-propyl, and arylmethyl, where the aryl group is preferably phenyl or naphthyl;

$R_9$ is isoxazolyl, oxazolyl, or oxadiazolyl, each optionally substituted with one or two lower alkyl groups and/or halogens; and Z is H, and $Z_1$ is —$CO_2R_{21}$, —CN, or —$C(O)NR_{21}R_{22}$, where $R_{21}$ and $R_{22}$ are as defined above, or Z and $Z_1$ together form a cyclic ester or amide.

In especially preferred compounds of the invention of the generic formula I (and subgeneric formulae), $R_1$ is H or F.

In another aspect, the invention is directed to intermediate compounds of the formulas II and II':

(II)

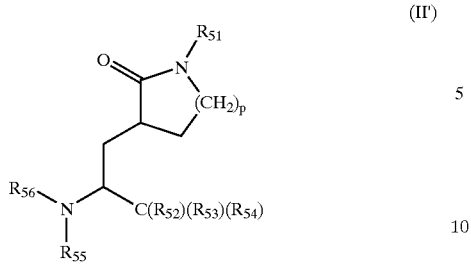

wherein the variables (p, $A_{11}$, $A_{12}$, $A_{13}$, $A_{14}$, $R_{51}$, $R_{52}$, $R_{53}$, $R_{54}$, $R_{55}$, $R_{56}$, and $R_{141}$) are as defined above. These compounds are useful for synthesizing pharmaceutically useful compounds of the formula I.

Preferred $R_{55}$ and $R_{56}$ groups are H and suitable protecting groups for nitrogen, for example, BOC (t-butyloxycarbonyl), CBZ (benzyloxycarbonyl), FMOC (fluorene-9-methyloxycarbonyl), other alkyloxycarbonyls (e.g. methyloxycarbonyl), and trityl (triphenylmethyl). Other suitable nitrogen-protecting groups may be readily selected by artisans (see, e.g., Greene and Wutz, *Protecting Groups in Chemical Synthesis* ($2^{nd}$ ed.), John Wiley & Sons, NY (1991)). Preferred groups for $R_{52}$, $R_{53}$, and $R_{54}$ are H, alkoxy, hydroxy, and carbonyl.

Preferred formula-II compounds include the following, where $P_N$ is a suitable protecting group for nitrogen and q is 1 or 2:

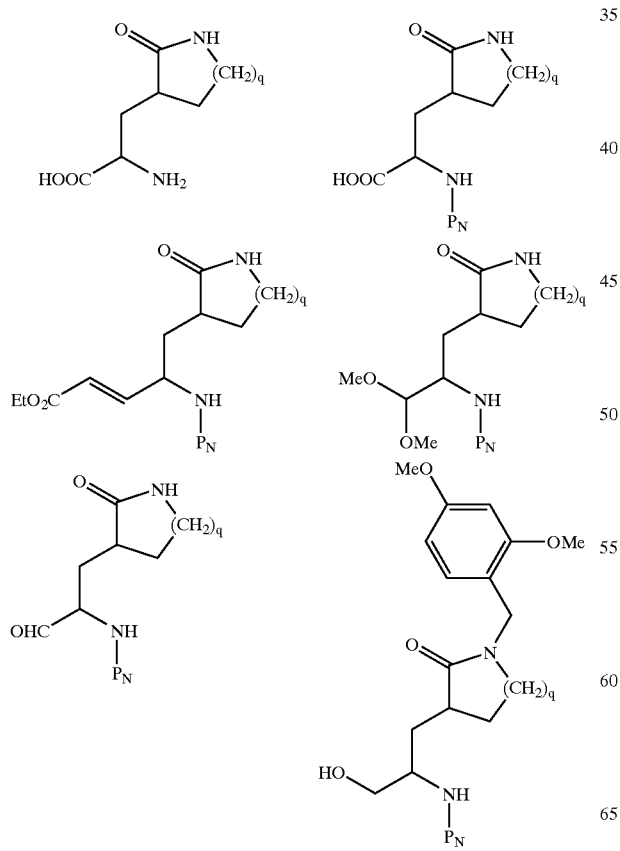

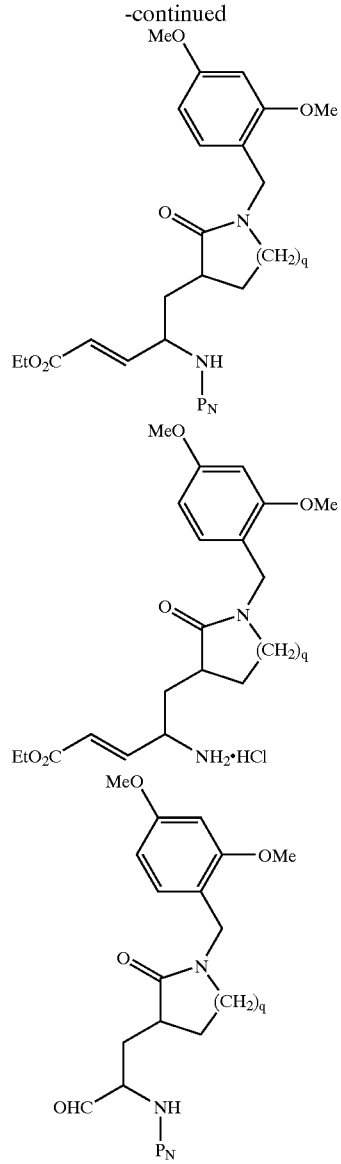

Other preferred intermediates include the following compounds, where BOC is t-butyloxycarbonyl:

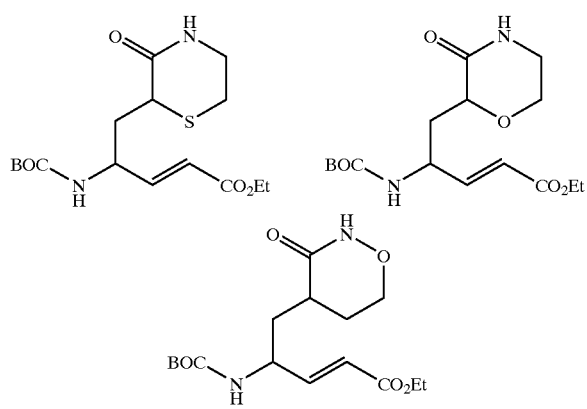

Of these, the preferred stereoisomers are:

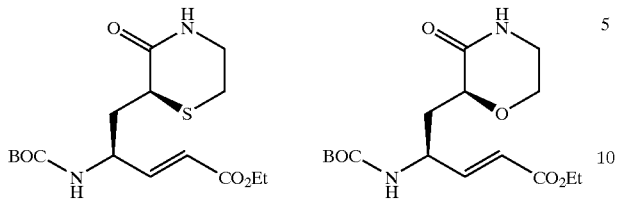

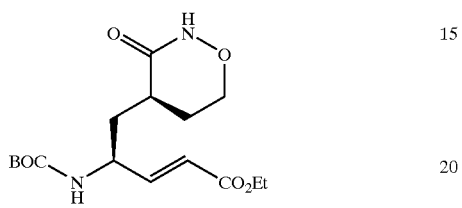

Especially preferred intermediates include the following compounds:

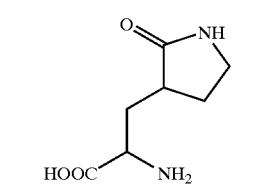
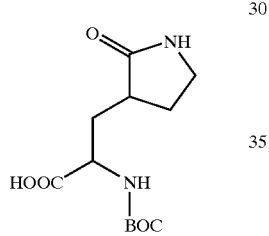

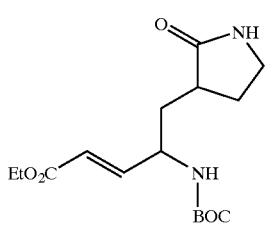
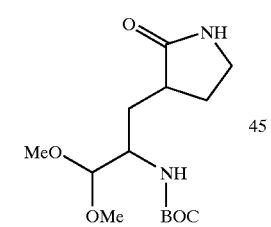

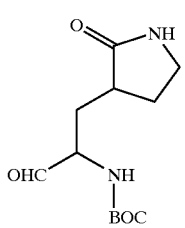
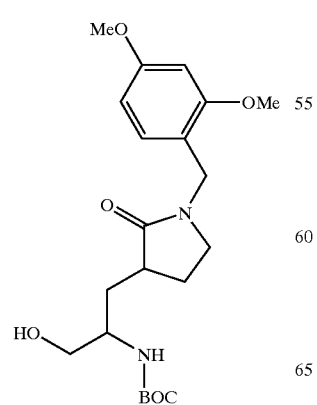

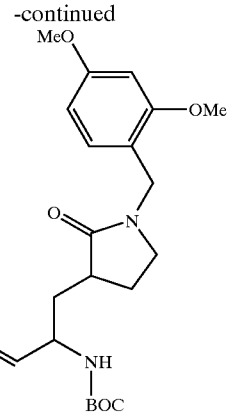

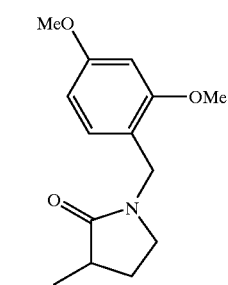

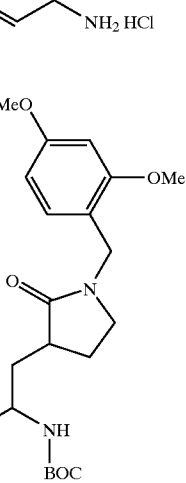

In accordance with a convention used in the art,

is used in structural formulas herein to depict the bond that is the point of attachment of the moiety or substituent to the core or backbone structure.

Where chiral carbons are included in chemical structures, unless a particular orientation is depicted, both stereoisomeric forms are intended to be encompassed.

As used herein, the term "alkyl group" is intended to mean a straight- or branched-chain monovalent radical of saturated and/or unsaturated carbon atoms and hydrogen atoms, such as methyl (Me), ethyl (Et), propyl, isopropyl, butyl, isobutyl, t-butyl, ethenyl, pentenyl, butenyl, propenyl, ethynyl, butynyl, propynyl, pentynyl, hexynyl, and the like, which may be unsubstituted (i.e., containing only carbon and hydrogen) or substituted by one or more suitable substituents as defined below (e.g., one or more halogens, such as F, Cl, Br, or I, with F and Cl being preferred). A "lower alkyl group" is intended to mean an alkyl group having from 1 to 4 carbon atoms in its chain.

A "cycloalkyl group" is intended to mean a non-aromatic monovalent monocyclic, bicyclic, or tricyclic radical containing 3, 4, 5, 6, 7, 8, 9, 10, 11, 12, 13, or 14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more substituents. Illustrative examples of cycloalkyl groups include the following moieties:

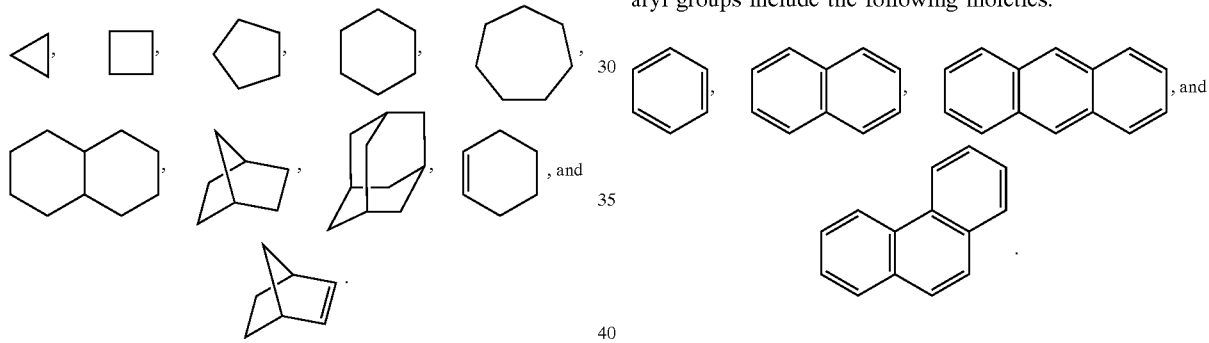

A "heterocycloalkyl group" is intended to mean a non-aromatic monovalent monocyclic, bicyclic, or tricyclic radical, which is saturated or unsaturated, containing 3, 4, 5, 6, 7, 8, 9, 10, 11, 12, 13, 14, 15, 16, 17, or 18 ring atoms, which includes 1, 2, 3, 4, or 5 heteroatoms selected from nitrogen, oxygen, and sulfur, where the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include the following moieties:

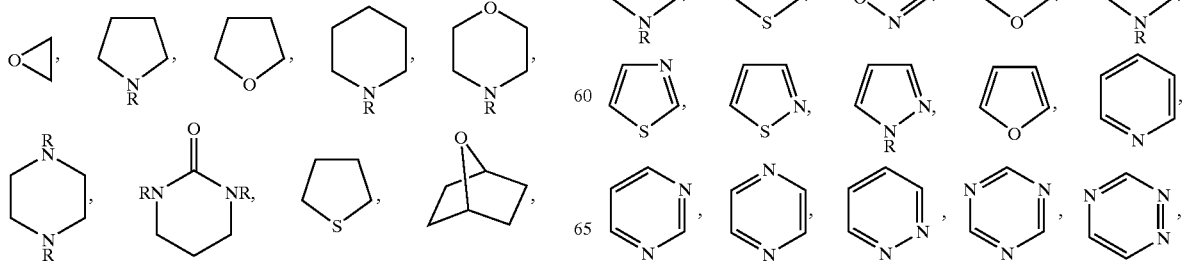

An "aryl group" is intended to mean an aromatic monovalent monocyclic, bicyclic, or tricyclic radical containing 6, 10, 14, or 18 carbon ring atoms, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Illustrative examples of aryl groups include the following moieties:

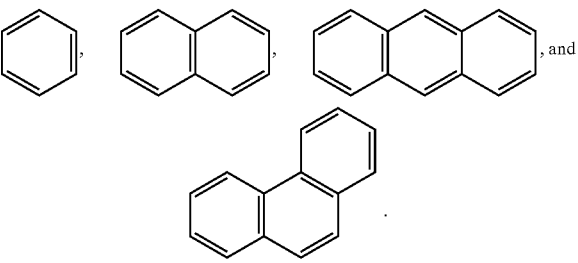

A "heteroaryl group" is intended to mean an aromatic monovalent monocyclic, bicyclic, or tricyclic radical containing 4, 5, 6, 7, 8, 9, 10, 11, 12, 13, 14, 15, 16, 17, or 18 ring atoms, including 1, 2, 3, 4, or 5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include the following moieties:

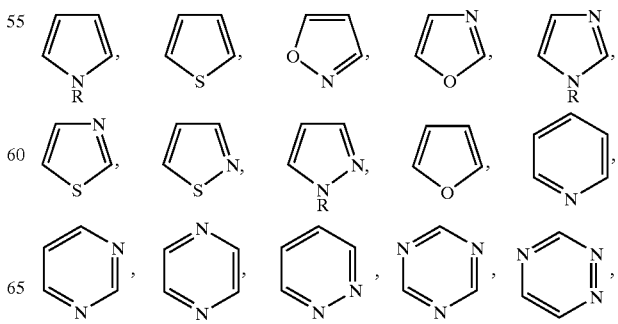

A "heterocycle" is intended to mean a heteroaryl or heterocycloalkyl group (each of which, as defined above, are optionally substituted).

An "acyl group" is intended to mean a —C(O)—R radical, where R is a substituent as defined below.

A "thioacyl group" is intended to mean a —C(S)—R radical, where R is a substituent as defined below.

A "sulfonyl group" is intended to mean a —SO₂R radical, where R is a substituent as defined below.

A "hydroxy group" is intended to mean the radical —OH.

An "amino group" is intended to mean the radical —NH₂.

An "alkylamino group" is intended to mean the radical —NHR$_a$, where R$_a$ is an alkyl group.

A "dialkylamino group" is intended to mean the radical —NR$_a$R$_b$, where R$_a$ and R$_b$ are each independently an alkyl group.

An "alkoxy group" is intended to mean the radical —OR$_a$, where R$_a$ is an alkyl group. Exemplary alkoxy groups include methoxy, ethoxy, propoxy, and the like.

An "alkoxycarbonyl group" is intended to mean the radical —C(O)OR$_a$, where R$_a$ is an alkyl group.

An "alkylsulfonyl group" is intended to mean the radical —SO₂R$_a$, where R$_a$ is an alkyl group.

An "alkylaminocarbonyl group" is intended to mean the radical —C(O)NHR$_a$, where R$_a$ is an alkyl group.

A "dialkylaminocarbonyl group" is intended to mean the radical —C(O)NR$_a$R$_b$, where R$_a$ and R$_b$ are each independently an alkyl group.

A "mercapto group" is intended to mean the radical —SH.

An "alkylthio group" is intended to mean the radical —SR$_a$, where R$_a$ is an alkyl group.

A "carboxy group" is intended to mean the radical —C(O)OH.

A "carbamoyl group" is intended to mean the radical —C(O)NH₂.

An "aryloxy group" is intended to mean the radical —OR$_c$, where R$_c$ is an aryl group.

A "heteroaryloxy group" is intended to mean the radical —OR$_d$, where R$_d$ is a heteroaryl group.

An "arylthio group" is intended to mean the radical —SR$_c$, where R$_c$ is an aryl group.

A "heteroarylthio group" is intended to mean the radical —SR$_d$, where R$_d$ is a heteroaryl group.

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxy groups, alkyl groups, oxo groups, cycloalkyl groups, heterocycloalkyl groups, aryl groups, heteroaryl groups, acyl groups, sulfonyl groups, mercapto groups, alkylthio groups, alkoxy groups, carboxy groups, amino groups, alkylamino groups, dialkylamino groups, carbamoyl groups, arylthio groups, heteroarylthio groups, and the like.

The term "substituent" or "suitable substituent" is intended to mean any suitable substituent that may be recognized or selected, such as through routine testing, by those skilled in the art. Illustrative examples of suitable substituents include hydroxy groups, halogens, oxo groups, alkyl groups, acyl groups, sulfonyl groups, mercapto groups, alkylthio groups, alkoxy groups, cycloalkyl groups, heterocycloalkyl groups, aryl groups, heteroaryl groups, carboxy groups, amino groups, alkylamino groups, dialkylamino groups, carbamoyl groups, aryloxy groups, heteroaryloxy groups, arylthio groups, heteroarylthio groups, and the like.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

A "prodrug" is intended to mean a compound that is converted under physiological conditions or by solvolysis or metabolically to a specified compound that is pharmaceutically active.

A "pharmaceutically active metabolite" is intended to mean a pharmacologically active product produced through metabolism in the body of a specified compound.

A "solvate" is intended to mean a pharmaceutically acceptable solvate form of a specified compound that retains the biological effectiveness of such compound. Examples of solvates include compounds of the invention in combination with water, isopropanol, ethanol, methanol, DMSO, ethyl acetate, acetic acid, or ethanolamine.

A "pharmaceutically acceptable salt" is intended to mean a salt that retains the biological effectiveness of the free acids and bases of the specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates.

If an inventive compound is a base, a desired salt may be prepared by any suitable method known to the art, including treatment of the free base with an inorganic acid, such as hydrochloric acid; hydrobromic acid; sulfuric acid; nitric acid; phosphoric acid; and the like, or with an organic acid, such as acetic acid; maleic acid; succinic acid; mandelic acid; fumaric acid; malonic acid; pyruvic acid; oxalic acid; glycolic acid; salicylic acid; pyranosidyl acid, such as glucuronic acid or galacturonic acid; alpha-hydroxy acid, such as citric acid or tartaric acid; amino acid, such as aspartic acid or glutamic acid; aromatic acid, such as benzoic acid or cinnamic acid; sulfonic acid, such as p-toluenesulfonic acid or ethanesulfonic acid; or the like.

If an inventive compound is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

In the case of compounds, salts, or solvates that are solids, it is understood by those skilled in the art that the inventive compounds, salts, and solvates may exist in different crystal forms, all of which are intended to be within the scope of the present invention and specified formulas.

The inventive compounds may exist as single stereoisomers, racemates, and/or mixtures of enantiomers and/or diastereomers. All such single stereoisomers, racemates, and mixtures thereof are intended to be within the broad scope of the present invention. Preferably, however, the inventive compounds are used in optically pure form.

As generally understood by those skilled in the art, an optically pure compound is one that is enantiomerically pure. As used herein, the term "optically pure" is intended to mean a compound comprising at least a sufficient activity. Preferably, an optically amount of a single enantiomer to yield a compound having the desired pharmacological pure compound of the invention comprises at least 90% of a single isomer (80% enantiomeric excess), more preferably at least 95% (90% e.e.), even more preferably at least 97.5% (95% e.e.), and most preferably at least 99% (98% e.e.).

Preferably in the compounds of the formula I (or of any of the subgeneric formula), $R_1$ is H or F.

In the compounds of formula I, preferably $R_9$ is an unsubstituted or substituted isoxazolyl group, where the optional substituents are preferably one or two methyl groups and/or halogens.

Especially preferred embodiments of the invention are described below in reference to the following formula I-A":

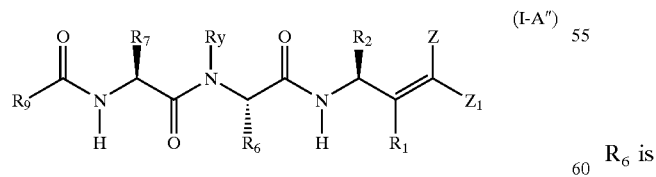

(I-A")

Preferred compounds of the present invention include peptido (peptide-like) Compounds (A-1)–(A-8) of the formula I-A" above, wherein $R_1$ is H, Z is H, $R_y$ is H, and $R_2$, $R_6$, $R_7$, $Z_1$, and $R_9$ are as respectively defined below:

(A-1) $R_2$ is $CH_2CH_2C(O)NH_2$, $R_6$ is $CH_2Ph$, $R_7$ is $CH_2CH(CH_3)_2$, $Z_1$ is $CO_2CH_2CH_3$, and $R_9$ is

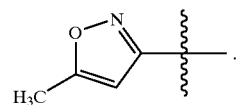

(A-2) $R_2$ is $CH_2CH_2C(O)NH_2$, $R_6$ is $CH_2Ph$, $R_7$ is $CH_2CH(CH_3)_2$, $Z_1$ is $CO_2CH_2CH_3$, and $R_9$ is

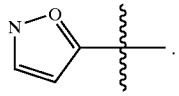

(A-3) $R_2$ is $CH_2CH_2C(O)NH_2$, $R_6$ is

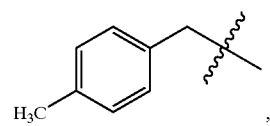

$R_7$ is $C(CH_3)_3$, $Z_1$ is $CO_2CH_2CH_3$, and $R_9$ is

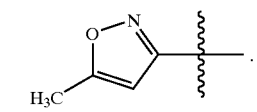

(A-4) $R_2$ is $CH_2CH_2C(O)NH_2$, $R_6$ is

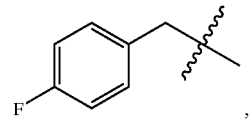

$R_7$ is $C(CH_3)_3$, $Z_1$ is $CO_2CH_2CH_3$, and $R_9$ is

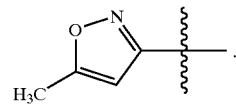

(A-5) $R_2$ is

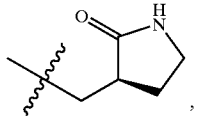

$R_6$ is

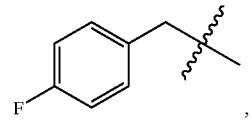

$R_7$ is $CH(CH_3)_2$, $Z_1$ is $CO_2CH_2CH_3$, and $R_9$ is

[5-methyl-isoxazol-3-yl group, with $H_3C$ on oxazole].

(A-6) $R_2$ is $CH_2CH_2C(O)NH_2$, $R_6$ is

[4-fluorobenzyl group].

$R_7$ is $CH(CH_3)_2$, $Z_1$ is $CO_2CH_2CH_3$, and $R_9$ is

[5-methyl-isoxazol-3-yl group].

(A-7) $R_2$ is

[3-substituted-2-oxopyrrolidine (γ-lactam) group].

$R_6$ is

[4-fluorobenzyl group].

$R_7$ is $C(CH_3)_3$, $Z_1$ is $CO_2CH_2CH_3$, and $R_9$ is

[5-methyl-isoxazol-3-yl group].

(A-8) $R_2$ is

[3-substituted-2-oxopiperidine (δ-lactam) group].

$R_6$ is

[4-fluorobenzyl group].

$R_7$ is $CH(CH_3)_2$, $Z_1$ is $CO_2CH_2CH_3$, and $R_9$ is

[4-fluorobenzyl group].

Preferred peptide-like compounds of the formula I-A"" further include Compounds (A-9)–(A-13) below, wherein $R_1$ is H, Z is H, $Z_1$ is $CO_2CH_2CH_3$, $R_y$ is $CH_3$, and $R_2$, $R_6$, $R_7$, and $R_9$ are as respectively defined below:

(A-9) $R_2$ is $CH_2CH_2C(O)NH_2$, $R_6$ is

[4-fluorobenzyl group].

$R_7$ is

[imidazol-4-ylmethyl group].

and $R_9$ is

[5-methyl-isoxazol-3-yl group].

(A-10) $R_2$ is $CH_2CH_2C(O)NH_2$, $R_6$ is $CH_2Ph$, $R_7$ is $CH_2CH(CH_3)_2$, and $R_9$ is

[5-methyl-isoxazol-3-yl group].

(A-11) $R_2$ is $CH_2CH_2C(O)NH_2$, $R_6$ is

[4-fluorobenzyl group].

$R_7$ is

[naphth-2-ylmethyl group].

and R₉ is
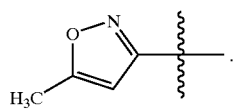
(A-12) R₂ is CH₂CH₂C(O)NH₂, R₆ is
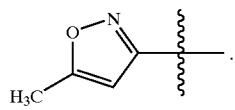
R₇ is CH₂CH(CH₃)₂, and R₉ is
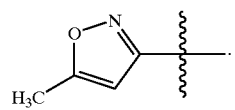
(A-13) R₂ is CH₂CH₂C(O)NH₂, R₆ is
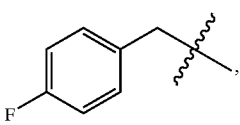
R₇ is
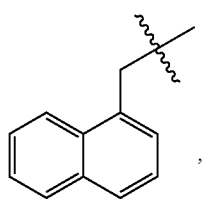
and R₉ is
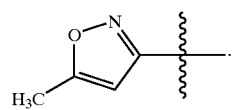
Other preferred peptide-like compounds include the following:
(A-14)
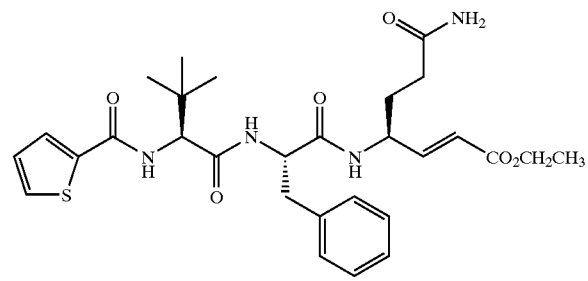
(A-15)
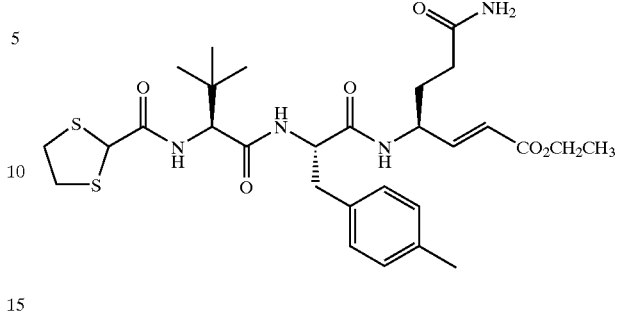
(A-16)
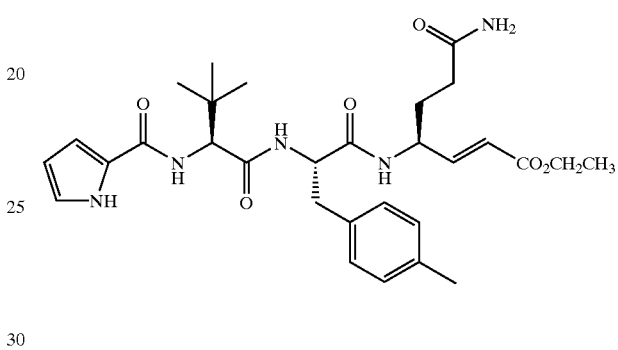
(A-17)
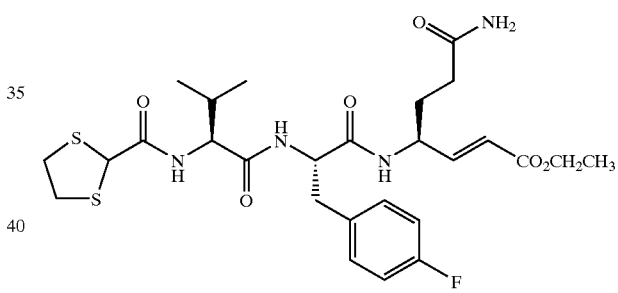
(A-18)
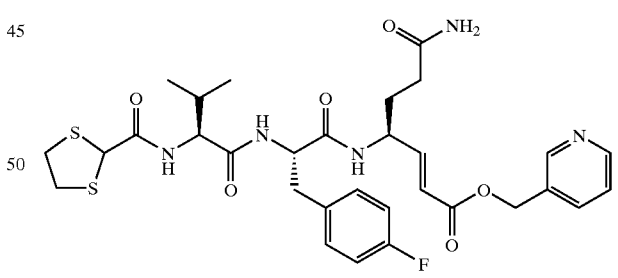
(A-19)
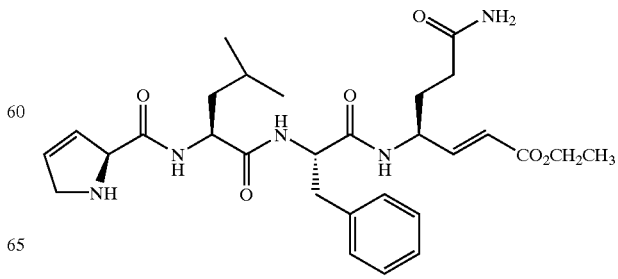

-continued
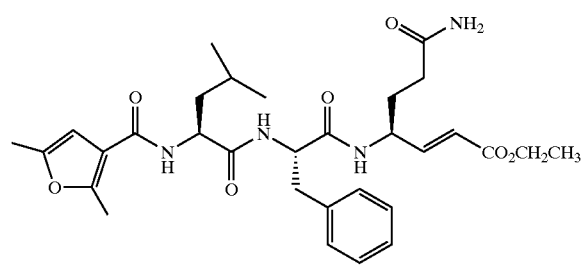
(A-20)
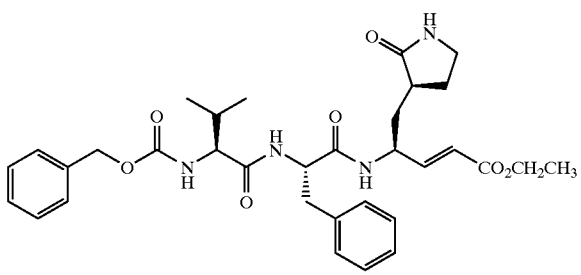
(A-25)
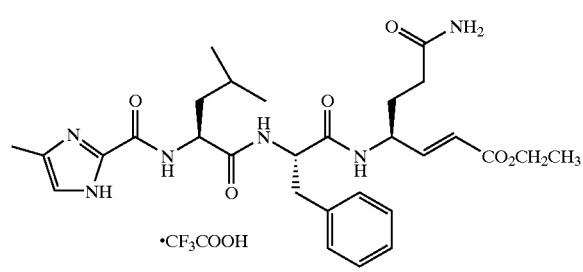
(A-21)
·CF₃COOH
(A-22)
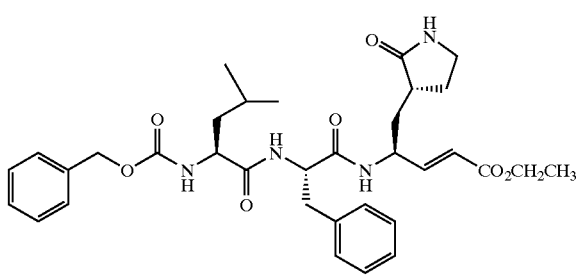
(A-26)
(A-27)
(A-23)
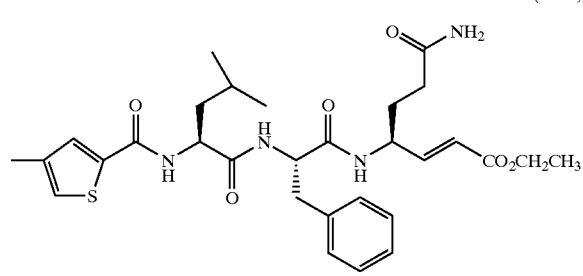
(A-28)
(A-24)
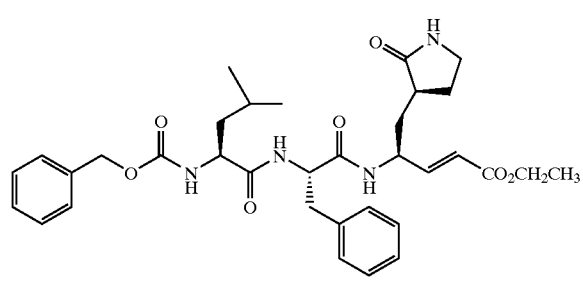
Preferred ketomethylene-type Compounds (B-1)–(B-4) of the invention are described below in reference to the following formula I-B":
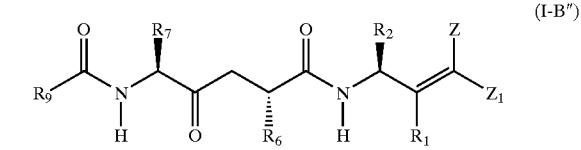
(I-B")

(B-1) R$_2$ is CH$_2$CH$_2$C(O)NH$_2$, R$_6$ is

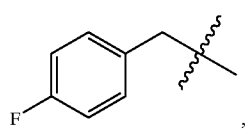,

R$_7$ is CH(CH$_3$)$_2$, Z is H, Z$_1$ is CO$_2$CH$_2$CH$_3$, and R$_9$ is

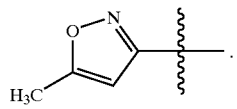.

(B-2) R$_2$ is

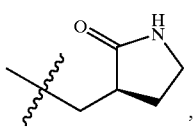,

R$_6$ is

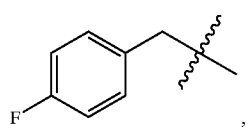,

R$_7$ is CH(CH$_3$)$_2$, Z is H, Z$_1$ is CO$_2$CH$_2$CH$_3$, and R$_9$ is

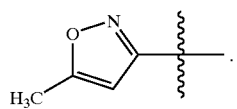.

(B-3) R$_2$ is

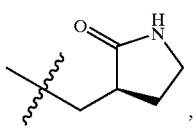,

R$_6$ is

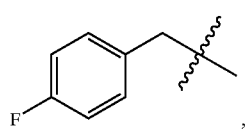,

R$_7$ is CH(CH$_3$)$_2$, Z and Z$_1$ together are

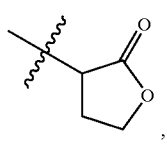, where the carbonyl group is cis to the hydrogen corresponding to R$_1$ in formula I, and R$_9$ is

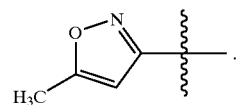.

(B-4) R$_2$ is

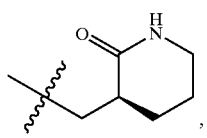,

R$_6$ is

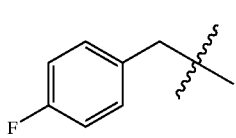,

R$_7$ is CH(CH$_3$)$_2$, Z is H, Z$_1$ is CO$_2$CH$_2$CH$_3$, and R$_9$ is

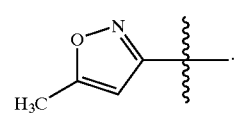.

Preferred depsipeptide-type Compounds (C-1) and (C-2) of the invention are described below in reference to the following formula I-C", where R$_1$ is H:

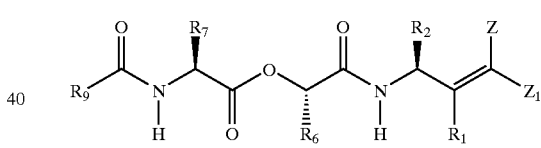

(I-C")

(C-1) Z is H, R$_2$ is CH$_2$CH$_2$C(O)NH$_2$, R$_6$ is

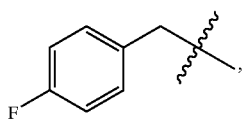,

R$_7$ is CH(CH$_3$)$_2$, Z$_1$ is CO$_2$CH$_2$CH$_3$, and R$_9$ is

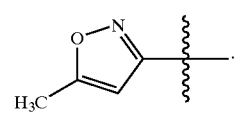.

(C-2) Z is H, R$_2$ is

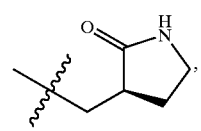, $R_6$ is

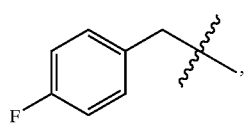

$R_7$ is $CH(CH_3)_2$, $Z_1$ is $CO_2CH_2CH_3$, and $R_9$ is

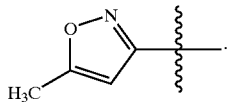

Additional compounds may be prepared in reference to formula I by selecting the variables from the following substituents:

$R_y$=H or $CH_3$;

$R_1$=H or $CH_3$;

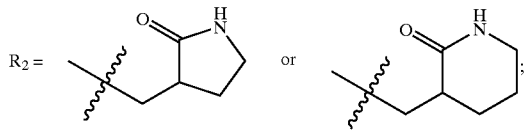

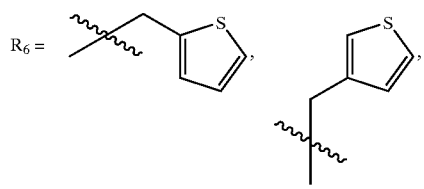

or phenylmethyl (i.e., benzyl), where the aryl group is optionally substituted with one, two, or three substituents each independently selected from halogens, methoxy and methyl;

$R_7$=2-methyl-1-propyl, 2-propyl, 2-methyl-2-propyl, benzyl, or

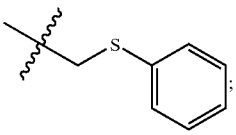

and

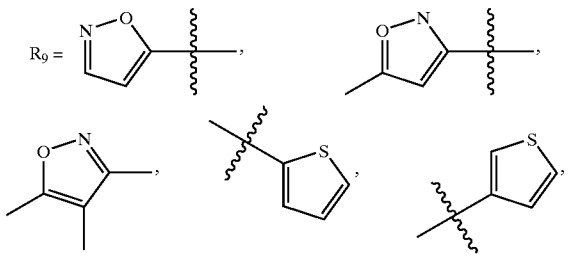

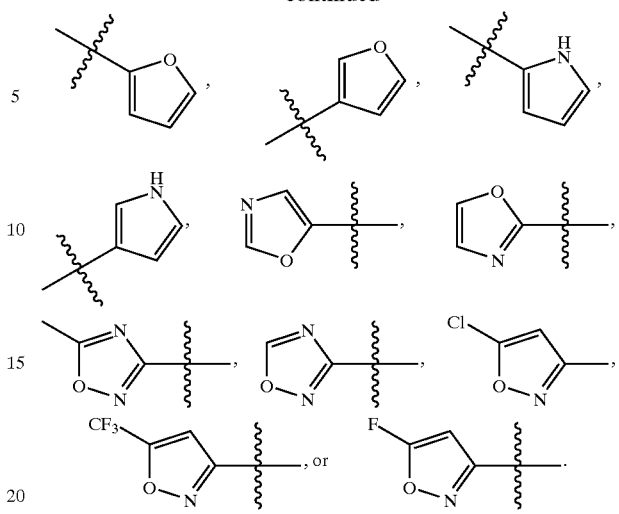

The present invention is also directed to a method of inhibiting picornaviral 3C protease activity, comprising contacting the protease with an effective amount of a compound of formula I, or a pharmaceutically acceptable salt, prodrug, pharmaceutically active metabolite, or solvate thereof. For example, picornaviral 3C protease activity may be inhibited in mammalian tissue by administering a compound of formula I or a pharmaceutically acceptable salt, prodrug, pharmaceutically active metabolite, or solvate thereof. More preferably, the present method is directed at inhibiting rhinoviral protease activity.

"Treating" or "treatment" is intended to mean at least the mitigation of a disease condition in a mammal, such as a human, that is alleviated by the inhibition of the activity of one or more picornaviral 3C proteases, such as human rhinoviruses, human poliovirus, human coxsackieviruses, encephalomyocarditis viruses, meningitis virus, and hepatitis A virus, and includes: (a) prophylactic treatment in a mammal, particularly when the mammal is found to be predisposed to having the disease condition but not yet diagnosed as having it; (b) inhibiting the disease condition; and/or (c) alleviating, in whole or in part, the disease condition.

The activity of the inventive compounds as inhibitors of picornaviral 3C protease activity may be measured by any of the suitable methods known to those skilled in the art, including in vivo and in vitro assays. An example of a suitable assay for activity measurements is the antiviral H1-HeLa cell culture assay described herein.

Administration of the compounds of the formula I and their pharmaceutically acceptable prodrugs, salts, active metabolites, and solvates may be performed according to any of the accepted modes of administration available to those skilled in the art. Illustrative examples of suitable modes of administration include oral, nasal, parenteral, topical, transdermal, and rectal. Intranasal delivery is especially preferred.

An inventive compound of formula I or a pharmaceutically acceptable salt, prodrug, active metabolite, or solvate thereof may be administered as a pharmaceutical composition in any pharmaceutical form recognizable to the skilled artisan as being suitable. Suitable pharmaceutical forms include solid, semisolid, liquid, or lyophilized formulations, such as tablets, powders, capsules, suppositories, suspensions, liposomes, and aerosols. Pharmaceutical compositions of the invention may also include suitable excipients, diluents, vehicles, and carriers, as well as other pharmaceutically active agents, depending upon the intended use. In preferred embodiments, the inventive pharmaceutical compositions are delivered intranasally in the form of suspensions.

Acceptable methods of preparing suitable pharmaceutical forms of the pharmaceutical compositions are known or may be routinely determined by those skilled in the art. For example, pharmaceutical preparations may be prepared following conventional techniques of the pharmaceutical chemist involving steps such as mixing, granulating, and compressing when necessary for tablet forms, or mixing, filling, and dissolving the ingredients as appropriate, to give the desired products for oral, parenteral, topical, intravaginal, intranasal, intrabronchial, intraocular, intraaural, and/or rectal administration.

Solid or liquid pharmaceutically acceptable carriers, diluents, vehicles, or excipients may be employed in the pharmaceutical compositions. Illustrative solid carriers include starch, lactose, calcium sulfate dihydrate, terra alba, sucrose, talc, gelatin, pectin, acacia, magnesium stearate, and stearic acid. Illustrative liquid carriers include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., solution), or a non-aqueous or aqueous liquid suspension.

A dose of the pharmaceutical composition contains at least a therapeutically effective amount of the active compound (i.e., a compound of formula I or a pharmaceutically acceptable salt, prodrug, active metabolite, or solvate thereof), and preferably is made up of one or more pharmaceutical dosage units. The selected dose may be administered to a mammal, for example, a human patient, in need of treatment mediated by inhibition of picornaviral 3C protease activity, by any known or suitable method of administering the dose, including topically, for example, as an ointment or cream; orally; rectally, for example, as a suppository; parenterally by injection; or continuously by intravaginal, intranasal, intrabronchial, intraaural, or intraocular infusion.

A "therapeutically effective amount" is intended to mean the amount of an inventive compound that, when administered to a mammal in need thereof, is sufficient to effect treatment for disease conditions alleviated by the inhibition of the activity of one or more picornaviral 3C proteases, such as human rhinoviruses, human poliovirus, human coxsackieviruses, encephalomyocarditis viruses, menigovirus, and hepatitis A virus. The amount of a given compound of the invention that will be therapeutically effective will vary depending upon factors such as the particular compound, the disease condition and the severity thereof, the identity of the mammal in need thereof, which amount may be routinely determined by artisans.

By way of illustration, a formulation for nasal delivery of the inventive compounds for treatment of rhinoviral infections can be prepared as follows, where all percentages are weight/weight and the suspension is prepared in purified water. A formula-I compound is micronized to a reduced particle size such that $D_{90}<10$ µm. A suspension is prepared to contain a final concentration of from about 0.01% to about 2% of the active compound, preferably about from 0.2% to 2%. An appropriate preservative selected from those known in the art may be included, for example, benzalkonium chloride/EDTA, in appropriate final-concentration ranges, e.g., about 0.02%/0.01%. A suspending agent, such as mixture of microcrystalline cellulose (final concentration of about 1%–1.5%, preferably about 1.2%) and sodium carboxymethylcellulose cellulose (final concentration of about 0.1%–0.2%, preferably about 0.13%) may be included. A surfactant such as polysorbate 80 may be included in a final concentration of about from 0.05% to 0.2%, preferably about 0.1%. A tonicity modifier such as dextrose may be included to give a final concentration of about from 4% to 6%, preferably about 5%. The pH of the final solution is adjusted as appropriate to a physiological range, e.g., 4–6, using non-toxic acid and/or base, such as HCl and/or NaOH.

An exemplary formulation for nasal delivery of the inventive compound of Example 17 has the following composition, where all percentages are weight/weight and the suspension is prepared in purified water:

| | | |
|---|---|---|
| Active Compound | (B-2) | 0.2–2% |
| Preservative | Benzalkonium chloride/EDTA | 0.02%/0.01% |
| Suspending Agent | Microcrystalline cellulose/Na-carboxymethylcellulose | 1.2%/0.13% |
| Surfactant | Polysorbate 80 | 0.1% |
| Tonicity Modifier | Dextrose | 5% |
| pH Adjustment | NaOH/HCl | pH 4–6 |

GENERAL SYNTHESES

The inventive compounds of formula (I) may be advantageously prepared by the methods of the present invention, including the general methods described below. In each of these general methods, $R_1$, $R_2$, $R_3$, $R_5$, $R_6$, $R_7$, $R_8$, $R_9$, $R_y$, Z, and $Z_1$ are as defined above, and $R_4$ is used (as a shorthand representation) to mean:

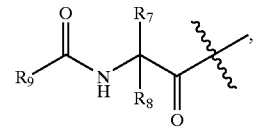

where $R_7$, $R_8$, and $R_9$ are as defined above.

In General Method I, useful for synthesis of peptide-like compounds of formula I-A, an amino acid A, where $P_1$ is an appropriate protecting group for nitrogen, is subjected to an amide-forming reaction with amino alcohol (or salt thereof) B to produce amide C. Compound C is then deprotected to give free amine (or salt thereof) D. Amine D and amino acid E, which may incorporate either an $R_4$ group or a protecting group for nitrogen ($P_2$), are subjected to a bond-forming reaction generating compound F. Compound F is oxidized to intermediate G, which is then transformed into unsaturated product H. If protecting groups have been used on amino acid E, or on any R groups ($R_1$–$R_9$) and/or on $R_y$ and/or on Z and/or $Z_1$, product H is deprotected and/or further modified to yield deprotected or modified H.

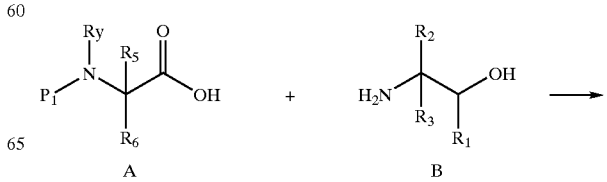

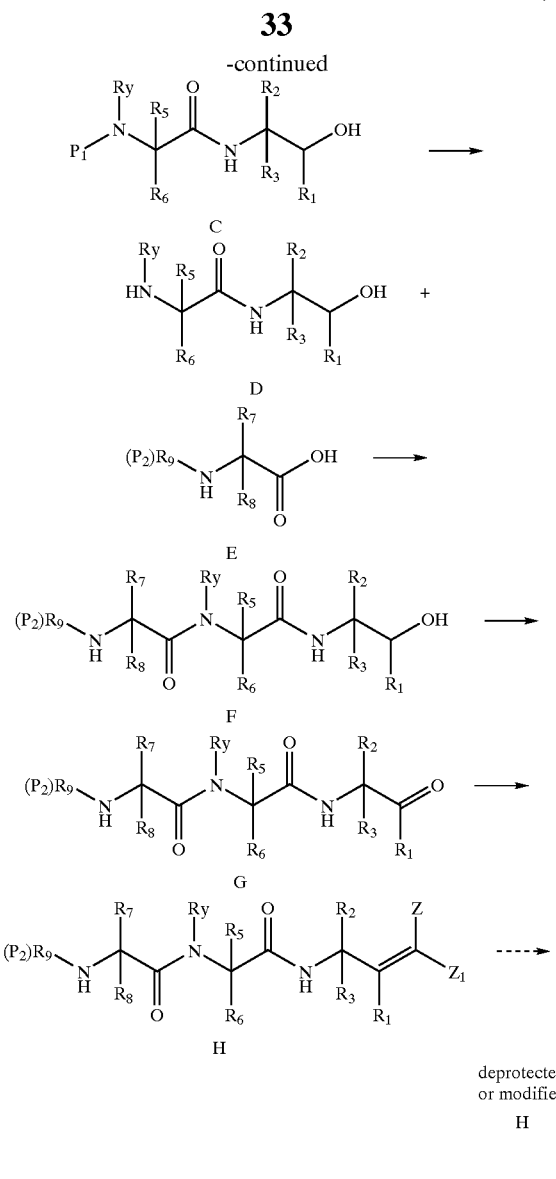

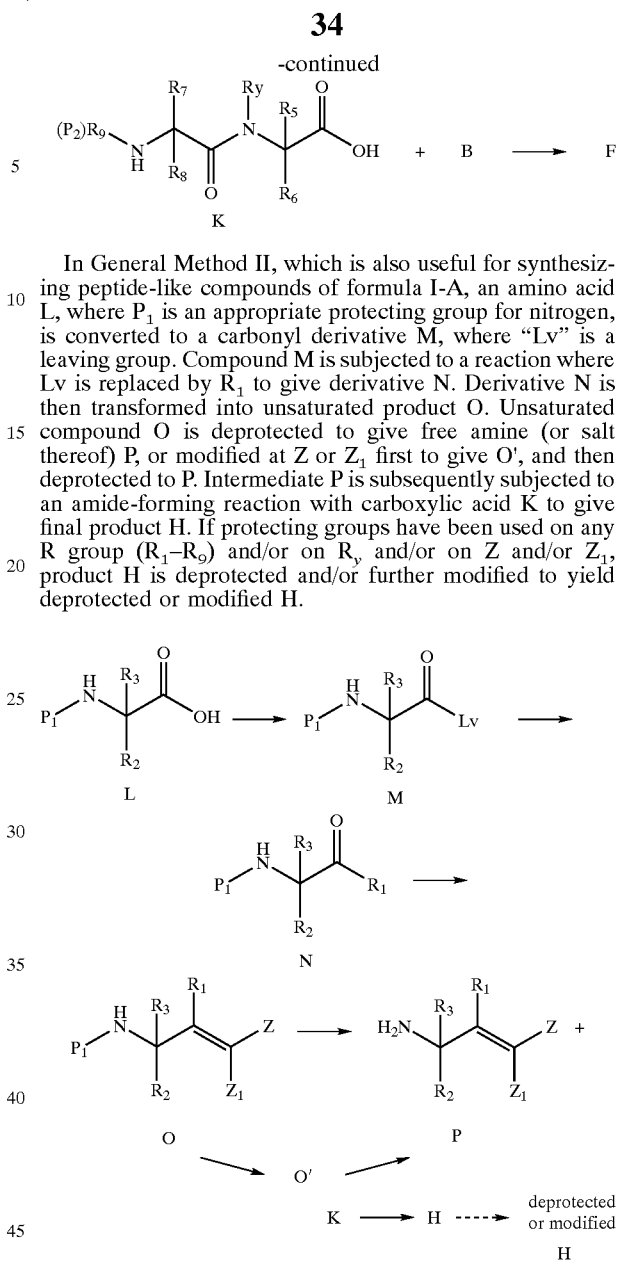

In General Method II, which is also useful for synthesizing peptide-like compounds of formula I-A, an amino acid L, where $P_1$ is an appropriate protecting group for nitrogen, is converted to a carbonyl derivative M, where "Lv" is a leaving group. Compound M is subjected to a reaction where Lv is replaced by $R_1$ to give derivative N. Derivative N is then transformed into unsaturated product O. Unsaturated compound O is deprotected to give free amine (or salt thereof) P, or modified at Z or $Z_1$ first to give O', and then deprotected to P. Intermediate P is subsequently subjected to an amide-forming reaction with carboxylic acid K to give final product H. If protecting groups have been used on any R group ($R_1$–$R_9$) and/or on $R_y$ and/or on Z and/or $Z_1$, product H is deprotected and/or further modified to yield deprotected or modified H.

An alternative method to prepare intermediate F is described as follows. Amino acid E and amino acid (or salt thereof) I, where $P_3$ is an appropriate protecting group for oxygen, are subjected to a bond-forming reaction to produce intermediate J. Molecule J is deprotected to yield free carboxylic acid K, which is subsequently subjected to an amide-forming reaction with amino alcohol (or salt thereof) B to generate intermediate F.

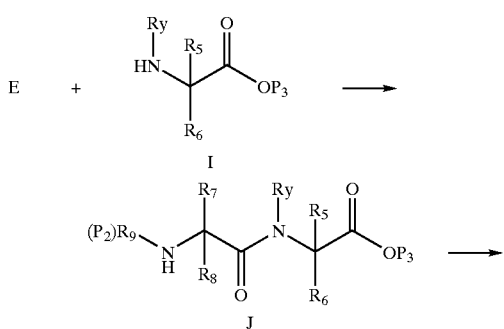

An alternative method to prepare intermediate N is described as follows. Compound M is subjected to a reaction where "Lv" (or more particularly —C(O)—Lv), is reduced to protected amino alcohol Q. Intermediate Q is subsequently oxidized to derivative N.

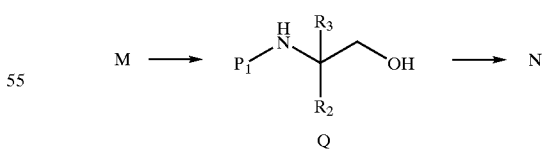

In General Method III, useful for synthesis of peptide-like compounds of formula I-A, an amino acid L, where $P_1$ is an appropriate protecting group for nitrogen, is converted to a carbonyl derivative M, where "Lv" is a leaving group. Compound M is deprotected to give free amine (or salt thereof) R, which subsequently is subjected to an amide-forming reaction with carboxylic acid K to give intermediate S. Compound S is then either directly converted to carbonyl intermediate G, or successively reduced to alcohol F first, which is oxidized to G. Compound G is subjected to a reaction to yield the unsaturated final product H. If protecting groups have been used on any R groups (R$_1$–R$_9$) and/or on R$_y$ and/or on Z and/or Z$_1$, product H is deprotected and/or further modified to yield deprotected or modified H.

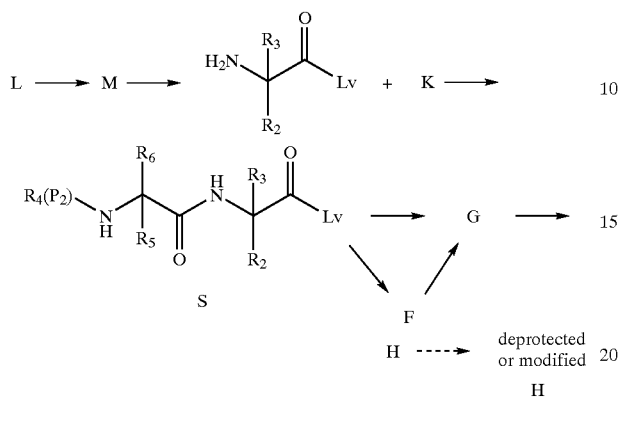

In General Method IV, useful for synthesis of peptide-like compounds of formula I-A, free amine (or salt thereof) P, prepared from intermediate O as described in General Method II, is converted to amide T by reaction with amino acid A, where P$_1$ is an appropriate protecting group for nitrogen. Compound T is further deprotected to free amine (or salt thereof) U, which is subsequently converted to H with amino acid E. If protecting groups have been used on any R groups (R$_1$–R$_9$) and/or on R$_y$ and/or on Z and/or Z$_1$, product H is deprotected and/or further modified to yield deprotected or modified H.

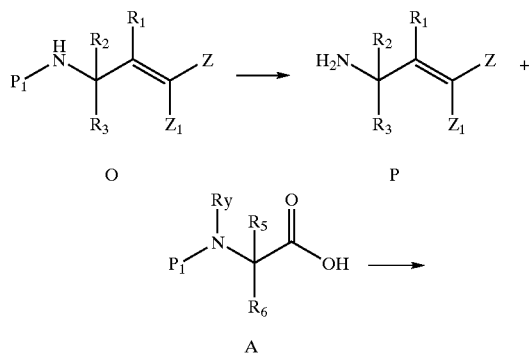

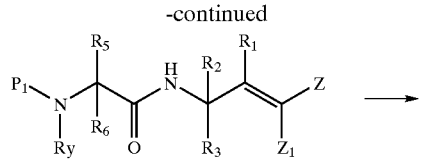

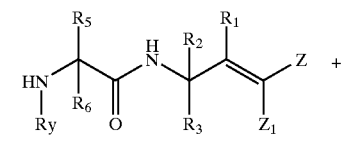

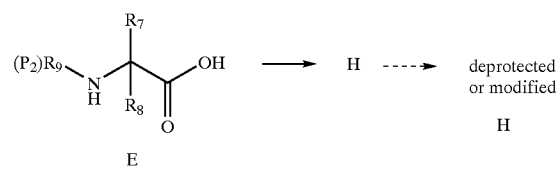

In General Method V, useful for synthesis of ketomethylene compounds of formula I-B, optically active lactone AA, where P$_4$ is an appropriate protecting group for nitrogen, and R$_5$ and R$_8$ are H (which may be prepared by the method described below and by various literature methods, including: (a) Herold et al., *J. Org. Chem.* 1989, 54, 1178; (b) Bradbury et al., *Tetrahedron Lett.* 1989, 30, 3845; (c) Bradbury et al., *J. Med. Chem.* 1990, 33, 2335; (d) Wuts et al., *J. Org. Chem.* 1992, 57, 6696; (e) Jones et al., *J. Org. Chem.* 1993, 58, 2286; (f) Pégorier et al., *Tetrahedron Lett.* 1995, 36, 2753; and (g) Dondoni et al., *J. Org. Chem.* 1995, 60, 7927) is transformed by a two-step procedure (basic hydrolysis and subsequent oxidation) into carboxylic acid BB. This material is not isolated, but is subjected to an amide-forming reaction with amine (or salt thereof) P to provide final product CC. The P$_4$ protecting group, along with any additional protecting groups that have been used on any R groups (R$_1$, R$_2$, R$_3$, R$_6$, and/or R$_7$) and/or on Z and/or on Z$_1$, is subsequently deprotected and/or further modified to yield deprotected or modified CC.

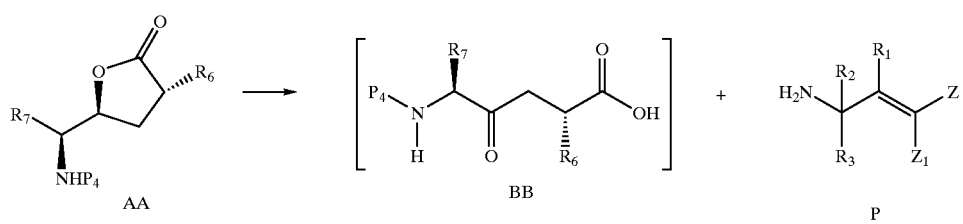

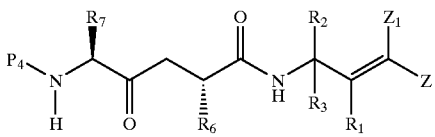

CC

Lactone AA may be prepared in optically active form by the following General Method VI (see: Herold et al., *J. Org. Chem.* 1989, 54, 1178; Bradbury et al., *Tetrahedron Lett.* 1989, 30, 3845; and Bradbury et al., *J. Med. Chem.* 1990, 33, 2335). A γ,δ-unsaturated carboxylic acid DD, which incorporates $R_7$, is transformed into the corresponding acid chloride (not shown). This acid chloride is subjected to an amide-forming reaction with a chiral amine or a chiral oxazolidone to provide derivative EE (in which $X_1$ is a chiral amine or a chiral oxazolidone). Compound EE is subsequently deprotonated, and the resulting enolate is diastereoselectively alkylated with an electrophile corresponding to $R_6$ to provide compound FF, where $R_5$ is H. This material is then subjected to a halolactonization reaction to provide halo-lactone GG, in which $R_5$ and $R_8$ are H and "hal" is Br or I. Halo-lactone GG is subsequently transformed into azide HH, and this material is then converted into lactone AA, where $P_4$ is an appropriate protecting group for nitrogen.

Carboxylic acid BB may also be prepared by General Method VIII (see: Hoffman et al., *Tetrahedron,* 1997, 53, 7119). An amino acid KK, which incorporates $R_7$ and where $P_4$ is an appropriate protecting group for nitrogen, is transformed into β-ketoester LL. Compound LL is deprotonated and the resulting anion is condensed with triflate MM, which incorporates $R_6$. The coupling product thus obtained is

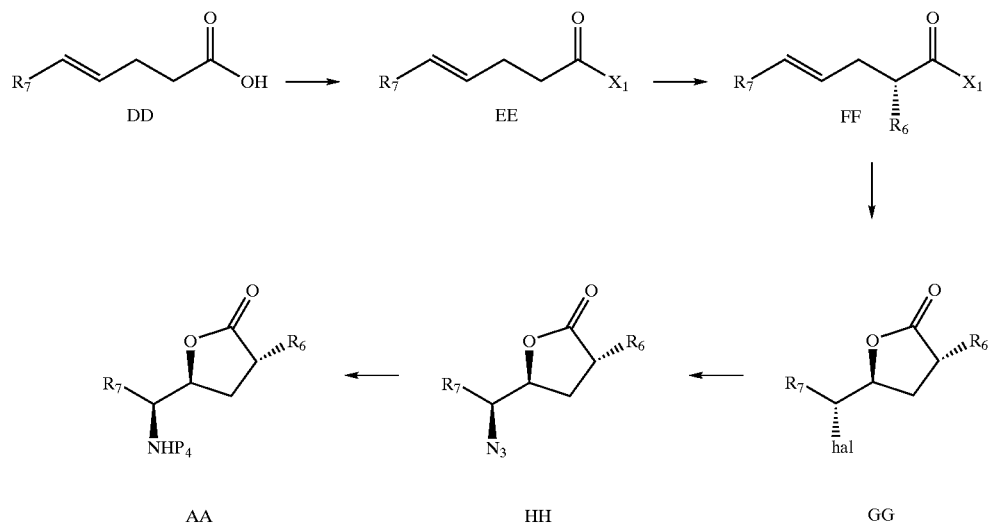

γ,δ-Unsaturated carboxylic acid DD may be prepared by the following General Method VII (see: Herold et al., *J. Org. Chem.* 1989, 54, 1178). An aldehyde II, which incorporates $R_7$, is coupled with vinylmagnesium bromide to give alcohol JJ. Alcohol JJ is then transformed into γ,δ-unsaturated carboxylic acid DD by a three-step procedure as follows: (i) treatment with diethyl malonate and catalytic Ti(OEt)$_4$ at 160° C. for 1 hour, (ii) heating at 190° C. for 4 hours, and (iii) hydrolysis with ethanolic KOH at reflux.

treated with trifluoroacetic acid to provide ketoester NN, and this material is subsequently hydrolyzed to afford carboxylic acid BB. If basic hydrolysis results in epimerization, ketoester NN can be transesterified (allyl alcohol, Ti(Oi-Pr)$_4$) and subsequently deprotected under neutral conditions (Pd(PPh$_3$)$_4$, morpholine) to give carboxylic acid BB. Triflate MM, in turn, may be prepared from the corresponding alcohol by treatment with trifluoromethanesulfonic anhydride and 2,6-lutidine.

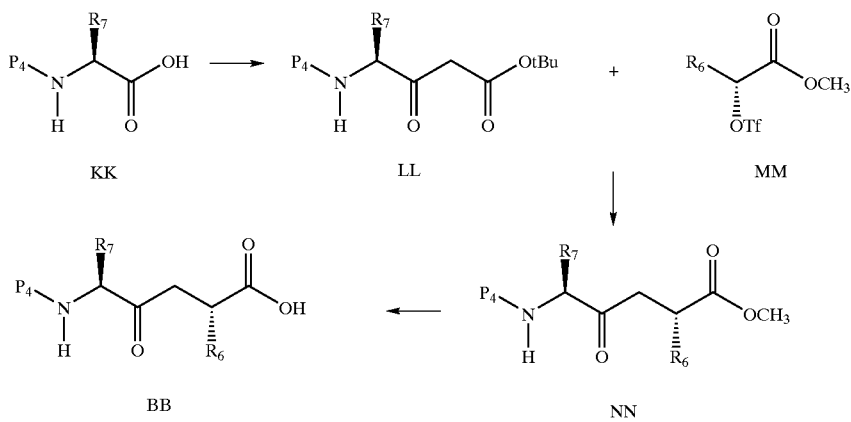

Lactone AA may also be prepared by General Method IX (see: Askin et al., *J. Org. Chem.* 1992, 57, 2771; and McWilliams et al., *J. Am. Chem. Soc.* 1996, 118, 11970). An amino acid KK, which incorporates $R_7$ and where $P_4$ is an appropriate protecting group for nitrogen, is transformed into epoxide OO (single diastereomer) by the method described in Luly et al., *J. Org. Chem.* 1987, 52, 1487. Epoxide OO is condensed with the anion derived from compound PP, which incorporates $R_6$ and in which $X_2$ is a chiral auxiliary (including (1S,2R)-1-aminoindan-2-ol acetonide) to afford coupling product QQ. This material is subsequently cyclized under acidic conditions to provide lactone AA. Compound PP may be prepared from the corresponding carboxylic acid (not shown) by the method outlined in Askin et al., *J. Org. Chem.* 1992, 57, 2771.

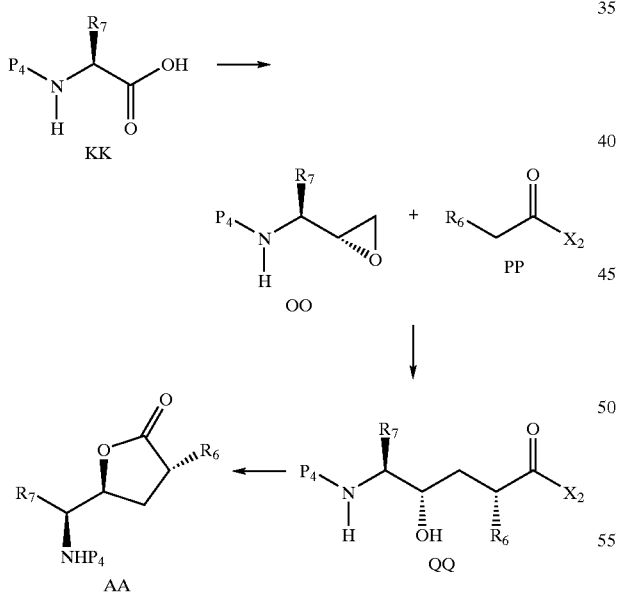

General Method X, useful in preparation of depsipeptide compounds of the formula I-C, illustrates a method to prepare intermediate TT. Amino acid E and alcohol RR, where $P_5$ is an appropriate protecting group for oxygen, are subjected to an ester bond-forming reaction to produce intermediate SS. Molecule SS is deprotected to yield free carboxylic acid TT, which may be utilized in lieu of carboxylic acid K in any of the general methods described above.

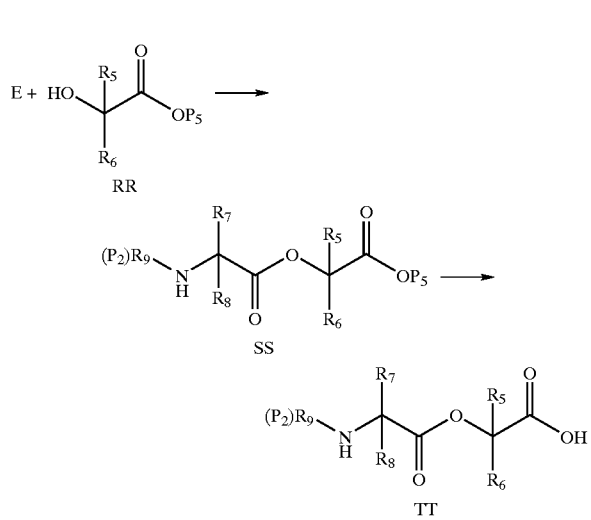

SPECIFIC SYNTHESES

The following specific methods may also be used to prepare various compounds according to the invention.

Specific Method I describes the preparation of specific intermediate O1, which may be utilized as intermediate O in the general methods described above. Thus, ester A1 (prepared as described in Chida et al., *J. Chem. Soc., Chem. Commun.* 1992, 1064) is hydrolyzed to give acid B1, which, in turn, is transformed into oxazolidinone C1. Compound C1 is subsequently deprotonated, and the resulting enolate is diastereoselectively alkylated to give allyl intermediate D1. This entity is oxidized via ozonolysis, and the resulting aldehyde (not shown) is subjected to a reductive amination reaction producing lactam E1. Acid-catalyzed methanolysis of E1 then affords alcohol F1. This intermediate is oxidized via the method of Swern (or other suitable oxidation conditions) to the resulting aldehyde (not shown), which is subsequently subjected to an olefin-forming reaction to provide specific intermediate O1.

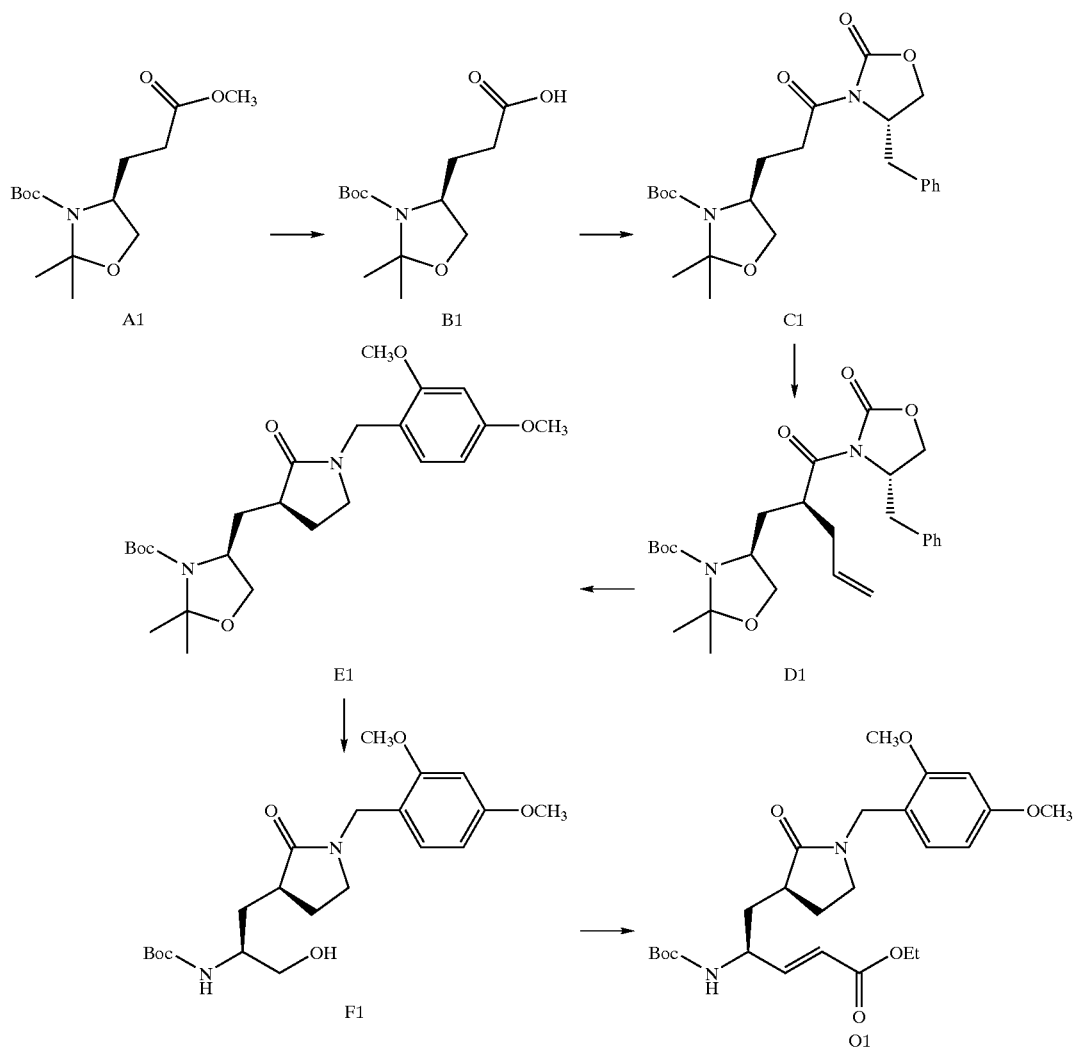

Specific Method II describes the preparation of specific intermediate O2, which may be utilized as intermediate O in the general methods described above. Allyl intermediate D1 is subjected to a hydroboration/oxidation sequence to afford a primary alcohol (not shown). This entity is oxidized via the method of Swern (or other suitable oxidation conditions), and the resulting aldehyde (not shown) is subjected to a reductive-amination reaction, producing lactam G1. Acid-catalyzed methanolysis of G1 then affords alcohol H1. This intermediate is oxidized via the method of Swern (or other suitable oxidation conditions) to the resulting aldehyde (not shown), which is subsequently subjected to an olefin-forming reaction to provide specific intermediate O2.

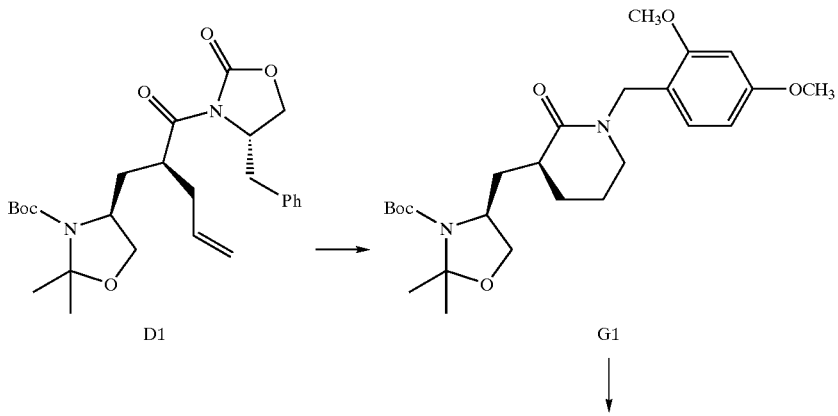

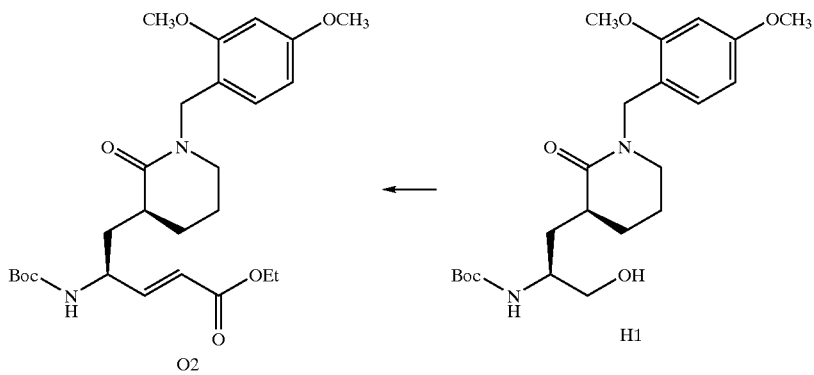

The following intermediates P1, P2, and P3 may be used in the above general methods in place of intermediate O, to vary the substituent group in the $R_2$ position.

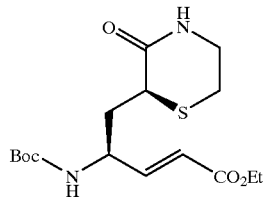

P1

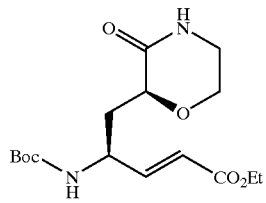

P2

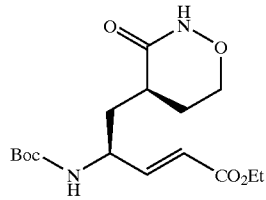

P3

A synthesis of intermediate P1 is described below. Intermediate C1 (described above) is deprotonated, and the resulting enolate is trapped with an appropriate disulfide (symmetrical or mixed) to give sulfide p1 (P is a suitable protecting group for oxygen). The oxygen-protecting group is then removed to give alcohol p2. This intermediate is oxidized via the method of Swern (or using other suitable oxidation conditions), and the resulting aldehyde (not shown) is subjected to a reductive amination reaction to give lactam p3. Acid-catalyzed methanolysis of p3 then affords alcohol p4. This intermediate is oxidized via the method of Swern (or using other suitable oxidation conditions) to the resulting aldehyde (also not shown), which is subsequently subjected to an olefin-forming reaction to provide intermediate p5. This compound may be utilized in place of intermediate O in the above general synthetic methods; alternatively, the lactam-protecting group may be removed to give intermediate P1.

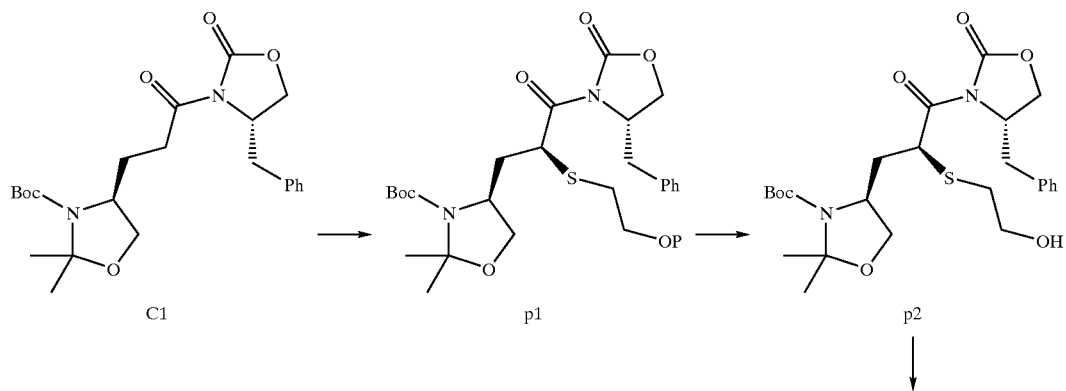

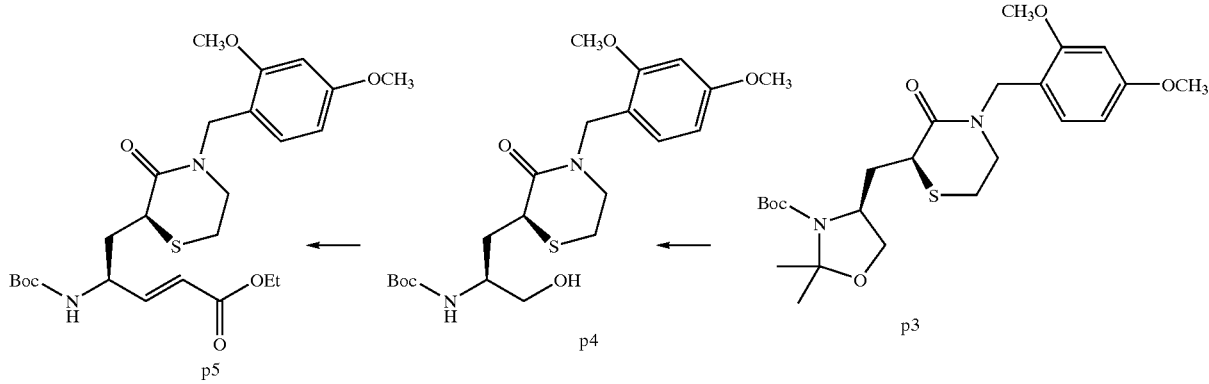

To synthesize intermediate P2, intermediate C1 is deprotonated, and the resulting enolate is trapped with an appropriate source of electrophilic oxygen (e.g., an oxaziridine) to give alcohol p6. This intermediate is alkylated with a suitably functionalized alkyl halide or triflate to give ether p7 (P is an appropriate protecting group for nitrogen). The nitrogen-protecting group is then removed, and the resulting amine (not shown) is subjected to cyclization conditions to give lactam p8. Acid-catalyzed methanolysis of p8 then affords alcohol p9. This intermediate is oxidized via the method of Swern (or using other suitable oxidation conditions) to the resulting aldehyde (also not shown), which is subsequently subjected to an olefin-forming reaction to provide intermediate P2.

A synthesis of specific intermediate P3 is now described. Intermediate D1 (described above) is ozonized, and the resulting aldehyde (not shown) is reduced to the corresponding alcohol (also not shown). This intermediate is then protected to afford compound p10 ($P_1$ is an appropriate protecting group for oxygen). The imide functionality present on p10 is hydrolyzed to carboxylic acid p11, and this intermediate is coupled with a suitably protected hydroxylamine derivative to give amide p12 ($P_2$ is an appropriate protecting group for oxygen that is stable to conditions which will remove $P_1$). The $P_1$ protecting group is then removed, and the resulting alcohol (p13) is transformed into an appropriate leaving group (halide or triflate, not shown). The $P_2$ protecting group is then removed, and the resulting hydroxamic acid is cyclized to give intermediate p14. Acid-catalyzed methanolysis of p14 then affords alcohol p15. This intermediate is oxidized via the method of Swern (or using other suitable oxidation conditions) to the resulting aldehyde (not shown), which is subsequently subjected to an olefin-forming reaction to provide intermediate P3.

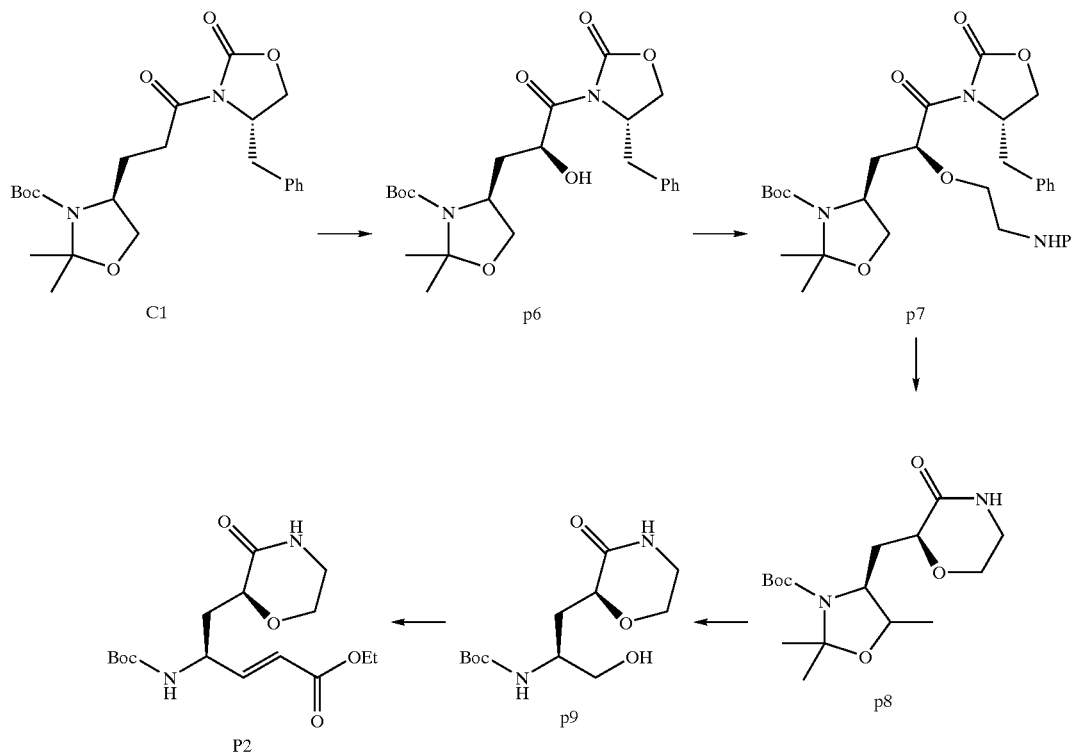

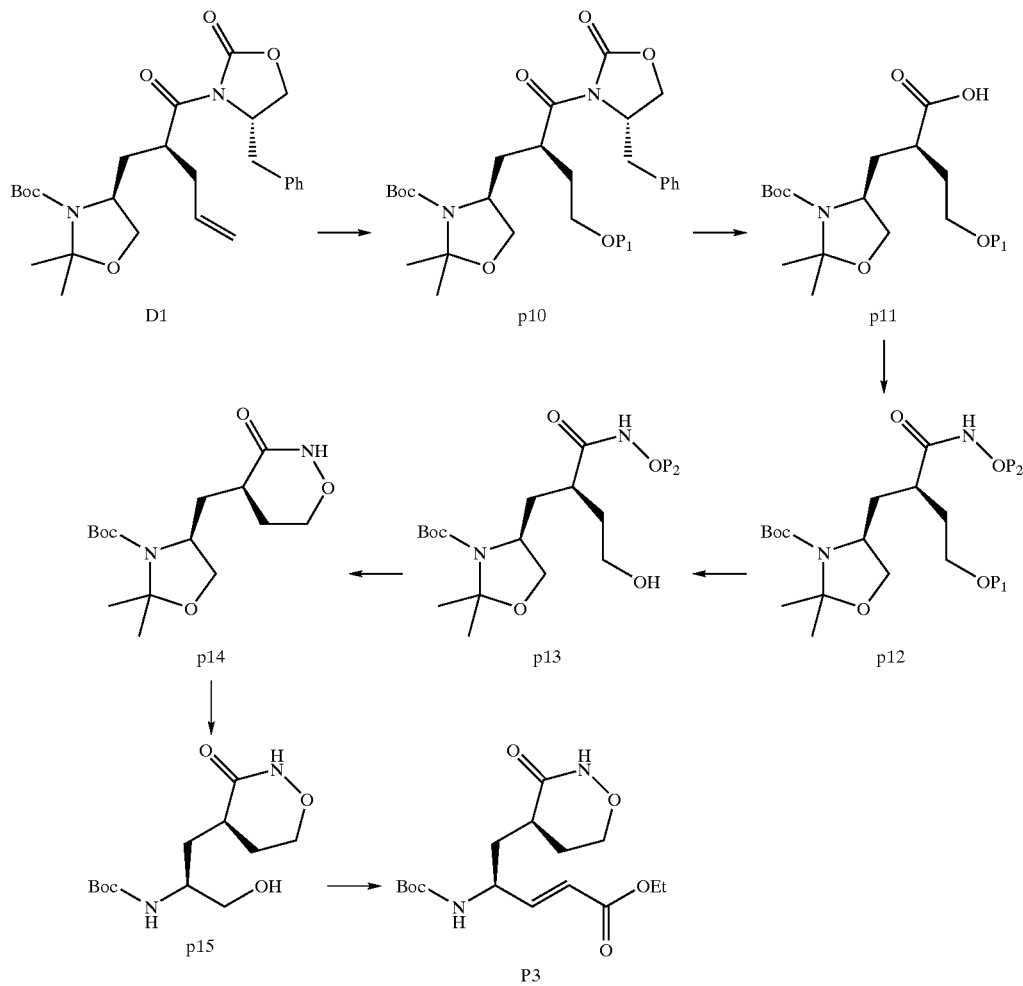

Specific Method III describes the preparation of intermediates Q1, Q2, and Q3, which may be utilized in the general methods described above. The known compound I1 is transformed into the literature molecule J1 by a modification of a published procedure (Ikuta et al., *J. Med. Chem.* 1987, vol. 30, p. 1995). Independently, the amino acid ester K1 is protected to afford silyl ether L1. The ether is reduced with DIBAL (or using other suitable reduction conditions), and the resulting aldehyde (not shown) is subjected to an olefin-forming reaction with intermediate J1, producing M1. Silyl deprotection of M1 then affords alcohol N1. This intermediate is subjected to a variety of hydrogenation conditions to provide intermediates Q1, Q2, and Q3. These intermediates may be transformed into intermediates analogous to intermediate O1 (see Specific Method I above) by oxidation and subsequent olefination.

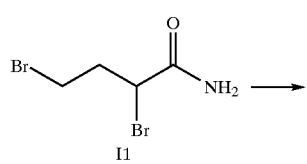

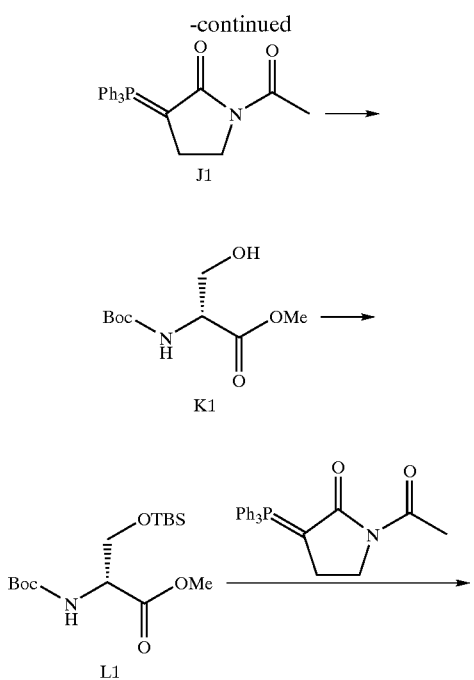

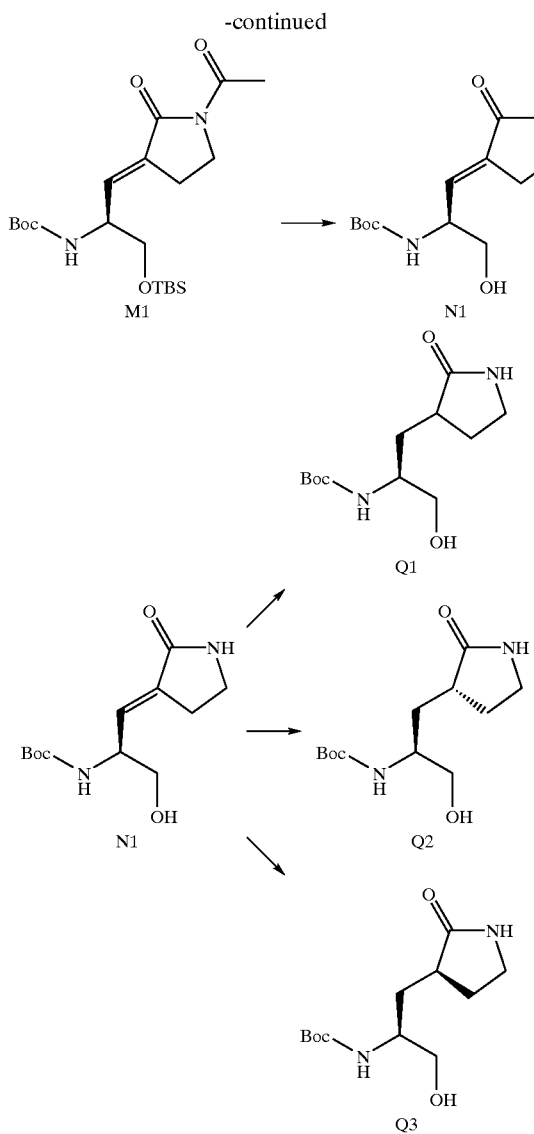

shifts are reported in parts per million (ppm, δ) downfield from an internal tetramethylsilane standard. Alternatively, ¹H NMR spectra were referenced to residual protic solvent signals as follows: $CHCl_3$=7.26 ppm; DMSO=2.49 ppm; $C_6HD_5$=7.15 ppm. Peak multiplicities are designated as follows: s=singlet; d=doublet; dd=doublet of doublets; t=triplet; q=quartet; br=broad resonance; and m=multiplet. Coupling constants are given in Hertz. Infrared absorption (IR) spectra were obtained using a Perkin-Elmer 1600 series FTIR spectrometer. Elemental microanalyses were performed by Atlantic Microlab Inc. (Norcross, Ga.) and gave results for the elements stated within ±0.4% of the theoretical values. Flash column chromatography was performed using Silica gel 60 (Merck Art 9385). Analytical thin layer chromatography (TLC) was performed using precoated sheets of Silica 60 $F_{254}$ (Merck Art 5719). Melting points (abbreviated as mp) were determined on a Mel-Temp apparatus and are uncorrected. All reactions were performed in septum-sealed flasks under a slight positive pressure of argon, unless otherwise noted. All commercial reagents were used as received from their respective suppliers with the following exceptions: tetrahydrofuran (THF) was distilled from sodium-benzophenone ketyl prior to use; dichloromethane ($CH_2Cl_2$) was distilled from calcium hydride prior to use; anhydrous lithium chloride was prepared by heating at 110° C. under vacuum overnight.

The following abbreviations are used herein: $Et_2O$ refers to diethyl ether; DMF refers to N,N-dimethylformamide; DMSO refers to dimethylsulfoxide; and MTBE refers to tert-butyl methyl ether. Other abbreviations include: $CH_3OH$ (methanol), EtOH (ethanol), EtOAc (ethyl acetate), DME (ethylene glycol dimethyl ether), Ac (acetyl), Me (methyl), Ph (phenyl), Tr (triphenylmethyl), Cbz (benzyloxycarbonyl), Boc (tert-butoxycarbonyl), TBS (tert-butyldimethylsilyl), TFA (trifluoroacetic acid), DIEA (N,N-diisopropylethylamine), DBU (1,8-diazabicyclo[5.4.0]undec-7-ene), HOBt (1-hydroxybenzotriazole hydrate), PyBOP (benzotriazole1-yl-oxy-tris-pyrrolidino-phosphonium hexafluorophosphate), HATU (O-(7-azabenzottiazol-1-yl)-N,N,N',N'-tetramethyluronium hexafluorophosphate), EDC (1-(3-dimethylaminopropyl)-3-ethylcarbarbodiimide hydrochloride), DCC (dicyclohexylcarbodiimide), DDQ (2,3-dichloro-5,6-dicyano-1,4-benzoquinone), DMAP (4-dimethylaminopyridine), Gln (glutamine), Leu (leucine), Phe (phenylalanine), Val (valine), His (histidine), 1-Naphth (1-naphthlyalanine), 2-Naphth (2-naphthylalanine), α-t-Butyl-Gly (tert-butyl glycine), (S)-Pyrrol-Ala ((2S,3'S)-2-amino-3-(2'-oxopyrrolidin-3'-yl)-propionic acid), and (S)-Piper-Ala ((2S,3'S)-2-amino-3-(2'-oxo-piperidin-3'-yl)-propionic acid). Additionally, "L" represents naturally occurring amino acids.

A simplified naming system employing amino acid abbreviations is used to identify some intermediates and final products. When naming compounds, italicized amino acid abbreviations represent modifications at the C-terminus of that residue where the following apply: (1) acrylic acid esters are reported as "E" (trans) propenoates; (2) substituted 3-methylene-dihydrofuran-2-ones are reported as "E" (trans) 2-(α-vinyl-γ-butyrolactones); and (3) 5-vinylisoxazoles are reported as "E" (trans) propenisoxazoles. In addition, the terminology "$AA_1\Psi[COCH_2]$-$AA_2$" indicates that, for any peptide sequence, two amino acids ($AA_1$ and $AA_2$) usually linked by an amide bond are replaced by a ketomethlyene dipeptide isostere moiety. The terminology "$AA_1$-$NCH_3$-$AA_2$" indicates that, for any peptide sequence, the amide bond that usually connects the two amino acids ($AA_1$ and The artisan will recognize that various compounds of the invention may be made by following the above-described general and specific methods as well as teachings in the art, including the references cited herein, the disclosures of which are hereby incorporated by reference. Additionally, the artisan may prepare various compounds of the invention according to the example described below or through routine modifications to the syntheses described herein.

EXAMPLES

Examples of various preferred compounds of formula I are set forth below. The structures of the compounds of the following examples were confirmed by one or more of the following: proton magnetic resonance spectroscopy, infrared spectroscopy, elemental microanalysis, mass spectrometry, thin layer chromatography, melting-point determination, and boiling-point determination. Where there is any discrepancy between the given structural formula shown for a compound and its chemical name provided, the structural formula applies.

Proton magnetic resonance (¹H NMR) spectra were determined using a Varian UNITYplus 300 spectrometer operating at a field strength of 300 megahertz (MHz). Chemical AA$_2$) is replaced by an N-methyl amide linkage. The terminology "AA$_1$-O-AA$_2$" indicates that, for any peptide sequence, the amide bond that usually connects the two amino acids (AA$_1$ and AA$_2$) is replaced by an ester linkage.

Examples of embodiments in accordance with the invention are described below.

Example 1

Preparation of Comparison Compound #1: 5-(3'-(Cbz-L-Leu-L-Phe-L-Gln)-E-Propene)-isoxazole (Comparison Compound #1)

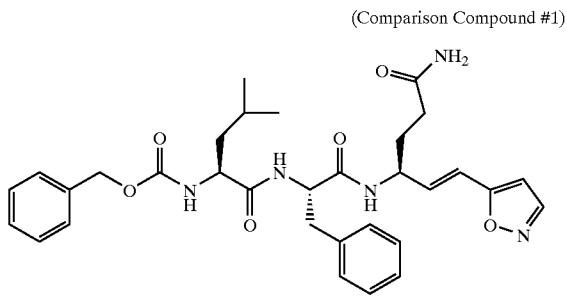

Preparation of Intermediate Cbz-L-(Tr-Gln)-OMe

Cbz-L-(Tr-Gln) (0.26 g, 0.50 mmol, 1 equiv.) was added to a solution of acetyl chloride (0.25 mL, 3.52 mmol, 7.0 equiv.) in CH$_3$OH (5 mL), and stirring was continued at 23° C. for 1 h (hour). The solvent was removed under reduced pressure, and the residue was dissolved in CH$_2$Cl$_2$ (100 mL) and washed with water (100 mL), saturated NaHCO$_3$ (100 mL), and brine (100 mL). The organic layer was dried over Na$_2$SO$_4$ and was concentrated. The residue was purified by flash column chromatography (20% EtOAc in hexanes) to afford Cbz-L-(Tr-Gln)-OMe (0.23 g, 84% yield) as a white solid: mp=139–140° C.; IR (cm$^{-1}$) 1742, 1207; $^1$H NMR (DMSO-d$_6$) δ 1.16 (t, 1H, J=7.0), 1.77 (m, 1H), 1.97 (m, 1H), 3.61 (s, 3H), 4.99 (m, 1H), 5.03 (s, 2H), 7.02–7.55 (m, 20H), 7.69 (d, 1H, J=7.7), 8.59 (s, 1H); Anal. (C$_{33}$H$_{32}$N$_2$O$_5$) C, H, N.

Preparation of Intermediate Cbz-L-(Tr-Glutaminol)

Lithium chloride (0.24 g, 5.66 mmol, 2.0 equiv.) was added to a solution of Cbz-L-(Tr-Gln)-OMe (1.50 g, 2.79 mmol, 1 equiv.) in 2:1 THF:EtOH (30 mL), and the mixture was stirred at 23° C. until all solids had dissolved (10 minutes). Sodium borohydride (0.21 g, 5.55 mmol, 2.0 equiv.) was added, and the reaction mixture was stirred overnight at 23° C. The solvents were removed under reduced pressure, the residue was taken up in water (50 mL), and the pH was adjusted to 2–3 with 10% HCl. The product was extracted with EtOAc (50 mL), and the organic layer was washed with water (50 mL) and brine (50 mL) before drying over MgSO$_4$. The organic layer was concentrated, and the residue was purified by flash column chromatography (gradient elution, 20→50% EtOAc in benzene) to give Cbz-L-(Tr-glutaminol) (1.02 g, 72% yield) as a white glassy solid: mp=66–70° C.; IR (cm$^{-1}$) 3318, 1699, 1510, 1240; $^1$H NMR (DMSO-d$_6$) δ 1.40 (m, 1H), 1.72 (m, 1H), 2.26 (m, 2H), 3.17–3.50 (m, 3H), 4.64 (t, 1H, J=5.0), 5.00 (s, 2H), 7.00–7.40 (m, 20H), 6.96 (d, 1H, J=8.5), 8.54 (s, 1H); Anal. (C$_{32}$H$_{32}$N$_2$O$_4$) C, H, N.

Preparation of Intermediate L-(Tr-Glutaminol)

A suspension of Cbz-L-(Tr-glutaminol) (1.93 g, 3.79 mmol) in CH$_3$OH (25 mL) and Pd/C (10%, 0.19 g) was stirred under a hydrogen atmosphere (balloon) for 4 hours, then was filtered through a layer of Celite. The filtrate was concentrated under reduced pressure to give L-(Tr-glutaminol) as a white amorphous solid (1.38 g, 98% yield): mp=191–193° C.; IR (cm$^{-1}$) 3255 (br), 1642, 1527; $^1$H NMR (DMSO-d$_6$) δ 1.29 (m, 1H), 1.53 (m, 1H), 2.29 (m, 2H), 3.08 (m, 1H), 3.18 (m, 2H), 3.38 (s, br, 2H), 4.43 (s, br, 1H), 7.14–7.28 (m, 15H), 8.62 (s, 1H).

Preparation of Intermediate Cbz-L-Leu-L-Phe-L-(Tr-Glutaminol)

Carbonyldiimidazole (0.17 g, 1.05 mmol, 1.0 equiv.) was added to a solution of Cbz-L-Leu-L-Phe-OH (0.41 g, 1.0 mmol, 0.95 equiv.) in THF (10 mL), and the reaction mixture was stirred at 23° C. for 1 hour. L-(Tr-Glutaminol) (0.39 g, 1.05 mmol, 1 equiv.) was then added, and the resulting solution was stirred overnight. The volatiles were removed under reduced pressure, and the residue was purified by flash column chromatography (gradient elution, 2→4% CH$_3$OH in CHCl$_3$) to give Cbz-L-Leu-L-Phe-L-(Tr-glutaminol) (0.47 g, 62% yield) as a white amorphous solid: mp=92–95° C.; IR (cm$^{-1}$) 3302, 1657, 1520, 1238; $^1$H NMR (DMSO-d$_6$) δ 0.79 (t, 6H, J=7.0), 1.30 (m, 2H), 1.44 (m, 2H), 1.75 (m, 1H), 2.22 (m, 2H), 2.82 (m, 1H), 2.97 (m, 1H), 3.14 (m, 1H), 3.25 (m, 1H), 3.63 (m, 1H), 3.95 (m, 1H), 4.48 (m, 1H), 4.65 (t, 1H, J=5.0), 4.96 (d, 1H, J=13.0), 5.02 (d, 1H, J=13.0), 7.07–7.33 (m, 25H), 7.42 (d, 1H, J=8.0), 7.66 (d, 1H, J=8.5), 7.86 (d, 1H, J=8.0), 8.52 (s, 1H); Anal. (C$_{47}$H$_{52}$N$_4$O$_6$.0.5H$_2$O) C, H, N.

Preparation of Intermediate Cbz-L-Leu-L-Phe-L-(Tr-Gln)-H o-Iodoxybenzoic acid (0.63 g, 2.25 mmol, 3.0 equiv.) was added to a solution of Cbz-L-Leu-L-Phe-L-(Tr-glutaminol) (0.58 g, 0.75 mmol, 1 equiv.) in DMSO (7.5 mL) at 23° C. After stirring for 2 hours, the DMSO was removed under reduced pressure. The residue was twice diluted with CH$_2$Cl$_2$, and the solvent evaporated to remove any remaining DMSO. The residue was diluted with EtOAc (30 mL) and filtered, and the filtrate was washed with 5% Na$_2$S$_2$O$_3$/5% NaHCO$_3$ solution (30 mL), water (30 mL), and brine (30 mL), and then dried over Na$_2$SO$_4$. The solvent was removed under reduced pressure to give Cbz-L-Leu-L-Phe-L-(Tr-Gln)-H (0.53 g, 92% yield) as a white glassy solid, which was used immediately without further purification: $^1$H NMR (DMSO-d$_6$) δ 0.79 (m, 6H), 1.00–1.98 (m, 5H), 2.27 (m, 2H), 2.84 (m, 1H), 3.02 (m, 1H), 3.98 (m, 2H), 4.58 (m, 1H), 4.99 (s, 2H), 7.14–7.32 (m, 25H), 7.39 (d, 1H, J=8.1), 7.97 (d, 1H, J=8.5), 8.38 (d, 1H, J=8.0), 8.60 (s, 1H), 9.20 (s, 1H).

Preparation of Intermediate 5-{3'-(Cbz-L-Leu-L-Phe-L-(Tr-Gln))-E-Propene}-Isoxazole A solution of KN((CH$_3$)$_3$Si)$_2$ (0.95 mL of a 0.5 M solution in THF, 0.477 mmol, 1.0 equiv.) was added to a suspension of isoxazol-5-ylmethyl-triphenylphosphonium bromide (0.222 g, 0.525 mmol, 1.1 equiv) in THF (20 mL) at 0° C., and the reaction was stirred at 0° C. for 30 minutes. A solution of Cbz-L-Leu-L-Phe-L-(Tr-Gln)-H (0.366 g, 0.477 mmol, 1 equiv.) in THF (10 mL) was added, and the reaction mixture was then stirred overnight at 23° C. The solvent was removed in vacuo, and the residue was diluted with EtOAc (30 mL), washed with water (30 mL), and then dried over MgSO$_4$. The solvent was removed under reduced pressure and the residue purified by flash silica gel chromatography (gradient elution, 0→1% CH$_3$OH in CHCl$_3$) to give 5-{3'-(Cbz-L-Leu-L-Phe-L-(Tr-Gln))-E-propene}-isoxazole (0.307 g, 70% yield) as an amorphous solid: IR (cm$^{-1}$) 3423, 1678, 1568, 1265, 1043, 711; $^1$H NMR (DMSO-d$_6$) δ 0.77–0.81 (m, 6H), 1.21–1.36 (m, 2H), 1.40–1.55 (m, 1H), 1.60–1.80 (m, 2H), 2.34–2.45 (m, 2H), 2.82–2.87 (m, 1H), 2.91–3.04 (m, 1H), 3.95–4.00 (m, 1H), 4.41–4.50 (m, 1H), 4.53–4.60 (m, 1H), 4.99 (q, 2H, J=6.0), 6.19 (d, 1H, J=15.0), 6.36 (dd, 1H, J=15.0, 6.0), 6.46 (s, 1H), 7.15–7.33 (m, 20H), 7.42 (d, 1H, J=9.0), 7.56–7.63 (m, 5H), 7.96 (d, 1H, J=9.0), 8.08 (d, 1H, J=9.0), 8.51 (s, 1H), 8.58 (s, 1H); HRMS calcd. for $C_{51}H_{53}N_5O_6$+Cs 964.3050 (M+Cs), found 964.3018.

Preparation of Product: 5-(3'-(Cbz-L-Leu-L-Phe-L-Gln)-E-Propene)-Isoxazole

Trifluoroacetic acid (1 mL) was added to a solution of 5-{3'-(Cbz-L-Leu-L-Phe-L-(Tr-Gln))-E-propene}-isoxazole (0.214 g, 0.257 mmol) in CH$_2$Cl$_2$ (10 mL), and the reaction mixture was stirred at 23° C. overnight. The solvent was removed in vacuo and the residue purified by flash silica gel chromatography (gradient elution, 0→1% CH$_3$OH in CHCl$_3$) to give 5-(3'-(Cbz-L-Leu-L-Phe-L-Gln)-E-propene)-isoxazole as a white solid (0.054 g, 36% yield): $^1$H NMR (DMSO-d$_6$) δ 0.77–0.83 (m, 6H), 1.26–1.46 (m, 2H), 1.47–1.62 (m, 1H), 1.69–1.79 (m, 2H), 2.04–2.29 (m, 2H), 2.83–2.88 (m, 1H), 2.97–3.10 (m, 1H), 3.99–4.12 (m, 1H), 4.37–4.43 (m, 1H), 4.48–4.57 (m, 1H), 5.01 (q, 2H, J=6.0), 6.20 (d, 1H, J=15.0), 6.36 (dd, 1H, J=15.0, 6.0), 6.45 (d, 1H, J=3.0), 6.75 (s, 1H), 7.14–7.29 (m, 6H), 7.31–7.40 (m, 5H), 7.45 (d, 1H, J=9.0), 8.04 (d, 1H, J=9.0), 8.07 (d, 1H, J=9.0), 8.51 (d, 1H, J=3.0); Anal. ($C_{32}H_{39}N_5O_6$) C, H, N.

Example 2

Preparation of Compound A-1: Ethyl-3-((5'-Methylisoxazole-3'-carbonyl)-L-Leu-L-Phe-L-Gln)-E-Propenoate

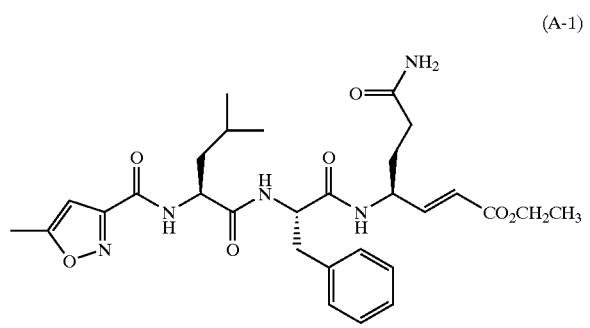

(A-1)

Preparation of Intermediate Boc-L-(Tr-Gln)-N(OMe)Me

Isobutyl chloroformate (4.77 mL, 36.8 mmol, 1.0 equiv.) was added to a solution of Boc-L-(Tr-Gln)-OH (18.7 g, 36.7 mmol, 1 equiv.) and 4-methylmorpholine (8.08 mL, 73.5 mmol, 2.0 equiv.) in CH$_2$Cl$_2$ (250 mL) at 0° C. The reaction mixture was stirred at 0° C. for 20 min. (minutes), then N,O-dimethylhydroxylamine hydrochloride (3.60 g, 36.7 mmol, 1.0 equiv.) was added. The resulting solution was stirred at 0° C. for 20 min. and at 23° C. for 2 hours (h), and then was partitioned between water (150 mL) and CH$_2$Cl$_2$ (2×150 mL). The combined organic layers were dried over Na$_2$SO$_4$, and were concentrated. Purification of the residue by flash column chromatography (gradient elution, 40→20% hexanes in EtOAc) provided Boc-L-(Tr-Gln)-N(OMe)Me (16.1 g, 82% yield) as a white foam: IR (cm$^{-1}$) 3411, 3329, 3062, 1701, 1659; $^1$H NMR (CDCl$_3$) δ 1.42 (s, 9H), 1.63–1.77 (m, 1H), 2.06–2.17 (m, 1H), 2.29–2.43 (m, 2H), 3.17 (s, 3H), 3.64 (s, 4.73 (s, br, 1H), 5.38–5.41 (m, 1H), 7.20–7.31 (m, 15H); Anal. ($C_{31}H_{37}N_3O_5$) C, H, N.

Preparation of Intermediate Boc-L-(Tr-Gln)-H

Diisobutylaluminum hydride (50.5 mL of a 1.5 M solution in toluene, 75.8 mmol, 2.5 equiv.) was added to a solution of Boc-L-(Tr-Gln)-N(OMe)Me (16.1 g, 30.3 mmol, 1 equiv.) in THF at −78° C., and the reaction mixture was stirred at −78° C. for 4 hours. Methanol (4 mL) and 1.0 M HCl (10 mL) were added sequentially, and the mixture was warmed to 23° C. The resulting suspension was diluted with Et$_2$O (150 mL), and was washed with 1.0 M HCl (3×100 mL), half-saturated NaHCO$_3$ (100 mL), and water (100 mL). The organic layer was dried over MgSO$_4$, filtered, and concentrated to give crude Boc-L-(Tr-Gln)-H (13.8 g, 97% yield) as a white solid: mp=114–116° C.; IR (cm$^{-1}$) 3313, 1697, 1494; $^1$H NMR (CDCl$_3$) δ 1.44 (s, 9H), 1.65–1.75 (m, 1H), 2.17–2.23 (m, 1H), 2.31–2.54 (m, 2H), 4.11 (s, br, 1H), 5.38–5.40 (m, 1H), 7.11 (s, 1H), 7.16–7.36 (m, 15H), 9.45 (s, 1H).

Preparation of Intermediate Ethyl-3-(Boc-L-(Tr-Gln))-E-Propenoate

Sodium bis(trimethylsilyl)amide (22.9 mL of a 1.0 M solution in THF, 22.9 mmol, 1.0 equiv.) was added to a solution of triethyl phosphonoacetate (5.59 g, 22.9 mmol, 1.0 equiv.) in THF (200 mL) at −78° C., and the resulting solution was stirred for 20 minutes at that temperature. Crude Boc-L-(Tr-Gln)-H (10.8 g, 22.9 mmol, 1 equiv.) in THF (50 mL) was added via cannula, and the reaction mixture was stirred for 2 hours at −78° C., warmed to 0° C. for 10 minutes, and then partitioned between 0.5 M HCl (150 mL) and a 1:1 mixture of EtOAc and hexanes (2×150 mL). The combined organic layers were dried over Na$_2$SO$_4$ and were concentrated. Purification of the residue by flash column chromatography (40% EtOAc in hexanes) provided ethyl-3-[Boc-L-(Tr-Gln)]-E-propenoate (10.9 g, 88% yield) as a white foam: IR (cm$^{-1}$) 3321, 1710; $^1$H NMR (CDCl$_3$) δ 1.27 (t, 3H, J=7.2), 1.42 (s, 9H), 1.70–1.78 (m, 1H), 1.80–1.96 (m, 1H), 2.35 (t, 2H, J=7.0), 4.18 (q, 2H, J=7.2), 4.29 (s, br, 1H), 4.82–4.84 (m, 1H), 5.88 (dd, 1H, J=15.7, 1.6), 6.79 (dd, 1H, J=15.7, 5.3), 6.92 (s, 1H), 7.19–7.34 (m, 15H); Anal. ($C_{33}H_{38}N_2O_5$) C, H, N.

Preparation of Intermediate Ethyl-3-(Boc-L-Phe-L-(Tr-Gln))-E-Propenoate

A solution of HCl in 1,4-dioxane (4.0 M, 15 mL), was added to a solution of ethyl-3-(Boc-L-(Tr-Gln))-E-propenoate (3.26 g, 6.01 mmol, 1 equiv.) in the same solvent (15 mL) at 23° C. After 2 h, the volatiles were removed under reduced pressure to afford ethyl-3-(H$_2$N-L-(Tr-Gln))-E-propenoate.HCl. This material was dissolved in CH$_2$Cl$_2$ (60 mL) and Boc-L-Phe-OH (1.59 g, 6.01 mmol, 1.0 equiv.), HOBt (1.22 g, 9.02 mmol, 1.5 equiv.), 4-methylmorpholine (1.98 mL, 18.03 mmol, 3 equiv.), and EDC (1.73 g, 9.02 mmol, 1.5 equiv.) were added sequentially. The reaction mixture was stirred at 23° C. overnight, and then was partitioned between water (100 mL) and CH$_2$Cl$_2$ (2×100 mL). The combined organic layers were dried over Na$_2$SO$_4$, concentrated, and the residue was purified by flash column chromatography (40% EtOAc in hexane) to afford ethyl-3-(Boc-L-Phe-L-(Tr-Gln))-E-propenoate (3.55 g, 85%) as white foam: IR (cm$^{-1}$) 3306, 1706, 1661; $^1$H NMR (CDCl$_3$) δ 1.29 (t, 3H, J=7.2), 1.38 (s, 9H), 1.65–1.76 (m, 1H), 1.87–1.99 (m, 1H), 2.25–2.27 (m, 2H), 2.94–3.01 (m, 2H), 4.14–4.26 (m, 3H), 4.48–4.53 (m, 1H), 4.95 (s, br, 1H), 5.64 (d, 1H, J=15.8), 6.29 (d, 1H, J=8.1), 6.64 (dd, 1H, J=15.8, 5.4), 6.80 (s, br, 1H), 7.14–7.32 (m, 20H); Anal. ($C_{42}H_{47}N_3O_6$) C, H, N.

Preparation of Intermediate Ethyl-3-(Boc-L-Leu-L-Phe-L-(Tr-Gln))-E-Propenoate

A solution of HCl in 1,4-dioxane (4.0 M, 15 mL) was added to a solution of ethyl-3-(Boc-L-Phe-L-(Tr-Gln))-E-propenoate (6.40 g, 9.28 mmol, 1 equiv.) in the same solvent (15 mL) at 23° C. After 2 hours, the volatiles were removed under reduced pressure. The residue was dissolved in $CH_2Cl_2$ (100 mL), and Boc-L-Leu-OH (2.58 g, 11.1 mmol, 1.2 equiv.), HOBt (1.88 g, 13.9 mmol, 1.5 equiv.), 4-methylmorpholine (3.06 mL, 27.8 mmol, 3 equiv.), and EDC (2.67 g, 13.92 mmol, 1.5 equiv.) were added sequentially. The reaction mixture was stirred at 23° C. overnight, and then was partitioned between water (100 mL) and $CH_2Cl_2$ (2×100 mL). The combined organic layers were dried over $Na_2SO_4$ and concentrated, and the residue was purified by flash column chromatography (2% $CH_3OH$ in $CH_2Cl_2$) to afford ethyl-3-(Boc-L-Leu-L-Phe-L-(Tr-Gln))-E-propenoate (6.46 g, 87% yield) as white foam: IR (cm$^{-1}$) 3284, 1651, 1515; $^1$H NMR (CDCl$_3$) δ 0.86 (d, 3H, J=6.0), 0.89 (d, 3H, J=6.0), 1.29 (t, 3H, J=7.2), 1.34 (s, 9H), 1.38–1.60 (m, 3H), 1.62–1.89 (m, 1H), 1.95–1.97 (m, 1H), 2.28–2.30 (m, 2H), 3.06–3.08 (m, 2H), 3.92–3.94 (m, 1H), 4.17 (q, 2H, J=7.2), 4.48–4.51 (m, 2H), 4.67 (m, 1H), 5.66 (d, 1H, J=15.9), 6.51–6.57 (m, 2H), 6.69 (dd, 1H, J=15.6, 5.1), 7.10–7.33 (m, 21H); Anal. ($C_{48}H_{58}N_4O_7$·0.33$H_2O$) C, H, N.

Preparation of Intermediate Ethyl-3-((5'-Methylisoxazole-3'-carbonyl)-L-Leu-L-Phe-L-(Tr-Gln))-E-Propenoate A solution of HCl in 1,4-dioxane (4.0 M, 3 mL), was added to a solution of ethyl-3-(Boc-L-Leu-L-Phe-L-(Tr-Gln))-E-propenoate (0.216 g, 0.27 mmol, 1 equiv.) in the same solvent (3 mL) at 23° C. After 2 hours, the volatiles were removed under reduced pressure. The residue was dissolved in $CH_2Cl_2$ (15 mL), cooled to 0° C., and triethylamine (0.112 mL, 0.81 mmol, 3.0 equiv.) and 5-methylisoxazole-3-carbonyl chloride (0.058 g, 0.40 mmol, 1.5 equiv.) were added sequentially. The reaction mixture was stirred at 0° C. for 30 minutes, and then was partitioned between water (50 mL) and $CH_2Cl_2$ (2×50 mL). The combined organic layers were dried over $Na_2SO_4$ and concentrated, and the residue was purified by flash column chromatography (2% $CH_3OH$ in $CH_2Cl_2$) to afford ethyl-3-((5'-methylisoxazole-3'-carbonyl)-L-Leu-L-Phe-L-(Tr-Gln))-E-propenoate (0.199 g, 91% yield) as a white foam: IR (cm$^{-1}$) 3286, 1650, 1541; $^1$H NMR (CDCl$_3$) δ 0.86 (d, 3H, J=5.4), 0.89 (d, 3H, J=5.7 ), 1.28 (t, 3H, J=7.2), 1.43–1.59 (m, 2H), 1.67–1.75 (m, 1H), 1.95–1.99 (m, 2H), 2.28 (t, 2H, J=7.2), 2.41 (s, 3H), 2.97–3.04 (m, 1H), 3.06–3.13 (m, 1H), 4.17 (q, 2H, J=7.2), 4.31–4.33 (m, 1H), 4.48–4.52 (m, 2H), 5.72 (d, 1H, J=15.9), 6.19 (s, 1H), 6.41 (d, 1H, J=7.5), 6.59 (d, 1H, J=8.1), 6.71 (dd, 1H, J=15.3, 6.0), 6.95 (d, 1H, J=6.6), 7.09–7.21 (m, 21H); Anal. ($C_{48}H_{53}N_5O_7$·$H_2O$) C, H, N.

Preparation of Product Ethyl-3-((5'-Methylisoxazole-3'-carbonyl)-L-Leu-L-Phe-L-Gln)-E-Propenoate Triisopropylsilane (0.077 mL, 0.376 mmol, 1.8 equiv.) and trifluoroacetic acid (3 mL) were added sequentially to a solution of ethyl-3-((5'-methylisoxazole-3'-carbonyl)-L-Leu-L-Phe-L-(Tr-Gln))-E-propenoate (0.185 g, 0.21 mmol, 1 equiv.) in $CH_2Cl_2$ (3 mL) at 23° C., producing a bright yellow solution. The reaction mixture was stirred for 30 minutes at 23° C., during which time it became colorless. The volatiles were removed under reduced pressure, and the resulting white solid was triturated with $Et_2O$ (10 mL), filtered, and air-dried to give ethyl-3-((5'-methylisoxazole-3'-carbonyl)-L-Leu-L-Phe-L-Gln)-E-propenoate (0.87 g, 81% yield) as white solid: mp=223–225° C.; IR (cm$^{-1}$) 3298, 1662, 1544, 1457, 1278; $^1$H NMR (DMSO-d$_6$) δ 0.81 (d, 3H, J=6.0 ), 0.85 (d, 3H, J=6.3), 1.23 (t, 3H, J=6.9), 1.38–1.42 (m, 1H), 1.48–1.77 (m, 4H), 2.04 (t, 2H, J=7.2), 2.46 (s, 3H), 2.78–2.86 (m, 1H), 2.93–3.00 (m, 1H), 4.11 (q, 2H, J=7.2), 4.36–4.54 (m, 3H), 5.63 (d, 1H, J=15.6), 6.56 (s, 1H), 6.68 (dd, 1H, J=15.9, 5.4), 6.76 (s, br, 1H), 7.19 (m, 6H), 8.09 (d, 1H, J=8.1), 8.14 (d, 1H, J=7.8), 8.58 (d, 1H, J=7.5); Anal. ($C_{29}H_{39}N_5O_7$) C, H, N.

Example 3

Preparation of Compound A-2: Ethyl-3-((Isoxazole-5'-carbonyl)-L-Leu-L-Phe-L-Gln)-E-Propenoate

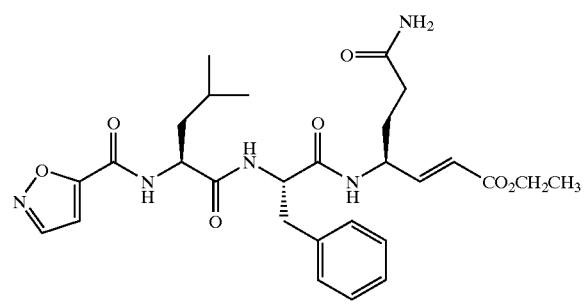

(A-2)

Preparation of Intermediate Ethyl-3-((Isoxazole-5'-carbonyl)-L-Leu-L-Phe-L-(Tr-Gln))-E-Propenoate This compound was prepared from ethyl-3-(Boc-L-Leu-L-Phe-L-(Tr-Gln))-E-propenoate and isoxazole-5-carbonyl chloride using the procedure described above (Example 2) for the preparation of ethyl-3-((5'-methylisoxazole-3'-carbonyl)-L-Leu-L-Phe-L-(Tr-Gln))-E-propenoate: IR (cm$^{-1}$) 3282, 1643, 1530; $^1$H NMR (CDCl$_3$) δ 0.87 (t, 6H, J=6.6), 1.29 (t, 3H, J=7.2), 1.49–1.64 (m, 3H), 1.69–1.80 (m, 1H), 1.90–1.96 (m, 1H), 2.30 (t, 2H, J=7.2), 2.92–2.96 (m, 1H), 3.02–3.09 (m, 1H), 4.17 (q, 2H, J=7.2), 4.42–4.48 (m, 3H), 5.69 (d, 1H, J=15.3), 6.65 (s, br, 1H), 6.66 (dd, 1H, J=15.9, 5.4), 6.76–6.79 (m, 2H), 7.00–7.31 (m, 22H), 8.24 (s, 1H); Anal. ($C_{47}H_{51}N_5O_7$·0.75$H_2O$) C, H, N.

Preparation of Ethyl-3-((Isoxazole-5'-carbonyl)-L-Leu-L-Phe-L-Gln)-E-Propenoate

The title compound was prepared from ethyl-3-((isoxazole-5'-carbonyl)-L-Leu-L-Phe-L-(Tr-Gln))-E-propenoate using a procedure analogous to that described above (Example 2) for the preparation of ethyl-3-((5'-methylisoxazole-3'-carbonyl)-L-Leu-L-Phe-L-Gln)-E-propenoate: mp=217–220° C.; IR (cm$^{-1}$) 3302, 1655, 1541; $^1$H NMR (DMSO-d$_6$) δ 0.81 (d, 3H, J=6.0), 0.86 (d, 3H, J=6.0), 1.21 (t, 3H, J=7.2), 1.42–1.75 (m, 5H), 2.04 (t, 2H, J=7.2), 2.78–2.87 (m, 1H), 2.94–3.01 (m, 1H), 4.11 (q, 2H, J=7.2), 4.37 (m, 1H), 4.41–4.52 (m, 2H), 5.64 (d, 1H, J=15.6), 6.68 (dd, 1H, J=15.9, 5.4), 6.76 (s, br, 1H), 7.12–7.19 (m, 7H), 8.02 (d, 1H, J=8.1), 8.20 (d, 1H, J=8.1), 8.74 (d, 1H, J=1.8), 8.94 (d, 1H, J=7.8); Anal. ($C_{28}H_{37}N_5O_7$) C, H, N.

Example 4

Preparation of Compound A-3: Ethyl-3-((5'-Methylisoxazole-3'-carbonyl)-L-α-(t-Butyl-Gly)-L-(4-Me-Phe)-L-Gln)-E-Propenoate (A-3)

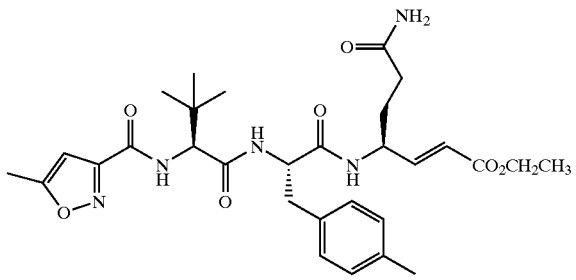

Preparation of Intermediate Ethyl-3-(Boc-L-(4-Me-Phe)-L-(Tr-Gln))-E-Propenoate

Ethyl-3-($H_2$N-L-(Tr-Gln))-E-propenoate.HCl (prepared as described in Example 2 above, 1.37 g, 3.10 mmol) was dissolved in DMF (10 mL) at 23° C. Diisopropylethylamine (1.08 mL, 6.20 mmol) was added, followed by Boc-L-(4-Me-Phe)-OH (0.87 g 3.10 mmol). The reaction was cooled to 0° C. HATU (1.18 g, 3.10 mmol) was added, and the reaction allowed to warm to room temperature. The DMF was removed in vacuo. The residue was dissolved in EtOAc (30 mL), and the organic phase was washed sequentially with 10% HCl solution (25 mL), saturated $NaHCO_3$ solution (25 mL), $H_2O$ (25 mL), and brine (25 mL). The solvent was dried ($MgSO_4$) and filtered, and the residue purified by flash column chromatography (gradient elution, 0→0.75% $CH_3OH$ in $CHCl_3$) to give ethyl-3-(Boc-L-(4-Me-Phe)-L-(Tr-Gln))-E-propenoate (1.48 g, 68% yield) as a white amorphous solid: IR ($cm^{-1}$) 1713, 1655, 1491, 1175; $^1$H NMR (DMSO-$d_6$) δ 1.20 (t, 3H, J=7.0), 1.30 (s, 9H), 1.62–1.66 (m, 2H), 2.23 (s, 3H), 2.32 (m, 2H), 2.72 (m, 1H), 2.84 (m, 1H), 4.07–4.09 (m, 1H), 4.10 (q, 2H, J=7.0), 4.38 (m, 1H), 5.64 (d, 1H, J=15.5), 6.72 (dd, 1H, J=15.5, 5.5), 6.88 (d, 1H, J=8.0), 7.04 (d, 2H, J=7.7), 7.10 (d, 2H, J=7.7), 7.14–7.28 (m, 15H), 8.02 (d, 1H, J=8.0), 8.53 (s, 1H); Anal. ($C_{43}H_{49}N_3O_6$) C, H, N.

Preparation of Intermediate Ethyl-3-(Boc-L-α-(t-Butyl-Gly)-L-(4-Me-Phe)-L-(Tr-Gln))-E-Propenoate Ethyl-3-(Boc-L-(4-Me-Phe)-L-(Tr-Gln))-E-propenoate (1.45 g, 2.06 mmol) was dissolved in 1,4-dioxane (27 mL), and a solution of HCl in 1,4-dioxane (4.0 M, 14 mL) was added. The reaction was stirred at room temperature for 4 hours. The solvent was removed by evaporation, and the residue taken up in EtOAc (50 mL). The organic phase was washed with saturated $NaHCO_3$ solution (50 mL) and then brine (50 mL), dried ($MgSO_4$), and the solvent removed under reduced pressure to give 1.23 g of an off-white amorphous solid. This material was coupled with Boc-L-α-(t-Butyl-Gly)-OH using the procedure described for the synthesis of ethyl-3-(Boc-L-(4-Me-Phe)-L-(Tr-Gln))-E-propenoate above to afford ethyl-3-(Boc-L-α-(t-Butyl-Gly)-L-(4-Me-Phe)-L-(Tr-Gln))-E-propenoate (49% yield) as a white amorphous solid: IR ($cm^{-1}$) 1655, 1507, 1248, 1171; $^1$H NMR (DMSO-$d_6$) δ 0.81 (s, 9H), 1.21 (t, 3H, J=7.0), 1.37 (s, 9H), 1.52–1.70 (m, 2H), 2.22 (s, 3H), 2.26–2.28 (m, 2H), 2.73–2.91 (m, 2H), 3.86 (d, 1H, J=9.6), 4.05–4.14 (m, 2H), 4.31–4.36 (m, 1H), 4.47–4.55 (m, 1H), 5.54 (d, 1H, J=15.4), 6.37 (d, 1H, J=9.6), 6.65 (dd, 1H, J=15.8, 5.5), 7.01 (d, 2H, J=8.1), 7.07 (d, 2H, J=7.7), 7.11–7.32 (m, 15H), 8.03 (d, 1H, J=8.1), 8.10 (d, 1H, J=7.7), 8.49 (s, 1H); Anal. ($C_{49}H_{60}N_4O_7$·0.4$H_2O$) C, H, N.

Preparation of Intermediate Ethyl-3-((5'-Methylisoxazole-3'-carbonyl)-L-α-(t-Butyl-Gly)-L-(4-Me-Phe)-L-(Tr-Gln))-E-Propenoate Ethyl-3-(Boc-L-α-(t-Butyl-Gly)-L-(4-Me-Phe)-L-(Tr-Gln))-E-propenoate was deprotected using the procedure described for the deprotection of ethyl-3-(Boc-L-(4-Me-Phe)-L-(Tr-Gln))-E-propenoate above, and the resulting amine (0.22 g, 0.30 mmol) was dissolved in $CH_2Cl_2$ (3 mL). Pyridine (0.025 mL, 0.32 mmol) was added, and the reaction was cooled to 0° C. 5-Methylisoxazole-3-carbonyl chloride (0.046 g, 0.32 mmol) was added. The reaction was allowed to warm to room temperature, and was stirred for one hour. The solvent was removed in vacuo, and the residue subjected to flash column chromatography (gradient elution, 0→1% $CH_3OH$ in $CH_2Cl_2$) to afford ethyl-3-((5'-methylisoxazole-3'-carbonyl)-L-α-(t-Butyl-Gly)-L-(4-Me-Phe)-L-(Tr-Gln))-E-propenoate (0.19 g, 77% yield) as a white amorphous solid: IR ($cm^{-1}$) 1651, 1518; $^1$H NMR (DMSO-$d_6$) δ 0.88 (s, 9H), 1.20 (t, 3H, J=7.0), 1.55–1.67 (m, 2H), 2.14 (s, 3H), 2.18–2.28 (m, 2H), 2.45 (s, 3H), 2.70–2.77 (m, 1H), 2.86–2.93 (m, 1H), 4.07–4.14 (m, 2H), 4.46 (d, 1H, J=9.6), 4.50–4.55 (m, 1H), 5.54 (d, 1H, J=15.8), 6.59 (s, 1H), 6.65 (dd, 1H, J=15.8, 5.5, 15.8), 6.95 (d, 2H, J=8.1), 7.05 (d, 2H, J=8.1), 7.13–7.28 (m, 15H), 7.60 (d, 1H, J=9.6), 8.13 (d, 1H, J=8.1), 8.41 (d, 1H, J=8.1), 8.51 (s, 1H); Anal. ($C_{49}H_{55}N_5O_7$) C, H, N.

Preparation of Product Ethyl-3-((5'-Methylisoxazole-3'-carbonyl)-L-α-(t-Butyl-Gly)-L-(4-Me-Phe)-L-Gln)-E-Propenoate Ethyl-3-((5'-methylisoxazole-3'-carbonyl)-L-α-(t-Butyl-Gly)-L-(4-Me-Phe)-L-(Tr-Gln))-E-propenoate (0.17 g, 0.20 mmol) was dissolved in $CH_2Cl_2$ (4 mL) at 23° C. Trifluoroacetic acid (0.4 mL) was added, and the reaction was stirred at room temperature for six hours. The solvents were removed in vacuo, and the residue was subjected to flash column chromatography (gradient elution, 0→2% $CH_3OH$ in $CH_2Cl_2$) to afford ethyl-3-((5'-methylisoxazole-3'-carbonyl)-L-α-(t-Butyl-Gly)-L-(4-Me-Phe)-L-Gln)-E-propenoate (0.085 g, 73% yield) as a white amorphous solid: IR ($cm^{-1}$) 1661, 1541, 1206; $^1$H NMR (DMSO-$d_6$) δ 0.88 (s, 9H), 1.21 (t, 3H, J=7.0), 1.60–1.73 (m, 2H, 2.01–2.06 (m, 2H), 2.14 (s, 3H), 2.50 (s, 3H), 2.70–2.77 (m, 1H), 2.86–2.93 (m, 1H), 4.07–4.14 (m, 2H), 4.34–4.37 (m, 1H), 4.45 (d, 1H, J=9.6), 4.50–4.55 (m, 1H), 5.57 (d, 1H, J=15.8), 6.60 (s, 1H), 6.66 (dd, 1H, J=15.8, 5.5), 6.75 (s, br, 1H), 6.96 (d, 2H, J=8.1), 7.06 (d, 2H, J=7.7), 7.17 (s, br, 1H), 7.65 (d, 1H, J=9.6), 8.14 (d, 1H, J=8.1), 8.40 (d, 1H, J=7.7); Anal. ($C_{30}H_{41}N_5O_7$·0.5TFA·0.5$H_2O$) C, H, N.

Example 5

Preparation of Compound A-4: Ethyl-3-((5'-Methylisoxazole-3'-carbonyl)-L-α-(t-Butyl-Gly)-L-(4-F-Phe)-L-Gln)-E-Propenoate

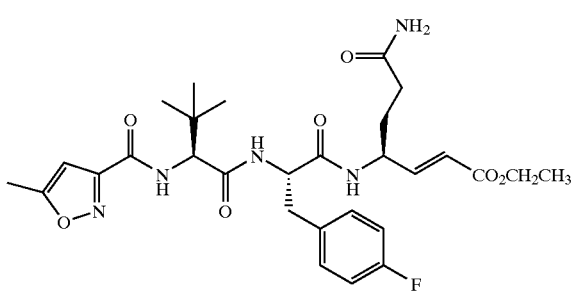

(A-4)

Preparation of Intermediate Ethyl-3-(Boc-L-(4-F-Phe)-L-(Tr-Gln))-E-Propenoate Boc-L-(4-F-Phe)-OH (1.41 g, 5.0 mmol) was dissolved in THF (50 mL). Ethyl-3-(H$_2$N-L-(Tr-Gln))-E-propenoate.HCl (prepared as described in Example 2 above, 1.0 g, 5.0 mmol) was added, followed by Et$_3$N (0.70 mL, 5.0 mmol). Carbonyldiimidazole (0.81 g, 5.0 mmol) was added, and the reaction was stirred at room temperature for 20 hours. The solvent was removed in vacuo, and the residue subjected to flash column chromatography (gradient elution, 0→1% CH$_3$OH in CH$_2$Cl$_2$) to afford ethyl-3-(Boc-L-(4-F-Phe)-L-(Tr-Gln))-E-propenoate (1.13 g, 32% yield) as a white amorphous solid: IR (cm$^{-1}$) 1712, 1666, 1510, 1169; $^1$H NMR (DMSO-d$_6$) δ 1.20 (t, 3H, J=7.0), 1.29 (s, 9H), 1.61–1.70 (m, 2H), 2.27–2.34 (m, 2H), 2.74–2.78 (m, 1H), 2.86–2.90 (m, 1H), 4.06–4.13 (m, 3H), 4.36–4.40 (m, 1H), 5.58 (d, 1H, J=15.6), 6.71 (dd, 1H, J=15.6, 5.5), 6.98 (d, 1H, J=8.1), 7.03–7.09 (m, 2H), 7.14–7.28 (m, 17H), 8.06 (d, 1H, J=8.1), 8.53 (s, 1H); LRMS (M+Na) 730.

Preparation of Intermediate Ethyl-3-(Boc-L-α-(t-Butyl-Gly)-L-(4-F-Phe)-L-(Tr-Gln))-E-Propenoate Ethyl-3-(Boc-L-(4-F-Phe)-L-(Tr-Gln))-E-propenoate was deprotected and coupled with Boc-L-α-(t-Butyl-Gly)-OH using the procedures described above to prepare ethyl-3-(Boc-L-α-(t-Butyl-Gly)-L-(4-Me-Phe)-L-(Tr-Gln))-E-propenoate, to provide ethyl-3-(Boc-L-α-(t-Butyl-Gly)-L-(4-F-Phe)-L-(Tr-Gln))-E-propenoate (54% yield) as a white amorphous solid: IR (cm$^{-1}$) 1720, 1651, 1506, 1168; $^1$H NMR (DMSO-d$_6$) δ 0.80 (s, 9H), 1.20 (t, 3H, J=7.0), 1.36 (s, 9H), 1.53–1.67 (m, 2H), 2.23–2.28 (m, 2H), 2.79–2.94 (m, 2H), 3.85 (d, 1H, J=9.9), 4.09 (q, 2H, J=7.0), 4.31–4.35 (m, 1H), 4.53–4.55 (m, 1H), 5.46 (d, 1H, J=15.8), 6.36 (d, 1H, J=9.2), 6.64 (dd, 1H, J=15.8, 5.5), 6.97–7.03 (m, 2H), 7.13–7.28 (m, 17H), 8.08 (d, 1H, J=8.1), 8.14 (d, 1H, J=8.1), 8.49 (s, 1H); Anal. (C$_{48}$H$_{57}$N$_4$O$_7$F) C, H, N.

Preparation of Intermediate Ethyl-3-((5'-Methylisoxazole-3'-carbonyl)-L-α-(t-Butyl-Gly)-L-(4-F-Phe)-L-(Tr-Gln))-E-Propenoate Ethyl-3-(Boc-L-α-(t-Butyl-Gly)-L-(4-F-Phe)-L-(Tr-Gln))-E-propenoate was deprotected and coupled with 5-methylisoxazole-3-carbonyl chloride using the procedures described above to prepare ethyl-3-((5'-methylisoxazole-3'-carbonyl)-L-α-(t-Butyl-Gly)-L-(4-Me-Phe)-L-(Tr-Gln))-E-propenoate to afford ethyl-3-((5'-methylisoxazole-3'-carbonyl)-L-α-(t-Butyl-Gly)-L-(4-F-Phe)-L-(Tr-Gln))-E-propenoate (74% yield) as a white amorphous solid: IR (cm$^{-1}$) 1659, 1535, 1510; $^1$H NMR (DMSO-d$_6$) δ 0.88 (s, 9H), 1.20 (t, 3H, J=7.4), 1.52–1.67 (m, 2H), 2.23–2.28 (m, 2H), 2.45 (s, 3H), 2.75–2.82 (m, 1H), 2.89–2.96 (m, 1H), 4.09 (q, 2H, J=7.0), 4.32–4.36 (m, 1H), 4.45 (d, 1H, J=9.6), 4.50–4.55 (m, 1H), 5.44 (d, 1H, J=15.6), 6.58 (s, 1H), 6.63 (dd, 1H, J=15.6, 5.5, 15.6), 6.93–6.99 (m, 2H), 7.13–7.28 (m, 17H), 7.64 (d, 1H, J=9.6), 8.16 (d, 1H, J=8.5), 8.46 (d, 1H, J=8.1), 8.51 (s, 1H); Anal. (C$_{48}$H$_{52}$N$_5$O$_7$F) C, H, N.

Preparation of Ethyl-3-((5'-Methylisoxazole-3'-carbonyl)-L-α-(t-Butyl-Gly)-L-(4-F-Phe)-L-Gln)-E-Propenoate Ethyl-3-[(5'-methylisoxazole-3'-carbonyl)-L-α-(t-Butyl-Gly)-L-(4-F-Phe)-L-(Tr-Gln)]-E-propenoate was deprotected using a procedure analogous to that described above for the preparation of ethyl-3-((5'-methylisoxazole-3'-carbonyl)-L-α-(t-Butyl-Gly)-L-(4-Me-Phe)-L-Gln)-E-propenoate to provide ethyl-3-((5'-methylisoxazole-3'-carbonyl)-L-α-(t-Butyl-Gly)-L-(4-F-Phe)-L-Gln)-E-propenoate (80% yield) as a white amorphous solid: IR (cm$^{-1}$) 1653, 1543, 1223; $^1$H NMR (DMSO-d$_6$) δ 0.88 (s, 9H), 1.21 (t, 3H, J=7.0), 1.59–1.75 (m, 2H), 2.01–2.06 (m, 2H), 2.46 (s, 3H), 2.75–2.82 (m, 1H), 2.89–2.96 (m, 1H), 4.09 (q, 2H, J=7.0), 4.33–4.36 (m, 1H), 4.44 (d, 1H, J=9.6), 4.50–4.58 (m, 1H), 5.47 (d, 1H, J=15.8), 6.59 (s, 1H), 6.64 (dd, 1H, J=15.8, 5.5), 6.75 (s, br, 1H), 6.94–7.00 (m, 2H), 7.16 (s, br, 1H), 7.18–7.23 (m, 2H), 7.69 (d, 1H, J=9.6), 8.16 (d, 1H, J=8.1), 8.44 (d, 1H, J=8.1); Anal. (C$_{29}$H$_{38}$N$_5$O$_7$F) C, H, N.

Example 6

Preparation of Compound A-5: Ethyl-3-{(5'-Methylisoxazole-3'-carbonyl)-L-Val-L-(4-F-Phe)-L-((S)-Pyrrol-Ala)}-E-Propenoate

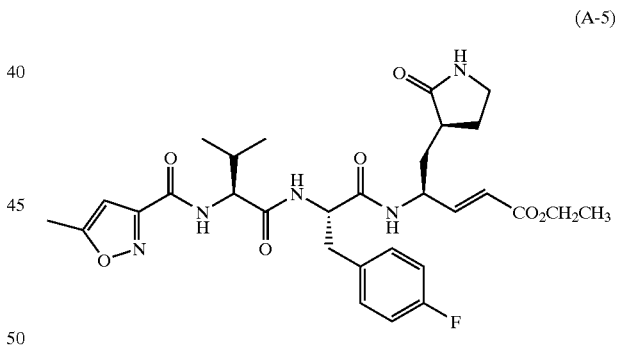

(A-5)

Preparation of Intermediate (4S)-4-(2'-Carboxyethyl)-2,2-dimethyloxazolidine-3-carboxylic Acid tert-Butyl Ester Sodium hydroxide (27 mL of a 4.0 M solution in H$_2$O, 108 mmol, 3.0 equiv.) was added to a solution of (4S)-4-(2-methoxycarbonylethyl)-2,2-dimethyl-oxazolidine-3-carboxylic acid tert-but ester (prepared as described in Chida et al., *J. Chem. Soc., Chem. Commun.* 1992, 1064) (10.5 g, 36.5 mmol, 1 equiv.) in CH$_3$OH (150 mL), and the resulting cloudy reaction mixture was stirred at 23° C. for 3.5 h. The mixture was concentrated under reduced pressure to ~30 mL volume, and then was partitioned between 0.5 M HCl (150 mL) and EtOAc (2×150 mL). The combined organic layers were dried over MgSO$_4$ and were gravity filtered. The filtrate was concentrated under reduced pressure and the residue dried under vacuum, to afford (4S)-4-(2'-carboxyethyl)-2,2-dimethyloxazolidine-3-carboxylic acid tert-butyl ester (10.0 g, 100% crude yield). This material was used without further purification: 1H NMR (CDCl$_3$, mixture of rotamers) δ 1.49 (s), 1.57 (s), 1.60 (s), 1.84–2.05 (m), 2.39–2.41 (m), 3.71–3.74 (m), 3.91–4.05 (m).

Preparation of Intermediate (4S,4"S)-4-{3'-(4"-Benzyl-2"-oxo-oxazolidin-3"-yl)-3'-oxopropyl}-2,2-dimethyloxazolidine-3-carboxylic Acid tert-Butyl Ester Triethylamine (8.87 mL, 63.6 mmol, 3.0 equiv.) and pivaloyl chloride (2.61 mL, 21.2 mmol, 1.0 equiv.) were added sequentially to a solution of (4S)-4-(2'-carboxyethyl)-2,2-dimethyloxazolidine-3-carboxylic acid tert-butyl ester (5.80 g, 21.2 mmol, 1 equiv.) in THF (450 mL) at 0° C. The cloudy reaction mixture was stirred at 0° C. for 3.5 h, then lithium chloride (0.988 g, 23.3 mmol, 1.1 equiv.) and (S)-(−)-4-benzyl-2-oxazolidinone (3.57 g, 20.1 mmol, 0.95 equiv.) were added sequentially. After warming to 23° C. and stirring for 19 h, the reaction mixture was partitioned between 0.5 M HCl (150 mL) and EtOAc (2×150 mL). The combined organic layers were washed with half-saturated Na$_2$CO$_3$ (150 mL), dried over MgSO$_4$, and gravity filtered. The filtrate was concentrated under reduced pressure and the residue was purified by flash column chromatography (30% EtOAc in hexanes) to give (4S,4"S)-4-{3'-(4"-benzyl-2"-oxo-oxazolidin-3"-yl)-3'-oxopropyl}-2,2-dimethyloxazolidine-3-carboxylic acid tert-butyl ester (7.17 g, 83%) as a colorless oil: IR (cm$^{-1}$) 2978, 1783, 1694; $^1$H NMR (CDCl$_3$, mixture of rotamers) δ 1.49 (s), 1.59 (s), 1.63 (s), 2.01–2.10 (m), 2.76 (dd, J=13.5, 9.8), 2.82–3.13 (m), 3.30–3.41 (m), 3.76–3.82 (m), 3.90 (s, br), 3.97 (dd, J=9.0, 5.6), 4.10–4.19 (m), 4.63–4.71 (m), 7.22–7.36 (m); Anal. (C$_{23}$H$_{32}$N$_2$O$_6$) C, H, N.

Preparation of Intermediate (2'S,4S,4"S)-4-{2'-(4"-Benzyl-2"-oxo-oxazolidine-3"-carbonyl)-pent-4'-enyl}-2,2-dimethyloxazolidine-3-carboxylic Acid tert-Butyl Ester A solution of (4S,4"S)-4-{3'-(4"-benzyl-2"-oxo-oxazolidin-3"-yl)-3'-oxopropyl}-2,2-dimethyloxazolidine-3-carboxylic acid tert-butyl ester (7.17 g, 16.6 mmol, 1 equiv.) in THF (50 mL) was added to a solution of sodium bis(trimethylsilyl)amide (16.6 mL of a 1.0 M solution in THF, 16.6 mmol, 1.0 equiv.) in the same solvent (150 mL) at −78° C. The reaction mixture was stirred for 20 min. at −78° C., and then allyl iodide (4.55 mL, 49.8 mmol, 3.0 equiv.) was added. After stirring an additional 3 h at −78° C., the reaction mixture was maintained at −45° C. for 2 h, and then was partitioned between a 2:1 mixture of half-saturated NH$_4$Cl and 5% Na$_2$S$_2$O$_3$ (300 mL) and a 1:1 mixture of EtOAc and hexanes (2×200 mL). The combined organic layers were washed with H$_2$O (200 mL), dried over MgSO$_4$, and gravity filtered. The filtrate was concentrated under reduced pressure and the residue was purified by flash column chromatography (15% EtOAc in hexanes) to provide (2'S,4S,4"S)-4-{2'-(4"-benzyl-2"-oxo-oxazolidine-3"-carbonyl)-pent-4'-enyl}-2,2-dimethyloxazolidine-3-carboxylic acid tert-butyl ester (4.29 g, 55%) as a colorless oil: IR (cm$^{-1}$) 2978, 1780, 1695; $^1$H NMR (CDCl$_3$, mixture of rotamers) δ 1.45 (s), 1.49 (s), 1.68–1.80 (m), 2.13–2.47 (m), 2.49–2.67 (m), 3.32 (dd, J=13.4, 3.1), 3.69–3.97 (m), 4.11–4.21 (m), 4.66–4.74 (m), 5.06–5.13 (m), 5.74–5.88 (m), 7.20–7.36 (m); Anal. (C$_{26}$H$_{36}$N$_2$O$_6$) C, H, N.

Preparation of Intermediate (1S,3S)-{3-(1'-(2",4"-Dimethoxybenzyl)-2'-oxo-pyrrolidin-3'-yl)-1-hydroxymethylpropyl}-carbamic Acid tert-Butyl Ester Ozone was bubbled through a solution of (2'S,4S,4"S)-4-(2'-(4"-benzyl-2"-oxo-oxazolidine-3"-carbonyl)-pent-4'-enyl)-2,2-dimethyloxazolidine-3-carboxylic acid tert-butyl ester (4.29 g, 9.08 mmol, 1 equiv.) in CH$_2$Cl$_2$ (200 mL) and CH$_3$OH (0.735 mL, 18.1 mmol, 2.0 equiv.) at −78° C. until a blue color persisted. The reaction mixture was then purged with argon until it became colorless. Methyl sulfide (6.67 mL, 90.8 mmol, 10 equiv.) was added, the mixture was stirred at −78° C. for 3.5 h, and was maintained at 0° C. for an additional 1 h. After partitioning the reaction mixture between H$_2$O (200 mL) and a 1:1 mixture of EtOAc and hexanes (2×200 mL), the combined organic layers were dried over MgSO$_4$ and gravity filtered. The filtrate was concentrated under reduced pressure and the residue was immediately utilized without further purification.

The above residue was dissolved in a 2:1 mixture of THF and EtOH (240 mL) at 23° C., and 2,4-dimethoxybenzylamine hydrochloride (7.40 g, 36.3 mmol, 4.0 equiv.), sodium acetate (2.98 g, 36.2 mmol, 4.0 equiv.), and sodium cyanoborohydride (1.14 g, 18.1 mmol, 2.0 equiv.) were added sequentially. The resulting suspension was stirred for 18 h at 23° C., and then was partitioned between 0.5 M HCl (400 mL) and EtOAc (2×200 mL). The combined organic layers were washed with half-saturated NaHCO$_3$ (300 mL), dried over Na$_2$SO$_4$, and concentrated under reduced pressure. The residue was passed through a short silica gel column (eluting with 50% EtOAc in hexanes) to give (3'S,4S)-4-{1'-(2",4"-dimethoxybenzyl)-2'-oxo-pyrrolidin-3'-ylmethyl}-2,2-dimethyl-oxazolidine-3-carboxylic acid tert-butyl ester contaminated with (S)-(−)-4-benzyl-2-oxazolidinone.

This material was dissolved in CH$_3$OH (100 mL), and TsOH.H$_2$O (0.345 g, 1.81 mmol, 0.20 equiv.) was added. The reaction mixture was heated to 50° C., and was maintained at that temperature for 2.5 h. After cooling to 23° C., the reaction mixture was concentrated under reduced pressure to ~20 mL volume and was partitioned between half-saturated NaHCO$_3$ (150 mL) and a 9:1 mixture of CH$_2$Cl$_2$ and CH$_3$OH (2×150 mL). The combined organic layers were dried over Na$_2$SO$_4$ and concentrated under reduced pressure. Purification of the residue by flash column chromatography (3% CH$_3$OH in CH$_2$Cl$_2$) afforded (1S,3'S)-{2-(1'-(2",4"-dimethoxybenzyl)-2'-oxo-pyrrolidin-3'-yl)-1-hydroxymethylethyl}-carbamic acid tert-butyl ester (1.62 g, 44%) as a foam: IR (cm$^{-1}$) 3328, 1669; $^1$H NMR (CDCl$_3$) δ 1.44 (s, 9H), 1.50–1.75 (m, 2H), 1.90–2.00 (m, 1H), 2.17–2.27 (m, 1H), 2.52–2.62 (m, 1H), 3.14–3.24 (m, 2H), 3.51–3.65 (m, 3H), 3.70–3.78 (m, 1H), 3.80 (s, 6H), 4.35 (d, 1H, J=14.3), 4.48 (d, 1H, J=14.3), 5.51–5.54 (m, 1H), 6.42–6.46 (m, 2H), 7.09–7.12 (m, 1H); Anal. (C$_{21}$H$_{32}$N$_2$O$_6$) C, H, N.

Preparation of Intermediate Ethyl-3-{Boc-L-((N-2,4-Dimethoxybenzyl)-(S)-Pyrrol-Ala])-E-Propenoate DMSO (0.270 mL, 3.80 mmol, 3 equiv. was added dropwise to a −78° C. solution of oxalyl chloride (0.166 mL, 1.90 mmol, 1.5 equiv.) in CH$_2$Cl$_2$ (14 mL). The reaction mixture was stirred 20 min., then a solution of (1S,3'S)-{2-(1'-(2"-dimethoxybenzyl)-2'-oxo-pyrrolidin-3'-yl)-1-hydroxymethylethyl}-carbamic acid tert-butyl ester (0.518 g, 1.27 mmol, 1 equiv.) in CH$_2$Cl$_2$ (13 mL) was added via cannula along the side of the reaction vessel. After stirring 20 min., triethylamine (1.06 mL, 7.60 mmol, 6 equiv.) was added dropwise, and the reaction mixture was stirred for 1.5 h. Acetic acid (0.479 mL, 8.37 mmol, 6.6 equiv.) was added, and the reaction mixture was warmed to 0° C. for 5 min., then diluted with MTBE (200 mL) and washed with water, saturated NaHCO$_3$, and brine (25 mL each). The organic phase was dried over Na$_2$SO$_4$ and concentrated to provide the crude aldehyde as a foam (0.516 g, quant.), which was used without further purification.

Sodium bis(trimethylsilyl)amide (1.23 mL of a 1.0 M solution in TEF, 1.23 mmol, 1 equiv.) was added to a solution of triethyl phosphonoacetate (0.244 mL, 1.23 mmol, 1 equiv.) in THF (15 mL) at −78° C., and the resulting solution was stirred for 20 min. at that temperature. The crude aldehyde (prepared above, 0.500 g, 1.23 mmol, 1 equiv.) in THF (13 mL) was added via cannula along the side of the reaction vessel, and the reaction mixture was stirred for 45 min. at −78° C., warmed to 0° C. for 7 min., and partitioned between 0.5 M HCl (20 mL) and MTBE (2×50 mL). The combined organic layers were dried over $MgSO_4$ and were concentrated. Purification of the residue by flash column chromatography (60% EtOAc in hexanes) provided ethyl-3-{Boc-L-((N-2,4-dimethoxybenzyl)-(S)-pyrrol-Ala)}-E-propenoate (0.356 g, 61%) as a white foam: $R_f$=0.43 (60% EtOAc in hexanes); IR (cm$^{-1}$) 3307, 1708, 1678; $^1$H NMR (CDCl$_3$) δ 1.28 (t, 3H, J=7.2), 1.43 (s, 9H), 1.52–1.70 (m, 2H), 1.98–2.09 (m, 1H), 2.21–2.34 (m, 1H), 2.48–2.59 (m, 1H), 3.16–3.24 (m, 2H), 3.80 (s, 6H), 4.18 (q, 2H, J=7.2), 4.27–4.40 (m, 1H), 4.41 (s, 2H), 5.40 (d, 1H, J=8.1), 5.95 (dd, 1H, J=15.6, 1.6), 6.41–6.48 (m, 2H), 6.86 (dd, 1H, J=15.6, 5.3), 7.08–7.13 (m, 1H); Anal. ($C_{25}H_{36}N_2O_7 \cdot 0.25H_2O$) C, H, N.

Preparation of Intermediate Ethyl-3-{Boc-L-(4-F-Phe)-L-((N-2,4-Dimethoxybenzyl)-(S)-Pyrrol-Ala)}-E-Propenoate This material was prepared from ethyl-3-{Boc-L-((N-2,4-dimethoxybenzyl)-(S)-pyrrol-Ala)}-E-propenoate and Boc-L-(4-F-Phe)-OH using a procedure similar to that described for the preparation of ethyl-3-(Boc-L-(4-Me-Phe)-L-(Tr-Gln))-E-propenoate (Example 4) above: $R_f$=0.34 (60% EtOAc in hexanes); IR (cm$^{-1}$) 3258, 1705, 1666; $^1$H NMR (CDCl$_3$) δ 1.28 (t, 3H, J=7.2), 1.45 (s, 9H), 1.51–1.66 (m, 2H), 1.78–1.90 (m, 1H), 2.06–2.23 (m, 2H), 2.99 (dd, 1H, J=13.7, 6.2), 3.11 (dd, 1H, J=13.7, 5.3), 3.17–3.23 (m, 2H), 3.80 (s, 3H), 3.81 (s, 3H), 4.18 (q, 2H, J=7.2), 4.35 (s, 2H), 4.38–4.51 (m, 2H), 5.29–5.37 (m, 1H), 5.76 (d, 1H, J=15.8), 6.43–6.47 (m, 2H), 6.72 (dd, 1H, J=15.8, 5.3), 6.83–6.91 (m, 2H), 7.09–7.17 (m, 3H), 7.92 (br, 1H); Anal. ($C_{34}H_{44}FN_3O_8$) C, H, N.

Preparation of Intermediate Ethyl-3-{Boc-L-Val-L-(4-F-Phe)-L-[(N-2,4-Dimethoxybenzyl)-(S)-Pyrrol-Ala]}-E-Propenoate This compound was prepared from ethyl-3-{Boc-L-(4-F-Phe)-L-((N-2,4-dimethoxybenzyl)-(S)-Pyrrol-Ala)}-E-propenoate and Boc-L-Val-OH using a similar procedure to that described above for the preparation of ethyl-3-(Boc-L-Phe-L-(Tr-Gln))-E-propenoate (Example 2): $R_f$=0.24 (60% EtOAc in hexanes); IR (cm$^{-1}$) 3284, 1713, 1678 br, 1643; $^1$H NMR (CDCl$_3$) δ 0.91 (d, 3H, J=6.8), 0.97 (d, 3H, J=6.8), 1.28 (t, 3H, J=7.2), 1.45 (s, 9H), 1.50–1.62 (m, 2H), 1.66–1.82 (m, 1H), 1.90–2.02 (m, 1H), 2.08–2.21 (m, 2H), 2.94 (dd, 1H, J=13.5, 5.8), 3.17–3.27 (m, 3H), 3.80(s, 3H), 3.82 (s, 3H), 3.97–4.05 (m, 1H), 4.17 (q, 2H, J=7.2), 4.27 (d, 1H, J=14.3), 4.29–4.38 (m, 1H), 4.40 (d, 1H, J=14.3), 4.86–4.93 (m, 1H), 5.10 (d, 1H, J=8.7), 5.76 (dd, 1H, J=15.6, 1.2), 6.45–6.52 (m, 2H), 6.70 (dd, 1H, J=15.6, 5.4), 6.79–6.88 (m, 3H), 7.12–7.22 (m, 3H), 8.30 (d, 1H, J=5.9); Anal. ($C_{39}H_{53}FN_4O_9$) C, H, N.

Preparation of Intermediate Ethyl-3-{(5'-Methylisoxazole-3'-carbonyl)-L-Val-L-(4-F-Phe)-L-((N-2,4-Dimethoxybenzyl)-(S)-Pyrrol-Ala)}-E-Propenoate This compound was prepared from ethyl-3-{Boc-L-Val-L-(4-F-Phe)-L-((N-2,4-dimethoxybenzyl)-(S)-Pyrrol-Ala)}-E-propenoate and isoxazole-5-carbonyl chloride using the procedure described above (Example 2) for the preparation of ethyl-3-((5'-methylisoxazole-3'-carbonyl)-L-Leu-L-Phe-L-(Tr-Gln))-E-propenoate: $R_f$=0.36 (5% CH$_3$OH in CH$_2$Cl$_2$); IR (cm$^{-1}$) 3284, 1717, 1650; $^1$H NMR (CDCl$_3$) δ 0.97 (d, 3H, J=6.8), 1.01 (d, 3H, J=6.8), 1.28 (t, 3H, J=7.2), 1.51–1.64 (m, 2H), 1.72–1.84 (m, 1H), 1.95–2.05 (m, 1H), 2.11–2.33 (m, 2H), 2.48 (s, 3H), 2.98 (dd, 1H, J=13.7, 5.6), 3.16–3.24 (m, 3H), 3.80 (s, 3H), 3.81 (s, 3H), 4.17 (q, 2H, J=7.2), 4.23 (d, 1H, J=14.3), 4.31–4.42 (m, 1H), 4.40 (d, 1H, J=14.3), 4.44–4.50 (m, 1H), 4.88–4.96 (m, 1H), 5.79 (dd, 1H, J=15.6, 1.4), 6.43–6.49 (m, 3H), 6.71 (dd, 1H, J=15.6, 5.3), 6.80–6.88 (m, 2H), 6.94 (d, 1H, J=9.3), 7.11–7.17 (m, 3H), 7.29 (d, 1H, J=8.7), 8.33 (d, 1H, J=6.2); Anal. ($C_{39}H_{48}FN_5O_9 \cdot 0.5H_2O$) C, H, N.

Preparation of Product Ethyl-3-{(5'-Methylisoxazole-3'-carbonyl)-L-Val-L-(4-F-Phe)-L-((S)-Pyrrol-Ala)}-E-Propenoate A suspension of ethyl-3-{(5'-methylisoxazole-3'-carbonyl)-L-Val-L-(4-F-Phe)-L-((N-2,4-dimethoxybenzyl)-(S)-pyrrol-Ala)}-E-propenoate (0.263 g, 0.351 mmol, 1 equiv.), water (2 drops), and DDQ (0.104 g, 0.458 mmol, 1.3 equiv.) was refluxed for 9 h and then allowed to cool to room temperature over 8 h. The reaction mixture was diluted with CH$_2$Cl$_2$ (200 mL) and washed with a 2:1 mixture of saturated NaHCO$_3$ and 1 N NaOH (20 mL). The organic phase was dried over MgSO$_4$ and evaporated. Purification of the residue by flash column chromatography (gradient elution 2→3% CH$_3$OH in CH$_2$Cl$_2$) gave ethyl-3-{(5'-methylisoxazole-3'-carbonyl)-L-Val-L-(4-F-Phe)-L-((S)-pyrrol-Ala)}-E-propenoate (0.117 g, 56%) as a white solid: mp=219–220° C.; $R_f$=0.23 (5% CH$_3$OH in CH$_2$Cl$_2$); IR (cm$^{-1}$) 3401 br, 3295, 1655 br; $^1$H NMR (CDCl$_3$) δ 0.94 (d, 3H, J=6.8), 0.97 (d, 3H, J=6.5), 1.29 (t, 3H, J=7.2), 1.54–1.65 (m, 1H), 1.72–1.91 (m, 2H), 2.07–2.26 (m, 2H), 2.28–2.39 (m, 1H), 2.49 (d, 3H, J=0.9), 3.01 (dd, 1H, J=13.8, 6.1), 3.12 (dd, 1H, J=13.8, 6.4), 3.26–3.38 (m, 2H), 4.18 (q, 2H, J=7.2), 4.34 (dd, 1H, J=8.7, 7.2), 4.43–4.54 (m, 1H), 4.90 (dt, 1H, J=9.0, 6.2), 5.76 (dd, 1H, J=15.6, 1.6), 6.00 (s, 1H), 6.42 (q, 1H, J=0.9), 6.72 (dd, 1H, J=15.6, 5.4), 6.86–6.94 (m, 2H), 7.01 (d, 1H, J=9.0), 7.11–7.18 (m, 2H), 7.21 (d, 1H, J=8.7), 7.76 (d, 1H, J=7.2); Anal. ($C_{30}H_{38}FN_5O_7$) C, H, N.

Example 7

Preparation of Compound A-6: Ethyl-3-[(5'-Methylisoxazole-3'-carbonyl)-L-Val-L-(4-F-Phe)-L-Gln]-E-Propenoate

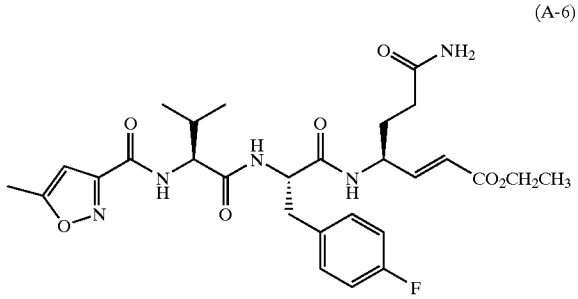

(A-6)

Preparation of Intermediate Ethyl-3-{Boc-L-(4-F)-Phe-L-(Tr-Gln)}-E-Propenoate

This compound was prepared from ethyl-3-(Boc-L-(Tr-Gln))-E-propenoate and Boc-L-(4-F)-Phe-OH using a procedure like that described above (Example 2) for the preparation of ethyl-3-(Boc-L-Phe-L-(Tr-Gln))-E-propenoate: IR (cm$^{-1}$) 3328, 1707, 1506, 1168; $^1$H NMR (CDCl$_3$) δ 1.29 (t, 3H, J=7.2), 1.37 (s, 9H), 1.66–1.78 (m, 1H), 1.88–1.98 (m, 1H), 2.32 (t, 2H, J=6.6), 2.85–2.92 (m, 1H), 2.97–3.04 (m, 1H), 4.18 (q, 2H, J=7.2), 4.52 (m, 1H), 4.96 (m, 1H), 5.60 (d, 1H, J=15.6), 6.56 (d, 1H, J=8.1), 6.66 (dd, 1H, J=15.6, 5.1), 6.80 (s, br, 1H), 6.92–6.98 (m, 2H), 7.08–7.12 (m, 2H), 7.17–7.23 (m, 6H), 7.24–7.33 (m, 10H); Anal. (C$_{42}$H$_{46}$FN$_3$O$_6$) C, H, N.

Preparation of Intermediate Ethyl-3-{Boc-L-Val-L-(4-F)-Phe-L-(Tr-Gln)}-E-Propenoate This compound was prepared from ethyl-3-{Boc-L-(4-F)-Phe-L-(Tr-Gln)}-E-propenoate and Boc-L-Val-OH in the manner described above (Example 2) for the preparation of ethyl-3-{Boc-L-Leu-L-Phe-L-(Tr-Gln)}-E-propenoate: IR (cm$^{-1}$) 3319, 1657, 1511, 1172; $^1$H NMR (CDCl$_3$) δ 0.78 (d, 3H, J=6.9), 0.87 (d, 3H, J=6.9), 1.29 (t, 3H, J=7.2), 1.37 (s, 9H), 1.69–1.79 (m, 1H), 1.93–2.06 (m, 2H), 2.33 (t, 2H, J=7.2), 2.97–3.04 (m, 1H), 3.73–3.77 (m, 1H), 4.18 (q, 2H, J=7.2), 4.42–4.54 (m, 2H), 4.80 (d, 1H, J=6.9), 5.61 (dd, 1H, J=15.6, 1.5), 6.44 (d, 1H, J=7.8), 6.69 (dd, 1H, J=15.9, 5.4), 6.71 (s, br, 1H), 6.92–6.98 (m, 2H), 7.07–7.13 (m, 2H), 7.18–7.31 (m, 16H), 8.02 (s, 1H); Anal. (C$_{47}$H$_{55}$FN$_4$O$_7$) C, H, N.

Preparation of Intermediate Ethyl-3-{(5'-Methylisoxazole-3'-carbonyl)-L-Val-L-(4-F)-Phe-L-(Tr-Gln)}-E-Propenoate This compound was prepared from ethyl-3-{Boc-L-Val-L-(4-F)-Phe-L-(Tr-Gln)}-E-propenoate and 5-methylisoxazole-3-carbonyl chloride in a manner like that described above (Example 2) for the preparation of ethyl-3-{(5'-methylisoxazole-3'-carbonyl)-L-Leu-L-Phe-L-(Tr-Gln)}-E-propenoate: IR (cm$^{-1}$) 3319, 1657, 1511, 1172; $^1$H NMR (CDCl$_3$) δ 0.84 (d, 3H, J=6.9), 0.89 (d, 3H, J=6.9), 1.30 (t, 3H, J=7.2), 1.68–1.80 (m, 1H), 1.95–2.06 (m, 1H), 2.08–2.17 (m, 1H), 2.34 (t, 2H, J=7.2), 2.44 (s, 3H), 2.87–2.94 (m, 1H), 3.01–3.08 (m, 1H), 4.18 (q, 2H, J=7.2), 4.48–4.56 (m, 2H), 5.68 (dd, 1H, J=15.6, 1.8), 6.23 (s, 1H), 6.39 (d, 1H, J=7.8), 6.70 (dd, 1H, J=15.9, 5.4), 6.84–6.90 (m, 3H), 7.04–7.08 (m, 4H), 7.17–7.30 (m, 16H); Anal. (C$_{47}$H$_{50}$N$_5$O$_7$) C, H, N.

Preparation of Product Ethyl-3-{(5'-Methylisoxazole-3'-carbonyl)-L-Val-L-(4-F)-Phe-L-Gln}-E-Propenoate Ethyl-3-{(5'-Methylisoxazole-3'-carbonyl)-L-Val-L-(4-F)-Phe-L-(Tr-Gln)}-E-propenoate was deprotected using the procedure described above (Example 2) for the preparation of ethyl-3-{(5'-methylisoxazole-3'-carbonyl)-L-Leu-L-Phe-L-Gln}-E-propenoate: IR (cm$^{-1}$) 3284, 1652, 1542; $^1$H NMR (DMSO-d$_6$) δ 0.76 (d, 3H, J=6.9), 0.79 (d, 3H, J=6.9), 1.20 (t, 3H, J=7.2), 1.57–1.76 (m, 2H), 1.96–2.06 (3H), 2.46 (s, 3H), 2.75–2.83 (m, 1H), 2.89–2.96 (m, 1H), 4.09 (q, 2H, J=7.2), 4.13–4.25 (m, 1H), 4.35 (m, 1H), 4.49–4.56 (m, 1H), 5.53 (d, 1H, J=15.6), 6.57 (s, 1H), 6.66 (dd, 1H, J=15.6, 5.4), 6.75 (s, br, 1H), 6.97–7.03 (m, 2H), 7.17–7.24 (m, 3H), 8.15 (d, 1H, J=7.8), 8.24 (d, 1H, J=8.7), 8.32 (d, 1H, J=8.1); Anal. (C$_{28}$H$_{36}$N$_5$O$_7$) C, H, N.

Example 8

Preparation of Compound A-7: Ethyl-3-{(5'-Methylisoxazole-3'-carbonyl)-L-α-(t-Butyl-Gly)-L-(4-F-Phe)-L-((S)-Pyrrol-Ala)}-E-Propenoate (A-7)

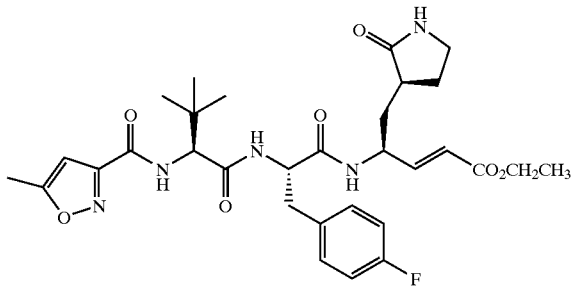

Preparation of Intermediate Boc-L-(4-F-Phe)-Obn

DCC (0.765 g, 3.71 mmol, 1.05 equiv.), benzyl alcohol (0.347 mL, 3.35 mmol, 0.95 equiv.) and DMAP (0.022 g, 0.18 mmol, 0.05 equiv.) were added sequentially to a solution of Boc-L-(4-F-Phe)-OH (1.0 g, 3.53 mmol, 1 equiv.) in CH$_2$Cl$_2$ (15 mL). After stirring 18 h, the precipitate was removed by filtration, and the filtrate was diluted with MTBE (75 mL), washed with 10% KHSO$_4$ and brine (10 mL each), dried over Na$_2$SO$_4$ and evaporated. Purification of the residue by flash column chromatography (12% EtOAc in hexanes) gave Boc-L-(4-F-Phe)-OBn (0.992 g, 79%) as a white solid. $^1$H NMR spectral data matches literature (see Jackson et al., J. Org. Chem. 1992, vol. 57, 3397).

Preparation of Intermediate Boc-L-α-(t-Butyl-Gly)-L-(4-F-Phe)-OBn

Boc-L-(4-F-Phe)-OBn (2.0 g, 5.36 mmol, 1 equiv.) was stirred for 1 h in a mixture of CH$_2$Cl$_2$ (20 mL) and TFA (10 mL), then more TFA (10 mL) was added and the reaction solution was stirred an additional hour. The volatiles were evaporated and the residue was dissolved in DMF (30 mL). Boc-L-α-(t-butyl-Gly)-OH (1.24 g, 5.36 mmol, 1 equiv.) was added, and the solution was cooled to 0° C. N,N-diisopropylethylamine (2.80 mL, 16.1 mmol, 3 equiv.) and HATU (2.04 g, 5.37 mmol, 1 equiv.) were added sequentially. After stirring 20 min., the reaction mixture was allowed to warm to room temperature over 1 h, then diluted with MTBE (500 mL) and washed with 5% KHSO$_4$ (100 mL), saturated NaHCO$_3$ (50 mL), and brine (50 mL). The organic phase was dried and evaporated. Purification of the residue by flash column chromatography (20% EtOAc in hexanes) gave Boc-L-α-(t-butyl-Gly)-L-(4-F-Phe)-OBn (2.04 g, 78%) as a white foam: R$_f$=0.49 (25% EtOAc in hexanes); IR (cm$^{-1}$) 3307, 1737, 1655 br; $^1$H NMR (CDCl$_3$) δ 0.94 (s, 9H), 1.45 (s, 9H), 3.04 (dd, 1H, J=14.2, 5.8), 3.11 (dd, 1H, J=14.2, 6.1), 3.79 (d, 1H, J=9.3), 4.88 (dt, 1H, J=7.8, 5.8), 5.08 (d, 1H, J=12.0), 5.16–5.23 (m, 1H), 5.19 (d, 1H, J=12.0), 6.08 (d, 1H, J=7.8), 6.83–6.97 (m, 4H), 7.28–7.40 (m, 5H); Anal. (C$_{27}$H$_{35}$FN$_2$O$_5$) C, H, N.

Preparation of Intermediate Ethyl-3-{Boc-L-α-(t-Butyl-Gly)-L-(4-F-Phe)-L-((N-2,4-Dimethoxybenzyl)-(S)-Pyrrol-Ala)}-E-Propenoate A solution of HCl in 1,4-dioxane (4.0 M, 8 mL) was added to a solution of ethyl-3-{Boc-L-((N-2,4-dimethoxybenzyl)-

(S)-pyrrol-Ala)}-E-propenoate (0.309 g, 0.648 mmol, 1 equiv.) in 1,4-dioxane (8 mL). After stirring for 1.5 h, the volatiles were evaporated to give the crude amine salt as a foam.

Palladium on carbon (10%, 200 mg) was added to a solution of Boc-L-α-(t-butyl-Gly)-L-(4-F-Phe)-OBn (2.04 g, 4.19 mmol) in EtOAc (200 mL). The atmosphere was replaced with hydrogen via balloon. After stirring 3 h, the atmosphere was replaced with argon, and the reaction mixture was filtered through #3 and #5 Whatman filter papers. The filtrate was evaporated to give a white foam.

This foam was combined with the crude amine salt (prepared above) in DMF (5 mL) and cooled to 0° C. N,N-diisopropylethylamine (0.339 mL, 1.95 mmol, 3 equiv.) and HATU (0.247 g, 0.650 mmol, 1 equiv.) were added sequentially. After stirring 20 min., the reaction mixture was allowed to warm to room temperature over 1 h, then diluted with MTBE (100 mL) and washed with 5% KHSO$_4$, saturated NaHCO$_3$ and brine (15 mL each). The organic phase was dried and evaporated. Purification of the residue by flash column chromatography (60% EtOAc in hexanes) gave ethyl-3-{Boc-L-α-(t-butyl-Gly)-L-(4-F-Phe)-L-((N-2,4-dimethoxybenzyl)-(S)-pyrrol-Ala)}-E-propenoate (0.364 g, 74%) as a white foam: R$_f$=0.34 (60% EtOAc in hexanes); IR (cm$^{-1}$) 3284, 1713, 1655; $^1$H NMR (CDCl$_3$) δ 1.01 (s, 9H), 1.28 (t, 3H, J=7.2), 1.46 (s, 9H), 1.50–1.63 (m, 211), 1.68–1.81 (m, 1H), 1.85–1.99 (m, 1H), 2.09–2.20 (m, 1H), 2.94 (dd, 1H, J=13.5, 5.4), 3.15–3.26 (m, 3H), 3.80 (s, 3H), 3.82 (s, 3H), 3.97 (d, 1H, J=9.3), 4.17 (q, 2H, J=7.2), 4.27–4.38 (m, 1H). 4.29 (d, 1H, J=14.3), 4.42 (d, 1H, J=14.3), 4.84–4.92 (m, 1H), 5.22 (d, 1H, J=9.6), 5.74 (dd, 1H, J=15.6, 1.6), 6.45–6.53 (m, 2H), 6.69 (dd, 1H, J=15.6, 5.4), 6.76–6.87 (m, 3H), 7.10–7.28 (m, 3H), 8.26 (d, 1H, J=5.9); Anal. (C$_{40}$H$_{55}$FN$_4$O$_9$) C, H, N.

Preparation of Intermediate Ethyl-3-{(5'-Methylisoxazole-3'-carbonyl)-L-α-(t-Butyl-Gly)-L-(4-F-Phe)-L-((N-2,4-Dimethoxybenzyl)-(S)-Pyrrol-Ala)}-E-Propenoate This compound was prepared from ethyl-3-{Boc-L-α-(t-butyl-Gly)-L-(4-F-Phe)-L-((N-2,4-dimethoxybenzyl)-(S)-pyrrol-Ala)}-E-propenoate and isoxazole-5-carbonyl chloride using the procedure described above (Example 2) for the preparation of ethyl-3-{(5'-methylisoxazole-3'-carbonyl)-L-Leu-L-Phe-L-(Tr-Gln)}-E-propenoate: R$_f$=0.60 9H), 1.29 (t, 3H, J=7.2), 1.51–1.64 (m, 2H), 1.71–1.83 (m, 1H), 1.96–2.07 (m, 1H), 2.11–2.21 (m, 1H), 2.49 (s, 3H), 2.99 (dd, 1H, J=13.7, 5.9), 3.13–3.26 (m, 3H), 3.80 (s, 3H), 3.81 (s, 3H), 4.18 (q, 2H, J=7.2), 4.23–4.48 (m, 4H), 4.85–4.93 (m, 1H), 5.76 (dd, 1H, J=15.6, 1.4), 6.40–6.52 (m, 3H), 6.71 (dd, 1H, J=15.6, 5.3), 6.79–6.88 (m, 2H, 6.92 (d, 1H, J=9.0), 7.09–7.22 (m, 3H), 7.37 (d, 1H, J=9.0), 8.27 (d, 1H, J=6.2); Anal. (C$_{40}$H$_{50}$FN$_5$O$_9$·0.25H$_2$O) C, H, N.

Preparation of Product Ethyl-3-{(5'-Methylisoxazole-3'-carbonyl)-L-α-(t-Butyl-Gly)-L-(4-F-Phe)-L-((S)-Pyrrol-Ala)}-E-Propenoate This compound was prepared from ethyl-3-{(5'-methylisoxazole-3'-carbonyl)-L-α-(t-Butyl-Gly)-L-(4-F-Phe)-L-((N-2,4-dimethoxybenzyl)-(S)-Pyrrol-Ala)}-E-propenoate using a procedure as described above (Example 6) for the preparation of ethyl-3-{(5'-methylisoxazole-3'-carbonyl)-L-Val-L-(4-F-Phe)-L-((S)-Pyrrol-Ala)}-E-propenoate: R$_f$=0.30 (5% CH$_3$OH in CH$_2$Cl$_2$); IR (cm$^{-1}$) 3307 br, 1684, 1660; $^1$H NMR (CDCl$_3$) δ 1.02 (s, 9H), 1.29 (t, 3H, J=7.2), 1.51–1.61 (m, 1H), 1.75–1.97 (m, 2H), 2.14–2.25 (m, 1H), 2.28–2.40 (m, 1H), 2.50 (s, 3H), 3.03 (d, 2H, J=6.5), 3.27–3.42 (m, 2H), 4.18 (q, 2H, J=7.2), 4.36 (d, 1H, J=9.8), 4.52–4.63 (m, 1H), 4.86–4.95 (m, 1H), 5.71 (dd, 1H, J=15.6, 1.4), 6.44 (s, 1H), 6.57–6.64 (m, 1H), 6.73 (dd, 1H, J=15.6, 5.3), 6.83–6.91 (m, 2H), 7.09–7.15 (m, 2H), 7.28–7.36 (m, 2H), 7.59 (d, 1H, J=8.1); Anal. (C$_{31}$H$_{40}$FN$_5$O$_7$) C, H, N.

Example 9

Preparation of Compound A-8: Ethyl-3-{(5'-Methylisoxazole-3'-carbonyl)-L-Val-L-(4-F-Phe)-L-((S)-Piper-Ala)}-E-Propenoate

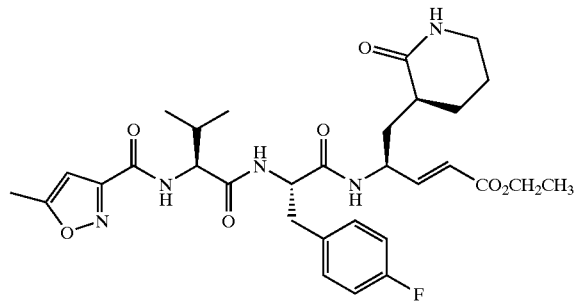

(A-8)

Preparation of Intermediate (2'S,4S,4"S)-4-{2'-(4-Benzyl-2"-oxo-oxazolidine-3"-carbonyl)-5'-hydroxypentyl}-2-dimethyloxazolidine-3-carboxylic Acid tert-Butyl Ester A solution of borane-tetrahydrofuran complex (0.96 mL of a 1.0 M solution in TBF, 0.96 mmol, 1 equiv.) was added to a 0° C. solution of (2'S,4S,4"S)-4-{2'-(4"-benzyl-2'-oxo-oxazolidine-3"-carbonyl)-pent-4'-enyl}-2,2-dimethyloxazolidine-3-carboxylic acid tert-butyl ester (prepared as described in Example 6, 0.455 g, 0.963 mmol, 1 equiv.) in THF (3 mL). After stirring 30 min., water (3 mL) and sodium perborate tetrahydrate (0.148 g, 0.962 mmol, 1 equiv.) were added, and the ice bath was removed. After an additional hour, the reaction mixture was diluted with MTBE (125 mL), washed with water (15 mL) and brine (2×15 mL), dried over Na$_2$SO$_4$, and concentrated. Purification of the residue by flash column chromatography (50% EtOAc in hexanes) provided (2'S,4S,4"S)-4-{2'-(4"-benzyl-2"-oxo-oxazolidine-3"-carbonyl)-5'-hydroxypentyl}-2,2-dimethyloxazolidine-3-carboxylic acid tert-butyl ester (0.339 g, 72%) as a colorless glass: R$_f$=0.41 (50% EtOAc in hexanes); IR (cm$^{-1}$) 3486, 1780, 1693; $^1$H NMR (CDCl$_3$) δ 1.42–1.85 (m, 21H), 2.13–2.24 (m, 1H), 2.70 (dd, 1H, J=13.1, 10.0), 3.29–3.38 (m, 1H), 3.61–4.22 (m, 8H), 4.63–4.76 (m, 1H), 7.19–7.38 (m, 5H); Anal. (C$_{26}$H$_{38}$N$_2$O$_7$·0.5H$_2$O) C, H, N.

Preparation of Intermediate (1S,3'S)-{2-(1'-(2",4"-Dimethoxybenzyl)-2'-oxo-piperidin-3'-yl)-1-hydroxymethylethyl}-carbamic Acid tert-Butyl Ester (2'S,4S,4"S)-4-{2'-(4"-Benzyl-2"-oxo-oxazolidine-3"-carbonyl)-5'-hydroxypentyl}-2,2-dimethyloxazolidine-3-carboxylic acid tert-butyl ester (3.88 g, 7.92 mmol, 1 equiv.) was dissolved in Et$_3$N (3.97 mL, 28.51 mmol, 3.6 equiv.). The mixture was cooled to −12° C., and a solution of sulfur trioxide-pyridine complex (5.04 g, 31.67 mmol, 4 equiv.) in DMSO (150 mL) was added at a rate to maintain the temperature between 8–17° C. The solution was stirred at 23° C. for 3 h. The reaction mixture was cooled in an ice water bath and quenched by the addition of H$_2$O (150 mL). The resulting solution was extracted with EtOAc (2×150 mL). The combined organic layers were washed with 5% citric acid (100 mL), brine (100 mL), dried over Na$_2$SO$_4$ and filtered. The solvent was removed under reduced pressure and the residue was dried under vacuum to give a white foam (3.53 g).

To a solution of this material (3.53 g, 7.22 mmol, 1 equiv.) in a 2:1 mixture of THF and EtOH (120 mL) was added 2,4-dimethoxybenzylamine hydrochloride (5.88 g, 28.89 mmol, 4 equiv.), NaOAc (2.37 g, 28.89 mmol, 4 equiv.), and NaBH$_3$CN (0.908 g, 14.45 mmol, 2 equiv.). The reaction mixture was stirred overnight (20 h) and then diluted with MTBE (200 mL). The organic layer was washed with 10% KHSO$_4$ (100 mL), saturated NaHCO$_3$ (100 mL), and brine (100 mL), and dried over Na$_2$SO$_4$, and concentrated to give a pale yellow foam.

To a solution of this foam (3.34 g, 7.22 mmol, 1 equiv.) in CH$_3$OH (50 mL) was added p-toluenesulfonic acid (0.275 g, 1.44 mmol, 0.2 equiv.). The reaction mixture was stirred at 50° C. for 2.5 h and then was diluted with CH$_2$Cl$_2$ (100 mL). The organic layer was washed with saturated NaHCO$_3$ (100 mL), dried over Na$_2$SO$_4$, and concentrated. The residue was purified by flash column chromatography (3% CH$_3$OH in CH$_2$Cl$_2$) to give (1S,3'S)-{2-(1'-(2",4"-dimethoxybenzyl)-2'-oxo-piperidin-3'-yl)-1-hydroxymethyl-ethyl}-carbamic acid tert-butyl ester as a white foam (1.33 g, 44% over three steps): $^1$H NMR (CDCl$_3$): δ 1.44 (s, 9H), 1.71–1.85 (m, 2H), 1.92–1.98 (m, 2H), 2.40–2.48 (m, 1H), 2.71–2.78 (m, 1H), 3.19–3.32 (m, 2H), 3.45–3.69 (m, 4H), 4.11–4.20 (m, 2H), 4.68 (m, 1H), 5.47 (m, 1H), 6.44 (s, 1H), 7.20–7.33 (m, 2H).

Preparation of Product Ethyl-3-{(5'-Methylisoxazole-3'-carbonyl)-L-Val-L-(4-F-Phe)-L-((S)-Piper-Ala)}-E-Propenoate (1S,3'S)-{2-(1'-(2",4"-Dimethoxybenzyl)-2'-oxo-piperidin-3'-yl)-1-hydroxy-methylethyl}-carbamic acid tert-butyl ester was converted to the product ethyl-3-{(5'-methylisoxazole-3'-carbonyl)-L-Val-L-(4-F-Phe)-L-((S)-Piper-Ala)}-E-propenoate in a manner analogous to the conversion of (1S,3'S)-{2-(1'-(2",4"-dimethoxybenzyl)-2'-oxo-piperidin-3'-yl]-1-hydroxymethylethyl)-carbamic acid tert-butyl ester to product ethyl-3-{(5'-methylisoxazole-3'-carbonyl)-L-Val-L-(4-F-Phe)-L-((S)-Pyrrol-Ala)}-E-propenoate described in Example 6 above: R$_f$=0.24 (5% CH$_3$OH in CH$_2$Cl$_2$); IR (cm$^{-1}$) 3284 br, 1713, 1655, 1637 br; $^1$H NMR (CDCl$_3$) δ 0.94 (d, 3H, J=6.8), 0.98 (d, 3H, J=6.8), 1.29 (t, 3H, J=7.2), 1.43–1.56 (m, 2H), 1.66–1.78 (m, 1H), 1.83–2.05 (m, 4H), 2.16–2.28 (m, 1H), 2.49 (s, 3H), 3.00 (dd, 1H, J=13.7, 6.2), 3.13 (dd, 1H, J=13.7, 5.9), 3.21–3.37 (m, 2H), 4.18 (q, 2H, J=7.2), 4.36–4.45 (m, 2H), 4.80–4.88 (m, 1H), 5.76 (dd, 1H, J=15.6, 1.6), 5.96 (s, 1H), 6.43 (s, 1H), 6.70 (dd, 1H, J=15.6, 5.3), 6.81 (d, 1H, J=8.7), 6.86–6.98 (m, 2H), 7.09–7.19 (m, 2H), 7.22–7.29 (m, 1H), 8.07 (d, 1H, J=6.5).

Example 10

Preparation of Compound B-1: Ethyl-3-{(5'-Methylisoxazole-3'-carbonyl)-L-ValΨ(COCH$_2$)-L-(4-F-Phe)-L-Gln}-E-Propenoate

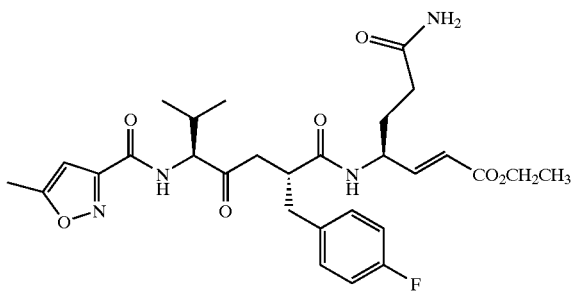

(B-1)

Preparation of Intermediate trans-6-Methyl-hept-4-enoic Acid

A solution of isobutyraldehyde (9.59 g, 133 mmol, 1 equiv.) in THF (50 mL) was added dropwise via addition funnel to a solution of vinylmagnesium bromide (133 mL of a 1.0 M solution in THF, 133 mmol, 1.0 equiv.) in THF (300 mL) at 0° C. Upon completion of the addition, the reaction mixture was stirred for 30 min. at 0° C., and then ethyl malonyl chloride (17.0 mL, 133 mmol, 1.0 equiv.) was added. After stirring for 1 h at 0° C., the reaction mixture was partitioned between saturated NH$_4$Cl (150 mL) and a 1:1 mixture of EtOAc and hexanes (2×200 mL). The combined organic layers were dried over Na$_2$SO$_4$ and were concentrated. Purification of the residue by filtration through silica gel (eluting with 5% EtOAc in hexanes) afforded the intermediate malonate ester (11.5 g, 40% yield). This material was not characterized, but was combined (neat) with Ti(OEt)$_4$ (1.13 mL, 5.39 mmol, 0.10 equiv.) and was heated to 190° C. for 4 h, and then was cooled to 60° C. EtOH (50 mL) and 6.0 M KOH (50 mL) were added sequentially, and the brown reaction mixture was refluxed for 4 h. After cooling to 23° C., the reaction mixture was filtered through a medium frit, and the filtrate was partitioned between water (150 mL) and Et$_2$O (2×150 mL). The aqueous layer was then acidified to pH=2 (as indicated by pH paper) with concentrated HCl and was extracted with a 1:1 mixture of EtOAc and hexanes (2×150 mL). The combined organic layers were dried over Na$_2$SO$_4$, concentrated, and the residue was distilled at reduced pressure to afford trans-6-methyl-hept-4-enoic acid (3.58 g, 47%) as a colorless liquid: bp 107–112° C. (1 Torr); IR (cm$^{-1}$) 2960, 1711; $^1$H NMR (CDCl$_3$) δ 0.96 (d, 6H, J=6.5), 2.18–2.45 (m, 5H), 5.31–5.50 (m, 2H); Anal. (C$_8$H$_{14}$O$_2$) C, H.

Preparation of Intermediate trans-6-Methyl-hept-4-enoic Acid (2R-hydroxy-1R-methyl-2-phenyl-ethyl)-methyl Amide Oxalyl chloride (2.25 mL, 25.8 mmol, 1.05 equiv.) was added to a solution of trans-6-methyl-hept-4-enoic acid (3.50 g, 24.6 mmol, 1 equiv.) and N,N-dimethylformamide (0.03 mL, 0.39 mmol, 0.016 equiv.) in benzene (60 mL) at 23° C. The reaction mixture was stirred at 23° C. for 2 h, and then was concentrated under reduced pressure. The resulting oil was dissolved in THF (20 mL) and was added via cannula to a solution of (1R,2R)-(−)-pseudoephedrine (3.87 g, 23.4 mmol, 1 equiv.) and triethylamine (3.92 mL, 28.1 mmol, 1.2 equiv.) in THF (150 mL) at 0° C. The reaction mixture was stirred at 0° C. for 30 min., then was partitioned between half-saturated NH$_4$Cl (150 mL) and EtOAc (2×150 mL). The combined organic layers were dried over Na$_2$SO$_4$, concentrated, and the residue purified by flash column chromatography (gradient elution 40→50% EtOAc in hexanes) to afford trans-6-methyl-hept-4-enoic acid (2R-hydroxy-1R-methyl-2-phenyl-ethyl)-methyl amide (6.31 g, 93%) as a viscous oil: R$_f$=0.35 (50% EtOAc in hexanes); IR (cm$^{-1}$) 3382, 1622; $^1$H NMR (CDCl$_3$, mixture of rotamers) δ 0.96 (d, J=6.8), 0.97 (d, J=6.5), 1.11 (d, J=6.9), 2.18–2.59 (m), 2.82 (s), 2.92 (s), 3.99–4.04 (m), 4.32–4.42 (m), 4.44–4.49 (m), 4.55–4.62 (m), 5.32–5.49 (m), 7.24–7.42 (m); Anal. (C$_{18}$H$_{27}$NO$_2$) C, H, N.

Preparation of Intermediate trans-6-Methyl-2S-(4-fluorobenzyl)-hept-4-enoic Acid (2R-Hydroxy-1R-methyl-2-phenylethyl)methyl Amide n-Butyllithium (32.5 mL of a 1.6 M solution in hexanes, 52.0 mmol, 3.1 equiv.) was added to a suspension of anhydrous lithium chloride (7.18 g, 169 mmol, 10 equiv.) and diisopropylamine (7.80 mL, 55.7 mmol, 3.3 equiv.) in THF (250 mL) at −78° C. The reaction mixture was stirred for 30 min. at −78° C., was maintained at 0° C. for 5 min., and subsequently cooled again to −78° C. trans-6-Methyl-hept-4-enoic acid (2R-hydroxy-1R-methyl-2-phenyl-ethyl)-methyl amide (4.91 g, 17.0 mmol, 1 equiv) in THF (50 mL) was added via cannula, and the resulting solution was stirred at −78° C. for 1.75 h, maintained at 0° C. for 20 min., stirred at 23° C. for 5 min., and then was cooled again to 0° C. A solution of 4-fluorobenzyl bromide (6.34 mL, 50.9 mmol, 3 equiv.) in THF (15 mL) was added and the reaction mixture was stirred at 0° C. for 30 min., which was then partitioned between half-saturated NH$_4$Cl (230 mL) and a 1:1 mixture of EtOAc and hexanes (200 mL, 2×150 mL). The combined organic layers were dried over Na$_2$SO$_4$ and were concentrated. Purification of the residue by flash column chromatography (gradient elution 20→40% EtOAc in hexanes) provided trans-6-methyl-2S-(4-fluorobenzyl)-hept-4-enoic acid (2R-hydroxy-1R-methyl-2-phenylethyl)methyl amide (6.33 g, 94%) as a viscous oil: R$_f$=0.38 (40% EtOAc in hexanes); IR (cm$^{-1}$) 3378, 1614; $^1$H NMR (CDCl$_3$, mixture of rotamers) δ 0.85–0.95 (m), 0.96 (d, J=6.8), 2.10–2.32 (m), 2.34–2.46 (m), 2.58 (s), 2.67–2.79 (m), 2.82–2.94 (m), 3.00–3.18 (m), 3.94 (br), 4.37–4.52 (m), 5.24–5.42 (m), 5.44–5.56 (m), 6.89–7.01 (m), 7.08–7.14 (m), 7.19–7.38 (m); Anal. (C$_{25}$H$_{32}$FNO$_2$) C, H, N.

Preparation of Intermediate 5S-(1R-Bromo-2-methylpropyl)-3R-(4-fluorobenzyl)dihydrofuran-2-one N-Bromosuccinimide (2.93 g, 16.5 mmol, 1.05 equiv.) was added in small portions over 10 minutes to a solution of trans-6-methyl-2S-(4-fluorobenzyl)-hept-4-enoic acid (2R-hydroxy-1R-methyl-2-phenylethyl)methyl amide (6.24 g, 15.7 mmol, 1 equiv.) and glacial acetic acid (4.49 mL, 78.4 mmol, 5 equiv.) in a 4:1 mixture of THF and H$_2$O (165 mL) at 0° C. The resulting yellow solution was stirred for 15 min. at 0° C., and then was warmed to 23° C. and subsequently refluxed for 45 min. After cooling to 23° C., the reaction mixture was partitioned between half-saturated NaHCO$_3$ (200 mL) and a 1:1 mixture of EtOAc and hexanes (2×200 mL, 100 mL). The combined organic layers were dried over Na$_2$SO$_4$ and were concentrated. Flash chromatographic purification of the residue (gradient elution 4→10% EtOAc in hexanes) gave 5S-(1R-bromo-2-methylpropyl)-3R-(4-fluorobenzyl)dihydrofuran-2-one (4.14 g, 80%) as a pale yellow oil (containing approximately 5–10% unidentified impurities by $^1$H NMR): R$_f$=0.56 (25% EtOAc in hexanes); IR (cm$^{-1}$) 1772; $^1$H NMR (CDCl$_3$, major isomer) δ 0.94 (d, 3H, J=6.5), 1.00 (d, 3H, J=6.8), 2.05–2.35 (m, 3H), 2.83 (dd, 1H, J=13.6, 8.4), 2.92–3.03 (m, 1H), 3.11 (dd, 1H, J=13.6, 4.7), 3.90 (dd, 1H, J=9.0, 3.7), 4.33–4.40 (m, 1H), 6.98–7.06 (m, 2H), 7.14–7.20 (m, 2H); Anal. (C$_{15}$H$_{18}$BrFO$_2$) C, H.

Preparation of Intermediate 5S-(1S-Azido-2-methylpropyl)-3R-(4-fluorobenzyl)dihydrofuran-2-one A suspension of sodium azide (1.90 g, 29.2 mmol, 2.5 equiv.) and 5S-(1R-bromo-2-methylpropyl)-3R-(4-fluorobenzyl)dihydrofuran-2-one (3.85 g, 11.7 mmol, 1 equiv.) in N,N-dimethylformamide (40 mL) was heated at 50° C. for 67 hours. The reaction mixture was cooled to 23° C. and was partitioned between half-saturated NaCl (200 mL) and a 1:1:1 mixture of EtOAc, hexanes and acetone (2×200 mL, 100 mL). The combined organic layers were dried over Na$_2$SO$_4$, concentrated, and the residue purified by flash column chromatography (gradient elution 9→17% EtOAc in hexanes) to give 5S-(1S-azido-2-methylpropyl)-3R-(4-fluorobenzyl)dihydrofuran-2-one (2.10 g, 62%) as a white solid (containing approximately 5–10% unidentified impurities by $^1$H NMR): mp 91–96° C.; R$_f$=0.44 (25% EtOAc in hexanes); IR (cm$^{-1}$) 2097, 1772; $^1$H NMR (CDCl$_3$, major isomer) δ 0.99 (d, 3H, J 6.5), 1.02 (d, 3H, J=6.8), 1.95–2.20 (m, 3H), 2.78–2.88 (m, 1H), 2.94 (dd, 1H, J=7.0, 4.2), 3.03–3.17 (m, 2H), 4.37–4.43 (m, 1H), 6.97–7.09 (m, 2H), 7.14–7.21 (m, 2H).

Preparation of Intermediate {2-Methyl-1S-(4R-(4-fluorobenzyl)-5-oxotetrahydrofuran-2S-yl)propyl}-carbamic Acid tert-Butyl Ester A suspension of 5S-(1S-azido-2-methylpropyl)-3R-(4-fluorobenzyl)dihydrofuran-2-one (2.02 g, 6.93 mmol, 1 equiv.), di-tert-butyl dicarbonate (2.12 g, 9.71 mmol, 1.4 equiv.) and Pd/C (10%, 0.20 g) in CH$_3$OH (100 mL) was stirred under a hydrogen atmosphere (balloon) for 16 hours. The reaction mixture was vacuum filtered through Whatman #3 paper and concentrated. Purification of the residue by flash column chromatography (15% EtOAc in hexanes) provided {2-methyl-1S-(4R-(4-fluorobenzyl)-5-oxotetrahydrofuran-2S-yl)propyl}-carbamic acid tert-butyl ester (1.58 g, 62%) as a white foam: R$_f$=0.80 (5% MeOH in CH$_2$Cl$_2$); IR (cm$^{-1}$) 3331, 1766, 1702; $^1$H NMR (CDCl$_3$) δ 0.93 (d, 3H, J=6.8), 0.95 (d, 3H, J=6.5), 1.41 (s, 9H), 1.71–1.83 (m, 1H), 1.95–2.06 (m, 1H), 2.16–2.27 (m, 1H), 2.80 (dd, 1H, J=13.5, 8.6), 2.88–2.99 (m, 1H), 3.09 (dd, 1H, J=13.5, 4.4), 3.32–3.40 (m, 1H), 4.42–4.48 (m, 2H), 6.95–7.03 (m, 2H), 7.11–7.18 (m, 2H); Anal. (C$_{20}$H$_{28}$FNO$_4$) C, H, N.

Preparation of Intermediate Ethyl-3-{Boc-L-ValΨ(COCH$_2$)-L-(4-F-Phe)-L-(Tr-Gln)}-E-Propenoate Lithium hydroxide (9.62 mL of a 1 M aqueous solution, 9.62 mmol, 5 equiv.) was added to a solution of {2-methyl-1S-(4R-(4-fluorobenzyl)-5-oxotetrahydrofuran-2S-yl)propyl}-carbamic acid tert-butyl ester (0.703 g, 1.92 mmol, 1 equiv.) in DME (25 mL) at 23° C. The resulting suspension was stirred at 23° C. for 30 min., and then was partitioned between 10% KHSO$_4$ (50 mL) and CH$_2$Cl$_2$ (3×100 mL). The combined organic layers were dried over Na$_2$SO$_4$, concentrated, and the residue dissolved in CH$_2$Cl$_2$ (30 mL). Powdered 4 Å molecular sieves (0.70 g), 4-methylmorpholine N-oxide (0.451 g, 3.85 mmol, 2 equiv.), and tetrapropylammonium perruthenate (0.068 g, 0.19 mmol, 0.10 equiv.) were added sequentially. The resulting dark reaction mixture was stirred for 1.33 hours at 23° C., then was vacuum filtered through Whatman #3 paper and then through Whatman #5 paper. The filtrate was concentrated under reduced pressure to provide a dark residue, which was dissolved in CH$_2$Cl$_2$ (30 mL). Crude ethyl-3-(H$_2$N-L-(Tr-Gln))-E-propenoate·HCl (2.30 mmol, 1.2 equiv., prepared as described in Example 2 for the preparation of ethyl-3-{(5'-methylisoxazole-3'-carbonyl)-L-Leu-L-Phe-L-Gln}-E-propenoate), 4-methylmorpholine (0.846 mL, 7.69 mmol, 4 equiv.), HOBt (0.390 g, 2.89 mmol, 1.5 equiv.), and EDC (0.553 g, 2.88 mmol, 1.5 equiv.) were added sequentially, and the reaction mixture was stirred for 19 hours at 23° C. and then was partitioned between brine (100 mL) and CH$_2$Cl$_2$ (3×100 mL). The combined organic layers were dried over Na$_2$SO$_4$ and were concentrated. Purification of the residue by flash column chromatography (gradient elution 35→40% EtOAc in hexanes) provided ethyl-3-{Boc-L-ValΨ(COCH$_2$)-L-(4-F-Phe)-L-(Tr-Gln)}-E-propenoate (0.820 g, 53%) as a tan foam: R$_f$=0.50 (50% EtOAc in hexanes); IR (cm$^{-1}$) 3307, 1708, 1666; $^1$H NMR (CDCl$_3$) δ 0.67 (d, 3H, J=6.8), 0.92 (d, 3H, J=6.8), 1.28 (t, 3H, J=7.2), 1.40 (s, 9H), 1.53–1.67 (m, 1H), 1.91–2.04 (m, 2H), 2.32–2.41 (m, 2H), 2.46–2.55 (m, 1H), 2.63 (dd, 1H, J=12.1, 5.9), 2.69–2.80 (m, 1H), 2.83 (dd, 1H, J=12.1, 8.2), 3.03 (dd, 1H, J=17.7, 10.0), 4.05–4.11 (m, 1H), 4.17 (q, 2H, J=7.2), 4.40–4.50 (m, 1H), 4.84 (d, 1H, J=8.4), 5.38 (d, 1H, J=15.7), 6.01 (d, 1H, J=8.4), 6.60 (dd, 1H, J=15.7, 5.0), 6.92–6.99 (m, 2H), 7.03–7.12 (m, 3H), 7.17–7.30 (m, 15H); Anal. (C$_{48}$H$_{56}$FN$_3$O$_7$) C, H, N.

Preparation of Product Ethyl-3-{(5'-Methylisoxazole-3'-carbonyl)-L-ValΨ(COCH$_2$)-L-(4-F-Phe)-L-Gln)}-E-Propenoate Ethyl-3-{Boc-L-ValΨ(COCH$_2$)-L-(4-F-Phe)-L-(Tr-Gln)}-E-propenoate was converted to product ethyl-3-{(5'-methylisoxazole-3'-carbonyl)-L-ValΨ(COCH$_2$)-L-(4-F-Phe)-L-Gln}-E-propenoate in a manner analogous to that described in Example 2 above for the conversion of ethyl-3-{Boc-L-Leu-L-Phe-L-(Tr-Gln)}-E-propenoate to product ethyl-3-{(5'-methylisoxazole-3'-carbonyl)-L-Leu-L-Phe-L-Gln)-E-propenoate: mp=220° C. (dec); R$_f$=0.35 (10% CH$_3$OH in CH$_2$Cl$_2$); IR (cm$^{-1}$) 3277, 1715, 1643; $^1$H NMR (DMSO-d$_6$) δ 0.81 (d, 3H, J=6.2), 0.87 (d, 3H, J=6.9), 1.21 (t, 3H, J=6.5), 1.59–1.67 (m, 2H), 2.03 (s, br, 2H), 2.21–2.24 (m, 1H), 2.46 (s, 3H), 2.57–2.68 (m, 3H), 2.80–2.95 (m, 2H), 4.09 (q, 2H, J=6.5), 4.30–4.34 (m, 2H), 5.41 (d, 1H, J=15.5), 6.55 (s, 1H), 6.61 (dd, 1H, J=15.5, 5.5), 6.73 (s, 1H), 6.99–7.16 (m, 5H), 8.01 (d, 1H, J=7.8), 8.69 (d, 1H, J=8.7); Anal. (C$_{29}$H$_{37}$FN$_4$O$_7$) C, H, N.

Example 11

Preparation of Compound A-10: Ethyl-3-((5'-Methylisoxazole-3'-carbonyl)-L-Leu-NCH$_3$-L-Phe-L-Gln}-E-Propenoate

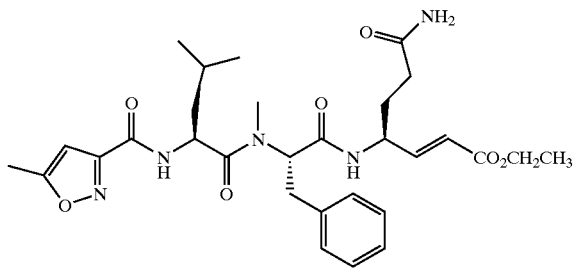

(A-10)

Preparation of Intermediate Boc-L-Leu-NCH$_3$-L-Phe-OCH$_3$

NCH$_3$-L-Phe-OCH$_3$·HCl (1.4 g) was dissolved in CH$_2$Cl$_2$ (50 mL) and poured into a combination of aqueous (aq) 1 N NaOH (7 mL) and saturated aqueous NaHCO$_3$ (25 mL). After mixing, the organic phase was separated and the aqueous phase was washed with CH$_2$Cl$_2$ (3×50 mL). The combined organic phases were dried over Na$_2$SO$_4$ and evaporated to give the free amine as a clear colorless oil (1.14 g, 5.90 mmol). A solution of this amine and (iPr)$_2$NEt (1.13 mL, 6.49 mmol) in DMF (10 mL) was added dropwise to a 0° C. solution of Boc-L-Leu-OH (1.50 g, 6.49 mmol) and HOBt (0.877 g, 6.49 mmol) in DMF (10 mL). DCC (1.47 g, 7.12 mmol) was added. The reaction mixture was stirred at 0° C. for 1 h, and was then stirred at 23° C. for 48 h. The mixture was filtered to remove the precipitate (ppt) and the filtrate was evaporated. The residue was dissolved in CH$_2$Cl$_2$ (200 mL), washed with saturated aqueous NaHCO$_3$ (40 mL), dried over Na$_2$SO$_4$ and evaporated. The residue was purified by flash column chromatography (25% EtOAc in hexanes) to give Boc-L-Leu-NCH$_3$-L-Phe-OCH$_3$ as a white solid (2.04 g, 85%): mp=126–127° C.; IR (cm$^-$) 3401, 3319, 1743, 1708, 1649; $^1$H NMR (CDCl$_3$) (major isomer) δ 0.92 (d, 3H, J=6.8), 0.95 (d, 3H, J=6.5), 1.32–1.48 (m, 2H), 1.41 (s, 9H), 1.61–1.77 (m, 1H), 2.90 (s, 3H), 3.04 (dd, 1H, J=14.5, 10.5), 3.37 (dd, 1H, J=14.5, 5.5), 3.72 (s, 3H), 4.48–4.57 (m, 1H), 4.98–5.04 (m, 1H), 5.20 (dd, 1H, J=10.5, 5.5), 7.16–7.32 (m 5H); Anal. (C$_{22}$H$_{34}$N$_2$O$_5$) C, H, N.

Preparation of Intermediate Boc-L-Leu-NCH$_3$-L-Phe-OH

Boc-L-Leu-NCH$_3$-L-Phe-OCH$_3$ (0.625 g, 1.54 mmol) was dissolved in CH$_3$OH (20 mL) and cooled to 0° C. Aqueous NaOH (6.15 mL of a 2N solution, 12.3 mmol) was added dropwise. The reaction mixture was stirred for 3 h at 23° C., and then poured into 10% aqueous KHSO$_4$ (150 mL). This mixture was extracted with CH$_2$Cl$_2$ (3×100 mL), and the combined organic phases were dried over Na$_2$SO$_4$ and evaporated to give Boc-L-Leu-NCH$_3$-L-Phe-OH as a white foam (0.617 g, quant.), which was used without purification.

Preparation of Intermediate Ethyl-3-{BOC-L-Leu-NCH$_3$-L-Phe-L-(Tr-Gln)}-E-Propenoate This intermediate was prepared from Boc-L-Leu-NCH$_3$-L-Phe-OH and ethyl-3-{H$_2$N-L-(Tr-Gln)}-E-propenoate·HCl (prepared as described in Example 2) in a manner analogous to that described for the preparation of ethyl-3-{Boc-L-Leu-L-Phe-L-(Tr-Gln)}-E-propenoate in Example 2 above: IR (cm$^{-1}$) 3295, 1713, 1672, 1649; $^1$H NMR (CDCl$_3$) (mixture of isomers) δ 0.65 (d, J=6.2), 0.66 (d, J=6.5), 0.84 (d, J=6.5), 0.88 (d, J=6.5), 1.02–1.22 (m), 1.23–1.38 (m), 1.33 (s), 1.41 (s), 1.55–1.82 (m), 1.89–2.07 (m), 2.23–2.30 (m), 2.90 (s), 2.94 (s), 3.01 (dd, J=14.6, 10.9), 3.03–3.13 (m), 3.26–3.37 (m), 3.27 (dd, J=14.6, 3.4), 3.42–3.54 (m), 4.00–4.22 (m), 4.37–4.73 (m), 4.82–4.89 (m), 5.53–5.70 (m), 5.95 (dd, J=15.9, 1.2), 6.23–6.28 (m), 6.66–6.75 (m), 6.79–6.89 (m), 7.09–7.34 (m), 8.14 (d, J=8.7); Anal. (C$_{49}$H$_{60}$N$_4$O$_7$) C, H, N.

Preparation of Product Ethyl-3-{(5'-Methylisoxazole-3'-carbonyl)-L-Leu-NCH$_3$-L-Phe-L-Gln}-E-Propenoate Ethyl-3-{Boc-L-Leu-NCH$_3$-L-Phe-L-(Tr-Gln)}-E-propenoate was converted to product ethyl-3-{(5'-methylisoxazole-3'-carbonyl)-L-Leu-NCH$_3$-L-Phe-L-Gln}-E-propenoate in a manner analogous to that described in Example 2 above for the conversion of ethyl-3-{Boc-L-Leu-L-Phe-L-(Tr-Gln)}-E-propenoate to product ethyl-3-{(5'-methylisoxazole-3'-carbonyl)-L-Leu-L-Phe-L-Gln}-E-propenoate: R$_f$=0.23 (5% CH$_3$OH in CH$_2$Cl$_2$); IR (cm$^-$) 3295, 1713, 1666, 1637; $^1$H NMR (CDCl$_3$) (mixture of isomers) δ 0.65 (d, J=6.5), 0.71 (d, J=6.5), 0.93 (d, J=6.5), 0.94 (d, J=6.5), 1.30 (t, J=7.2), 1.24–1.73 (m), 1.81–2.22 (m), 2.45 (s), 2.48 (s), 2.86–2.93 (m), 2.96 (s), 2.97 (s), 3.03–3.14 (m), 3.21–3.31 (m), 3.48 (dd, J=14.0, 5.9), 4.19 (q, J=7.2), 4.20 (q, J=7.2), 4.38–4.45 (m), 4.52–4.70 (m), 4.74–4.81 (m), 5.62–5.67 (m), 5.73–5.79 (m), 5.81 (dd, J=15.6, 1.6), 5.99 (dd, J=15.6, 1.6), 6.03–6.09 (m), 6.35 (s), 6.39 (s), 6.40–6.45 (m), 6.77–6.94 (m), 7.42 (d, J=7.2), 8.13 (d, J=7.8).

Example 12

Preparation of Compound C-1: Ethyl-3-{(5'-Methylisoxazole-3'-carbonyl)-L-Val-O-L-(4-F-Phe)-L-Gln}-E-Propenoate (C-1)

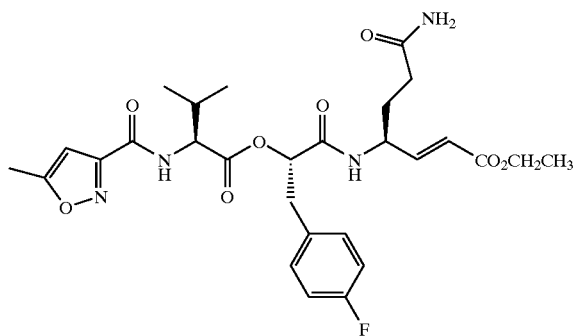

Preparation of Intermediate Allyl (S)-1-Hydroxy-3-(4-fluorophenyl)propionate

In a flask fitted with a thermometer and a reflux condenser was dissolved methyl (S)-1-hydroxy-3-(4-fluorophenyl) propionate (prepared from L-H$_2$N-(4-F-Phe)-OCH$_3$ by the method described in Hoffman et al., Tetrahedron 1992, vol. 48, 3007) (0.99 g, 5.0 mmol) in allyl alcohol (50 mL). Titanium tetraisopropoxide (1.53 mL, 5.0 mmol) was if added, and the reaction brought to 90° C. for 3.5 h. The reaction was cooled to room temperature and poured into 250 mL of 1:1 EtOAc/saturated NH$_4$Cl solution. The organic phase was separated and washed with water (100 mL), brine (100 mL), dried (MgSO$_4$), and the solvent removed. The residue was subjected to flash column chromatography eluting with a gradient of 5–10% EtOAc/hexanes to afford 0.77 g (68%) of allyl (S)-1-hydroxy-3-(4-fluorophenyl) propionate as a clear liquid: R$_f$=0.21 (15% EtOAc/hexanes); IR (neat) 3470 (broad), 1734, 1510, 1221 cm$^{-1}$; $^1$H NMR (DMSO-d$_6$) δ 1.24–1.27 (m, 1H), 2.92–2.99 (m, 1H), 3.09–3.15 (m, 1H), 4.43–4.47 (m, 1H), 4.65 (d, 2H, J=5.9), 5.28–5.37 (m, 2H), 5.86–5.95 (m, 1H), 6.95–7.01 (m, 2H), 7.16–7.21 (m, 2H).

Preparation of Intermediate Boc-L-Val-O-L-(4-F-Phe)-OCH$_2$CH═CH$_2$

Allyl (S)-1-hydroxy-3-(4-fluorophenyl)propionate (0.070 g, 0.31 mmol) was dissolved in CH$_2$Cl$_2$ (20 mL). Boc-L-Val-OH (0.068 g, 0.31 mmol) was added, followed by DMAP (0.004 g, 0.03 mmol) and DCC (0.067 g, 0.33 mmol). The reaction was stirred at room temperature overnight, and the solvent was removed in vacuo. The residue was subjected to flash column chromatography eluting with a gradient of 3–5% EtOAc/hexanes. The Boc-L-Val-O-L-(4-F-Phe)-OCH$_2$CH═CH$_2$ product was obtained as 0.12 g (90%) of a clear oil: R$_f$=0.18 (10% EtOAc/hexanes); IR (neat) 1752, 1717 1510 cm$^{-1}$; $^1$H NMR (DMSO-d$_6$) δ 0.80–0.85 (m, 6H), 1.36 (s, 9H), 1.97–2.04 (m, 1H), 3.07–3.15 (m, 2H), 3.89–3.94 (m, 1H), 4.51–4.55 (m, 2H), 5.17–5.30 (m, 3H), 5.75–5.84 (m, 1H), 7.06–7.17 (m, 3H), 7.27–7.32 (m, 2H); Anal. (C$_{22}$H$_{30}$NO$_6$F) C, H, N.

Preparation of Intermediate Ethyl-3-{Boc-L-Val-O-L-(4-F-Phe)-L-(Tr-Gln)}-E-Propenoate Boc-L-Val-O-L-(4-F-Phe)-OCH$_2$CH═CH$_2$ (0.65 g, 1.52 mmol) was dissolved in THF (15 mL). Tetrakis (triphenylphosphine)palladium(0) (0.035 g, 0.03 mmol) was added, and the reaction stirred 5 min. at 23° C. Morpholine (0.16 mL, 1.83 mmol) was added dropwise, and the reaction stirred at room temperature for 2 h. The solvent was removed in vacuo, and the residue taken up in 50 mL of 4:1 hexanes/Et$_2$O. The product was extracted into sat. NaHCO$_3$ solution (50 mL), and the organic phase discarded. The aqueous phase was acidified to pH=1–2 with solid KHSO$_4$, and the product re-extracted into EtOAc (50 mL). The organic phase was washed with brine (50 mL), dried (MgSO$_4$), and concentrated to give 0.50 g (86%) of the free acid as a clear oil. This material was dissolved in DMF (6 mL). Diisopropylethylamine (0.43 mL, 2.50 mmol) was added, followed by ethyl-3-{H$_2$N-L-(Tr-Gln)}-E-propenoate.HCl (prepared as described in Example 2 above, 0.55 g, 1.25 mmol). The reaction was cooled to 0° C. HATU (0.48 g, 1.25 mmol) was added, and the reaction allowed to warm to room temperature. The DMF was removed in vacuo. The residue was dissolved with EtOAc (30 mL), and the organic phase washed consecutively with 10% HCl solution (25 mL), saturated NaHCO$_3$ solution (25 mL), H$_2$O (25 mL), and brine (25 mL). The organic layer was dried (MgSO$_4$), filtered, and concentrated, and the residue was purified by flash column chromatography (0→1.0% MeOH/CH$_2$Cl$_2$) to give 0.40 g (39%) of ethyl-3-{Boc-L-Val-O-L-(4-F-Phe)-L-(Tr-Gln)}-E-propenoate as a white amorphous solid: R$_f$=0.25 (3% MeOH/CHCl$_3$); IR(KBr) 1691, 1512, 1159 cm$^{-1}$; $^1$H NMR (DMSO-d$_6$) δ 0.78–0.83 (m, 6H), 1.20 (t, 3H, J=7.0), 1.35 (s, 9H), 1.58–1.66 (m, 2H), 1.96–2.02 (m, 1H), 2.19–2.33 (m, 2H), 2.99–3.02 (m, 2H), 3.82–3.87

(m, 1H), 4.09 (q, 2H, J=7.0), 4.33–4.37 (m, 1H), 5.03–5.08 (m, 1H), 5.60 (d, 1H, J=15.8), 6.67 (dd, 1H, J=15.8, 5.5), 7.02–7.08 (m, 2H), 7.14–7.28 (m, 18H), 8.12 (d, 1H, J=8.1), 8.59 (s, 1H); Anal. ($C_{47}H_{54}N_3O_8F$) C, H, N.

Preparation of Product Ethyl-3-{(5'-Methylisoxazole-3'-carbonyl)-L-Val-O-L-(4-F-Phe)-L-Gln}-E-Propenoate Ethyl-3-{Boc-L-Val-O-L-(4-F-Phe)-L-(Tr-Gln)}-E-propenoate was converted to product ethyl-3-{(5'-methylisoxazole-3'-carbonyl)-L-Val-O-L-(4-F-Phe)-L-Gln}-E-propenoate in a manner analogous to that described in Example 2 above for the conversion of ethyl-3-{Boc-L-Leu-L-Phe-L-(Tr-Gln)}-E-propenoate to product ethyl-3-{(5'-methylisoxazole-3'-carbonyl)-L-Leu-L-Phe-L-Gln}-E-propenoate: $R_f$=0.05 (3% MeOH/CHCl$_3$); IR (KBr) 1746, 1719, 1661, 1549 cm$^{-1}$; $^1$H NMR (DMSO-d$_6$) δ 0.87 (d, 3H, J=6.6), 0.92 (d, 3H, J=6.6), 1.20 (t, 3H, J=7.0), 1.61–1.74 (m, 2H), 1.96–2.01 (m, 2H), 2.15–2.22 (m, 1H), 2.46 (s, 3H), 3.00–3.03 (m, 2H), 4.10 (q, 2H, J=7.0), 4.27–4.32 (m, 1H), 4.33–4.38 (m, 1H), 5.06–5.11 (m, 1H), 5.63 (d, 1H, J=15.6), 6.54 (s, 1H), 6.68 (dd, 1H, J=15.6, 5.5), 6.78 (s, br, 1H), 6.95–7.00 (m, 2H), 7.20–7.24 (m, 3H), 8.06 (d, 1H, J=8.1), 8.87 (d, 1H, J=7.7); Anal. ($C_{28}H_{35}N_4O_8F$) C, H, N.

Example 13

Preparation of Compound A-11: Ethyl-3-{(5'-Methylisoxazole-3'-carbonyl)-L-(2-Naphth)-NCH$_3$-L-(4-F-Phe)-L-Gln}-E-Propenoate (A-11)

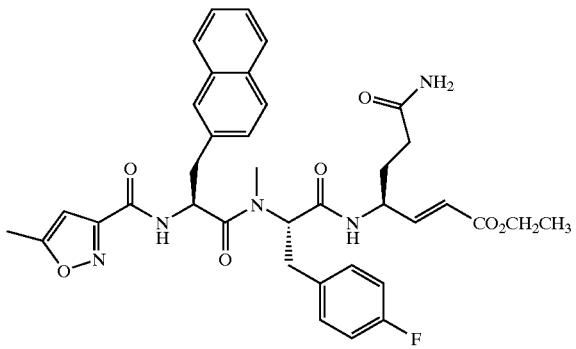

Preparation of Intermediate Ethyl-3-{Boc-NCH$_3$-L-(4-F-Phe)-L-(Tr-Gln)}-E-Propenoate Boc-(4-F-Phe)-OH (4.46 g, 15.75 mmol, 1 equiv.) and CH$_3$I (7.84 mL, 126 mmol, 8 equiv.) were dissolved in dry THF (100 mL) and cooled to 0° C. NaH (1.89 g, 47.25 mmol, 3 equiv.) was added to this solution with vigorous stirring. After stirring at 23° C. for 24 h, EtOAc (3 mL) and H$_2$O (3 mL) were added carefully to the mixture, and the resulting suspension was evaporated to dryness. After dissolving in H$_2$O (100 mL), the reaction mixture was washed with Et$_2$O (2×100 mL). The aqueous layer was acidified to pH=3 with 10% citric acid solution, and then extracted with EtOAc (2×100 mL). The combined EtOAc extracts were washed successively with half-saturated NaHCO$_3$ (150 mL), 5% Na$_2$S$_2$O$_3$ (150 mL), and H$_2$O (150 mL), dried over Na$_2$SO$_4$, and concentrated to give Boc-NCH$_3$-(4-F-Phe)-OH as a pale yellow foam (4.37 g, 80%), which was used without further purification: $^1$H NMR (CDCl$_3$, mixture of isomers) δ 1.35 (s), 1.40 (s), 2.69 (s), 2.75 (s), 2.96–3.13 (m), 3.23–3.33 (m), 4.54–4.58 (m), 4.76–4.81 (m), 6.96–7.01 (m), 7.15–7.17 (m).

A solution of HCl in 1,4-dioxane (4.0 M, 15 mL) was added to a solution of ethyl-3-(Boc-L-(Tr-Gln))-E-propenoate (prepared as described in Example 2 above, 3.57 g, 6.73 mmol, 1 equiv.) in the same solvent (15 mL) at 23° C. After 2 h, the volatiles were removed under reduced pressure. The residue was dissolved in CH$_2$Cl$_2$ (50 mL), and Boc-NCH$_3$-(4-F-Phe)-OH (prepared as in the preceding paragraph, 2.0 g, 6.73 mmol, 1.0 equiv.), HOBt (1.23 g, 9.09 mmol, 1.5 equiv), 4-methylmorpholine (2.0 mL, 18.19 mmol, 3 equiv.), and EDC (1.74 g, 9.09 mmol, 1.5 equiv.) were added sequentially. The reaction mixture was stirred at 23° C. overnight, and then was partitioned between water (100 mL) and CH$_2$Cl$_2$ (2×100 mL). The combined organic layers were dried over Na$_2$SO$_4$, concentrated, and the residue was purified by flash column chromatography (30% EtOAc in hexane) to afford ethyl-3-{Boc-NCH$_3$-L-(4-F-Phe)-L-(Tr-Gln)}-E-propenoate (4.07 g, 84%) as white foam: IR (cm$^{-1}$) 1666, 1510, 1167; $^1$H NMR (CDCl$_3$, mixture of isomers) δ 1.29 (t, J=7.2), 1.37 (s), 1.65–1.75 (m), 1.95–2.06 (m), 2.29–2.33 (m), 2.66 (s), 2.91–2.99 (m), 3.22–3.29 (m), 4.18 (q, J=7.2), 4.52–4.58 (m), 5.68 (d, J=15.9), 6.45 (d, J=8.4), 6.74 (dd, J=15.6, 5.4), 6.91–6.99 (m), 7.11–7.33 (m); Anal. ($C_{43}H_{48}FN_3O_6$) C, H, N.

Preparation of Intermediate Ethyl-3-{Boc-L-(2-Naphth)-NCH$_3$-L-(4-F-Phe)-L-(Tr-Gln)}-E-Propenoate A solution of HCl in 1,4-dioxane (4.0 M, 3 mL), was added to a solution of ethyl-3-{Boc-NCH$_3$-L-(4-F-Phe)-L-(Tr-Gln)}-E-propenoate (0.388 g, 0.54 mmol, 1 equiv.) in the same solvent (3 mL) at 23° C. After 2 h, the volatiles were removed under reduced pressure. The residue was dissolved in DMF (10 mL), cooled at 0° C., and DIEA (0.188 mL, 1.08 mmol, 2 equiv.), Boc-L-(2-Naphth)-OH (0.170 g, 0.54 mmol, 1.0 equiv.) and HATU (0.205 g, 0.54 mmol, 1 equiv.) were added sequentially. The reaction mixture was stirred at 23° C. for 1 h. The volatiles were removed under reduced pressure, and the resulting residue was taken into EtOAc (50 mL), and washed with 0.5 N HCl (50 mL), saturated NaHCO$_3$ (50 mL) and brine (50 mL). The organic layer was dried over Na$_2$SO$_4$, concentrated, and the residue was purified by flash column chromatography (40% EtOAc in hexane) to afford ethyl-3-{Boc-L-(2-Naphth)-NCH$_3$-L-(4-F-Phe)-L-(Tr-Gln)}-E-propenoate (0.437 g, 88%) as white foam: IR (cm$^{-1}$) 1656, 1509, 1162; $^1$H NMR (CDCl$_3$, mixture of isomers) δ 0.88 (t, J=7.2), 1.27 (s), 1.30 (s), 1.48–1.58 (m), 1.64–1.67 (m), 1.97–2.11 (m), 2.23–2.28 (m), 2.42–2.50 (m), 2.62–2.69 (m), 2.80 (s), 2.90 (s), 3.00–3.07 (m), 3.15–3.20 (m), 3.25–3.32 (m), 4.18 (q, J=7.2), 4.42–4.46 (m), 4.53–4.56 (m), 4.61–4.66 (m), 4.72–4.82 (m), 5.94–5.00 (m), 5.63 (d, J=15.6), 6.12 (d, J=15.6), 6.60 (dd, J=15.6, 5.4), 6.75–6.89 (m), 6.70–7.08 (m), 7.19–7.30 (m), 7.41–7.50 (m), 7.70–7.82 (m), 8.80 (d, J=8.4); Anal. ($C_{56}H_{59}FN_4O_7$) C, H, N.

79

Preparation of Product Ethyl-3-{(5'-Methylisoxazole-3'-carbonyl)-L-(2-Naphth)-NCH₃-L-(4-F-Phe)-L-Gln}-E-Propenoate Ethyl-3-{Boc-L-(2-Naphth)-NCH₃-L-(4-F-Phe)-L-(Tr-Gln)}-E-propenoate was converted to product ethyl-3-{(5'-methylisoxazole-3'-carbonyl)-L-(2-Naphth)-NCH₃-L-(4-F-Phe)-L-Gln}-E-propenoate in a manner analogous to that described in Example 2 above for the conversion of ethyl-3-{Boc-L-Leu-L-Phe-L-(Tr-Gln)}-E-propenoate to product ethyl-3-{(5'-methylisoxazole-3'-carbonyl)-L-Leu-L-Phe-L-Gln}-E-propenoate IR (cm⁻¹) 3296, 1654, 1510; ¹H NMR (DMSO-d₆, mixture of isomers) δ 1.17–1.24 (m), 1.62–1.78 (m), 2.04–2.15 (m), 2.38 (s), 2.42 (s), 2.71–2.79 (m), 2.84 (s), 2.87–2.92 (m), 3.03 (s), 3.15 (d, J=7.5), 3.98–4.06 (m), 4.08–4.12 (m), 4.38–4.42 (m), 4.94 (m), 5.03–5.07 (m), 5.09–5.18 (m), 5.66–5.82 (m), 6.42 (s), 6.43 (s), 6.66–6.81 (m), 6.88–6.94 (m), 7.01–7.06 (m), 7.13–7.17 (m), 7.24–7.34 (m), 7.43–7.46 (m), 7.56 (s), 7.76–7.84 (m), 8.08 (d, J=7.8), 8.60 (d, J=8.4), 9.01 (d, J=7.2); Anal. (C₃₇H₄₀FN₅O₇·0.75H₂O) C, H, N.

Example 14

Preparation of Compound A-9: Ethyl-3-{(5'-Methylisoxazole-3'-carbonyl)-L-His-NCH₃-L-(4-F-Phe)-L-Gln}-E-Propenoate

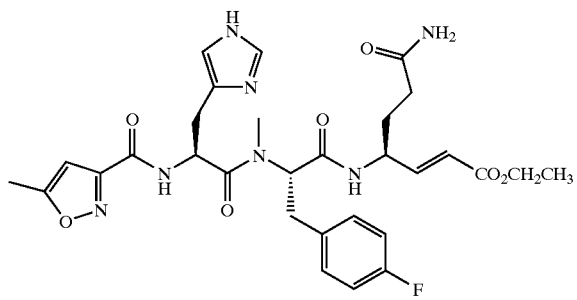

(A-9)

Ethyl-3-{Boc-NCH₃-L-(4-F-Phe)-L-(Tr-Gln)}-E-propenoate (described in Example 13 above) was converted to product ethyl-3-{(5'-methylisoxazole-3'-carbonyl)-L-His-NCH₃-L-(4-F-Phe)-L-Gln}-E-propenoate in a manner analogous to the preparation of product ethyl-3-{(5'-methylisoxazole-3'-carbonyl)-L-(2-Naphth)-NCH₃-L-(4-F-Phe)-L-Gln}-E-propenoate described in Example 13 above (utilizing Boc-L-(Tr-His)-OH in lieu of Boc-L-(2-Naphth)-OH): IR (cm⁻¹) 3302, 1665, 1202; ¹H NMR (DMSO-d₆, mixture of isomers) δ 1.21 (t, J=7.2), 1.70–1.78 (m), 2.05–2.09 (m), 2.41 (s), 2.44 (s), 2.69–3.26 (m), 4.11 (q, J=7.2), 4.38–4.53 (m), 5.07–5.19 (m), 6.51–5.84 (m), 6.44 (s), 6.48 (s), 6.63–6.86 (m), 6.89–7.01 (m), 7.09–7.19 (m), 7.23–7.42 (m), 8.02 (d, J=8.7), 8.15 (d, J=8.1), 8.59 (d, J=8.7), 8.94 (s), 9.04 (s), 9.14 (d, J=6.9); Anal. (C₃₀H₃₆FN₇O₇·TFA·H₂O) C, H, N.

80

Example 15

Preparation of Compound A-12: Ethyl-3-{(5'-Methylisoxazole-3'-carbonyl)-L-Leu-NCH₃-L-(4-F-Phe)-L-Gln}-E-Propenoate

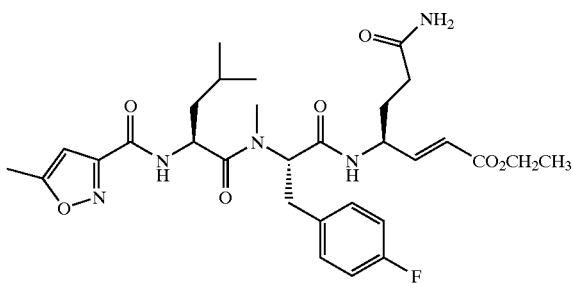

(A-12)

Ethyl-3-{Boc-NCH₃-L-(4-F-Phe)-L-(Tr-Gln)}-E-propenoate (described in Example 13 above) was converted to product ethyl-3-{(5'-methylisoxazole-3'-carbonyl)-L-Leu-NCH₃-L-(4-F-Phe)-L-Gln}-E-propenoate in a manner analogous to the preparation of product ethyl-3-{(5'-methylisoxazole-3'-carbonyl)-L-(2-Naphth)-NCH₃-L-(4-F-Phe)-L-Gln}-E-propenoate described in Example 13 above (utilizing Boc-L-Leu-OH in lieu of Boc-L-(2-Naphth)-OH): IR (cm⁻¹) 3325, 1663, 1171; ¹H NMR (DMSO-d₆, mixture of isomers) δ 0.64–0.67 (m), 0.86–0.88 (m), 1.17–1.23 (m), 1.32–1.40 (m), 1.59–1.75 (m), 1.98–2.07 (m), 2.42 (s), 2.45 (s), 2.08 (s), 2.86–2.93 (m), 2.99 (s), 3.12–3.20 (m), 4.05–4.15 (m), 4.41–4.50 (m), 4.82–5.07 (m), 5.62 (d, J=15.9), 5.86 (d, J=15.9), 6.51 (s), 6.53 (s), 6.68–6.73 (m), 6.93–6.99 (m), 7.09–7.21 (m), 7.26–7.31 (m), 8.03 (d, J=7.8), 8.08 (d, J=7.8), 8.41 (d, J=8.1), 8.94 (d, J=7.2); Anal. (C₃₀H₄₀FN₅O₇·1.25CH₂Cl₂) C, H, N.

Example 16

Preparation of Compound A-13: Ethyl-3-{(5'-Methylisoxazole-3'-carbonyl)-L-(1-Naphth)-NCH₃-L-(4-F-Phe)-L-Gln}-E-Propenoate

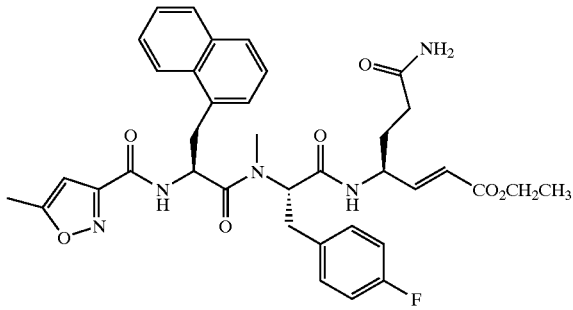

(A-13)

Ethyl-3-{Boc-NCH₃-L-(4-F-Phe)-L-(Tr-Gln)}-E-propenoate (described in Example 13 above) was converted to product ethyl-3-{(5'-methylisoxazole-3'-carbonyl)-L-(1-Naphth)-NCH₃-L-(4-F-Phe)-L-Gln}-E-propenoate in a manner analogous to the preparation of product ethyl-3-{(5'-methylisoxazole-3'-carbonyl)-L-(2-Naphth)-NCH₃-L-(4-F-Phe)-L-Gln}-E-propenoate described in Example 13 above, but utilizing Boc-L-(1-Naphth)-OH in lieu of Boc-L-(2-Naphth)-OH: IR (cm⁻¹) 3308, 1659, 1169; ¹H NMR (DMSO-d₆, mixture of isomers) δ 1.16–1.23 (m), 1.61–1.78 (m), 1.98–2.02 (m), 2.07–2.12 (m), 2.41 (s), 2.43 (s), 2.77 (s), 2.78 (s), 2.84–2.87 (m), 2.93–3.03 (m), 3.08–3.14 (m), 3.31–3.38 (m), 4.00–4.15 (m), 4.27–4.32 (m), 4.40–4.46 (m), 4.58–4.64 (m), 5.07–5.17 (m), 5.57–5.73 (m), 6.45 (s), 6.57–6.61 (m), 6.71–6.88 (m), 6.89–6.91 (m), 7.11–7.19 (m), 7.31–7.38 (m), 7.50–7.58 (m), 7.73–7.78 (m), 7.83–7.94 (m), 8.08 (d, J=8.1), 8.13 (d, J=8.7), 8.62 (d, J=8.1), 9.14 (d, J=8.1); Anal. (C₃₇H₄₀FN₅O₇) C, H, N.

Example 17

Preparation of Compound B-2: Ethyl-3-{(5'-Methylisoxazole-3'-carbonyl)-L-ValΨ(COCH₂)-L-(4-F-Phe)-L-((S)-Pyrrol-Ala)}-E-Propenoate

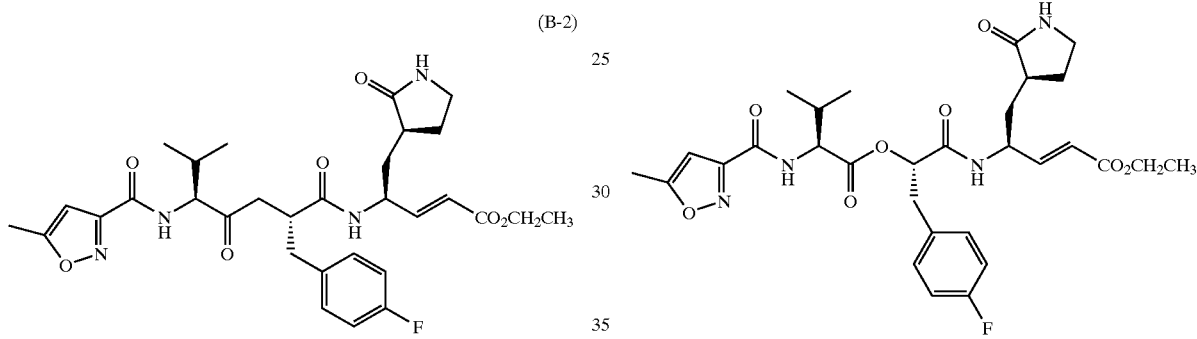

(B-2)

Preparation of Intermediate Ethyl-3-{Boc-L-ValΨ(COCH₂)-L-(4-F-Phe)-L-{(N-2,4-Dimethoxybenzyl)-(S)-Pyrrol-Ala}-E-Propenoate This intermediate was prepared from {2-methyl-1S-(4R-(4-fluorobenzyl)-5-oxotetrahydrofuran-2S-yl)propyl}-carbamic acid tert-butyl ester (described in Example 10) and ethyl-3-{Boc-L-((N-2,4-dimethoxybenzyl)-(S)-pyrrol-Ala)}-E-propenoate (described in Example 6) in a manner analogous to the preparation of ethyl-3-{Boc-L-(4-Me-Phe)-L-(Tr-Gln)}-E-propenoate (Example 4) above: $R_f$=0.24 (60% EtOAc in hexanes); IR (cm⁻¹) 3293, 1717, 1668; ¹H NMR (CDCl₃) δ 0.82 (d, 3H, J=6.8), 1.01 (d, 3H, J=6.8), 1.30 (t, 3H, J=7.2), 1.51–1.65 (m, 2H), 1.84–1.96 (m, 1H), 2.16–2.37 (m, 2H), 2.47 (s, 3H), 2.49–2.55 (m, 3H), 2.85–3.01 (m, 2H), 3.12–3.25 (m, 3H), 3.77 (s, 3H), 3.78 (s, 3H), 4.18 (q, 2H, J=7.2), 4.31–4.49 (m, 3H), 4.65–4.70 (m, 1H), 5.53 (dd, 1H, J=15.7, 1.4), 6.39–6.44 (m, 3H), 6.63 (dd, 1H, J=15.7, 5.4), 6.93–7.01 (m, 2H), 7.05–7.10 (m, 1H), 7.12–7.18 (m, 2H), 7.24 (d, 1H, J=8.7), 7.47 (d, 1H, J=6.5); Anal. (C₄₀H₄₉FN₄O₉·0.5H₂O) C, H, N.

Preparation of Product Ethyl-3-{(5'-Methylisoxazole-3'-carbonyl)-L-ValΨ(COCH₂)-L-(4-F-Phe)-L-((S)-Pyrrol-Ala)}-E-Propenoate Ethyl-3-{Boc-L-ValΨ(COCH₂)-L-(4-F-Phe)-L-((N-2,4-dimethoxybenzyl)-(S)-Pyrrol-Ala)}-E-propenoate was converted to product ethyl-3-{(5'-methylisoxazole-3'-carbonyl)-L-ValΨ(COCH₂)-L-(4-F-Phe)-L-((S)-Pyrrol-Ala)}-E-propenoate in a manner analogous to the conversion of ethyl-3-{Boc-L-Val-L-(4-F-Phe)-L-((N-2,4-dimethoxybenzyl)-(S)-Pyrrol-Ala)}-E-propenoate to product ethyl-3-{(5'-methylisoxazole-3'-carbonyl)-L-Val-L-(4-F-Phe)-L-((S)-Pyrrol-Ala)}-E-propenoate described in Example 6 above: mp=178–181° C.; $R_f$=0.49 (10% CH₃OH in CHCl₃); IR (cm⁻¹) 3295, 1678 br; ¹H NMR (CDCl₃) δ 0.85 (d, 3H, J=6.8), 1.03 (d, 3H, J=6.5), 1.30 (t, 3H, J=7.2), 1.51–1.62 (m, 1H), 1.71–1.93 (m, 2H), 2.27–2.40 (m, 2H), 2.47 (s, 3H), 2.51–2.75 (m, 3H), 2.82–2.98 (m, 2H), 3.11–3.24 (m, 1H), 3.26–3.42 (m, 2H), 4.18 (q, 2H, J=7.2), 4.41–4.53 (m, 1H), 4.63–4.72 (m, 1H), 5.50 (d, 1H, J=15.4), 5.88 (s, 1H), 6.39 (s, 1H), 6.63 (dd, 1H, J=15.4, 5.3), 6.92–7.03 (m, 2H), 7.08–7.31 (m, 4H); Anal. (C₃₁H₃₉FN₄O₇) C, H, N.

Example 18

Preparation of Compound C-2: Ethyl-3-{(5'-Methylisoxazole-3'-carbonyl)-L-Val-O-L-(4-F-Phe)-L-((S)-Pyrrol-Ala)}-E-Propenoate

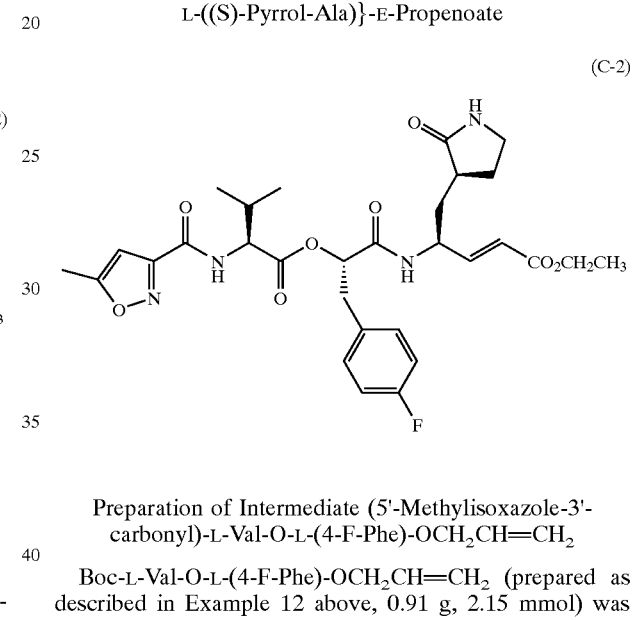

(C-2)

Preparation of Intermediate (5'-Methylisoxazole-3'-carbonyl)-L-Val-O-L-(4-F-Phe)-OCH₂CH=CH₂

Boc-L-Val-O-L-(4-F-Phe)-OCH₂CH=CH₂ (prepared as described in Example 12 above, 0.91 g, 2.15 mmol) was dissolved in 1,4-dioxane (28 mL), and a solution of HCl in 1,4-dioxane (4.0 M, 14 mL) was added. The reaction was stirred at room temperature for 14 h. The solvent was removed by evaporation, and the residue taken up in EtOAc (50 mL). The organic phase was washed with saturated NaHCO₃ solution (50 mL) and then brine (50 mL), dried (MgSO₄), and the solvent removed to give 0.66 g (quant.) of a clear oil.

This material was dissolved in CH₂Cl₂ (20 mL). Pyridine (0.17 mL, 2.08 mmol) was added, and the reaction was cooled to 0° C. 5-Methylisoxazole-3-carbonyl chloride (0.33 g, 2.27 mmol) dissolved in 2 mL of CH₂Cl₂ was added, and the reaction warmed to room temperature over 1 h. The solvent was removed in vacuo, and the residue purified by flash column chromatography eluting with a gradient of 5→10% EtOAc/hexanes. The (5'-methylisoxazole-3'-carbonyl)-L-Val-O-L-(4-F-Phe)-OCH₂CH=CH₂ product was obtained as 0.70 g (82%) of a white crystalline solid: $R_f$=0.20 (30% EtOAc/hexanes); IR (KBr) 1745, 1661, 1553, 1186 cm⁻¹; ¹H NMR (DMSO-d₆) δ 0.85–0.92 (m, 6H), 2.14–2.21 (m, 1H), 2.46 (s, 3H), 3.05–3.19 (m, 2H), 4.32–4.37 (m, 1H), 4.53–4.60 (m, 2H), 5.16–5.28 (m, 3H), 5.74–5.85 (m, 1H), 6.56 (s, 1H), 7.01–7.07 (m, 2H), 7.26–7.29 (m, 2H), 8.76 (d, 1H, J=8.1); Anal. (C₂₂H₂₅N₂O₆F) C, H, N.

83

Preparation of Intermediate Ethyl-3-{(5'-Methylisoxazole-3'-carbonyl)-L-Val-O-L-(4-F-Phe)-L-((N-2,4-Dimethoxybenzyl)-(S)-Pyrrol-Ala)}-E-Propenoate (5'-Methylisoxazole-3'-carbonyl)-L-Val-O-L-(4-F-Phe)-OCH$_2$CH=CH$_2$ (0.67 g, 1.55 mmol) was dissolved in THF (15 mL). Tetrakis(triphenylphosphine)palladium(0) (0.036 g, 0.03 mmol) was added, and the reaction mixture was stirred for 5 minutes. Morpholine (0.16 mL, 1.86 mmol) was added dropwise, and the reaction stirred at room temperature for 6 h. The solvent was removed in vacuo, and the residue taken up in 50 mL of Et$_2$O. The product was extracted twice into saturated NaHCO$_3$ solution (50 mL), and the organic phase discarded. The aqueous phase was acidified to pH=1–2 with 10% HCl, and the product extracted twice with EtOAc (40 mL). The organic phase was washed with brine (50 mL), dried (MgSO$_4$), and concentrated to give 0.57 g (95%) of an oil which crystallized upon standing.

A portion of this material (0.19 g, 0.50 mmol) was dissolved in DMF (3 mL). Diisopropylethylamine (0.34 mL, 1.0 mmol) was added, followed by ethyl-3-{H$_2$N-L-((N-2,4-dimethoxybenzyl)-(S)-pyrrol-Ala)}-E-propenoate.HCl (prepared as described in Examples 4 and 6 above, 0.19 g, 0.50 mmol). The reaction was cooled to 0° C. HATU (0.19 g, 0.50 mmol) was added, and the reaction was allowed to warm to room temperature. The DMF was removed in vacuo. The residue was dissolved with EtOAc (30 mL), and the organic phase washed consecutively with 10% HCl solution (25 mL), saturated NaHCO$_3$ solution (25 mL), H$_2$O (25 mL), and brine (25 mL). The solvent was dried (MgSO$_4$) and filtered, and the residue purified by flash column chromatography (0→1.0% MeOH/CH$_2$Cl$_2$) to give ethyl-3-{(5'-methylisoxazole-3'-carbonyl)-L-Val-O-L-(4-F-Phe)-L-((N-2,4-dimethoxybenzyl)-(S)-Pyrrol-Ala)}-E-propenoate (0.27 g, 72%) as a white amorphous solid: R$_f$=0.18 (3% MeOH/CHCl$_3$); IR(KBr) 1671, 1547, 1510, 1209 cm$^{-1}$; $^1$H NMR (DMSO-d$_6$) δ 0.88 (d, 3H, J=7.0), 0.93 (d, 3H, J=7.0), 1.20 (t, 3H, J=7.0), 1.41–1.58 (m, 2H), 1.79–1.98 (m, 2H), 2.07–2.24 (m, 2H), 2.44 (s, 3H), 3.01–3.13 (m, 4H), 3.73 (s, 3H), 3.76 (s, 3H), 4.09 (q, 2H, J=7.0), 4.24 (s, 2H), 4.30 (t, 1H, J=7.4), 4.45–4.48 (m, 1H), 5.12 (t, 1H, J=6.3), 5.59 (d, 1H, J=15.8), 6.45 (dd, 1H, J=8.5, 2.2), 6.54–6.56 (m, 2H), 6.73 (dd, 1H, J=15.5, 4.8), 6.89–6.95 (m, 3H), 7.20 (d, 1H, J=8.5), 7.22 (d, 1H, J=8.5), 8.08 (d, 1H, J=8.8), 8.89 (d, 1H, J=7.4).

Preparation of Product Ethyl-3-{(5'-Methylisoxazole-3'-carbonyl)-L-Val-O-L-(4-F-Phe)-L-((S)-Pyrrol-Ala)}-E-Propenoate Ethyl-3-{(5'-methylisoxazole-3'-carbonyl)-L-Val-O-L-(4-F-Phe)-L-((N-2,4-dimethoxybenzyl)-(S)-Pyrrol-Ala)}-E-propenoate (0.25 g, 0.33 mmol) was dissolved in CHCl$_3$ (6 mL). Two drops of water were added, followed by DDQ (0.10 g, 0.43 mmol). The reaction was heated to 50–55° C. for 8 h. Upon cooling, the reaction mixture was poured into EtOAc (30 mL). The organic phase was washed with 30 mL of 2:1 NaHCO$_3$/1N NaOH solution and then brine (30 mL), dried (MgSO$_4$), and concentrated. The residue was subjected to flash column chromatography eluting with 0→2% MeOH/CH$_2$Cl$_2$. The ethyl-3-{(5'-methylisoxazole-3'-carbonyl)-L-Val-O-L-(4-F-Phe)-L-((S)-Pyrrol-Ala)}-E-propenoate product was obtained as 0.18 g (90%) of a white amorphous solid: R$_f$=0.09 (3% MeOH/CHCl$_3$); IR(KBr) 1680, 1549 cm$^{-1}$; $^1$H NMR (DMSO-d$_6$) δ 0.91 (d, 3H, J=6.6), 0.95 (d, 3H, J=6.6), 1.20 (t, 3H, J=7.0), 1.36–1.44 (m, 1H), 1.56–1.61 (m, 1H), 1.74–1.82 (m, 1H), 1.94–1.99 (m, 2H), 2.18–2.25 (m, 1H), 2.45 (s, 3H), 2.98–3.18 (m, 4H), 4.09 (q, 2H, J=7.0), 4.28–4.32 (m, 1H), 4.43–4.46 (m, 1H), 5.12 (m, 1H), 5.58 (d, 1H, J=15.8), 6.56 (s, 1H), 6.72 (dd, 1H, J=15.8, 4.8), 6.91–6.97 (m, 2H), 7.21 (d, 1H, J=5.9), 7.23 (d, 1H, J=5.9), 7.59 (s, 1H), 8.06 (d, 1H, J=8.8), 8.92 (d, 1H, J=7.4); Anal. (C$_{30}$H$_{37}$N$_4$O$_8$F) C, H, N.

Example 19

Preparation of Compound B-3: 2-{(5'-Methylisoxazole-3'-carbonyl)-L-ValΨ(COCH$_2$)-L-(4-F-Phe)-L-((S)-Pyrrol-Ala)}-E-(α-Vinyl-γ-Butyrolactone)

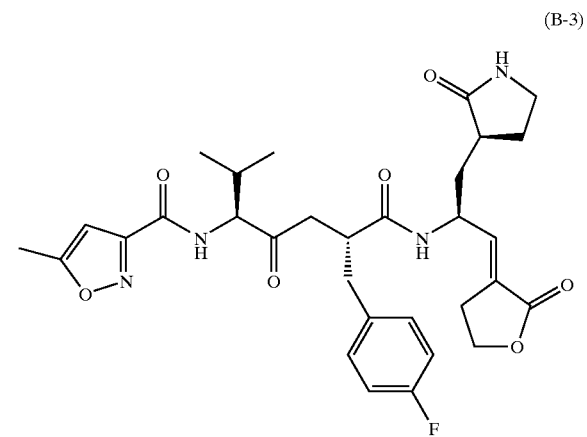

(B-3)

Preparation of Intermediate Boc-L-{(N-2,4-Dimethoxybenzyl)-(S)-Pyrrol-Ala}-E-(α-Vinyl-γ-Butyrolactone)

(1S,3'S)-{2-(1'-(2'',4''-Dimethoxybenzyl)-2'-oxo-pyrrolidin-3'-yl)-1-hydroxymethylethyl}-carbamic acid tert-butyl ester (0.360 g, 0.881 mmol, 1 equiv.) was oxidized to the corresponding aldehyde in the manner described in the preparation of ethyl-3-{Boc-L-((N-2,4-dimethoxybenzyl)-(S)-Pyrrol-Ala)}-E-propenoate (Example 6). This aldehyde was combined with 3-(triphenyl-λ$^5$-phosphanylidene)-dihydrofuran-2-one (prepared in a manner analogous to that described in Baldwin et al., *J. Org. Chem.* 1971, vol. 36, 1441) (0.320 g, 0.924 mmol, 1.05 equiv.) in a mixture of ethylene glycol dimethyl ether (10 mL) and DMF (2 mL). The reaction mixture was warmed in a 100° C. oil bath for 1.5 h, allowed to cool to 23° C. overnight, and then diluted with MTBE (200 mL), washed with water (20 mL) and brine (20 mL), dried over Na$_2$SO$_4$ and evaporated. The residue was purified by flash column chromatography (2.5% CH$_3$OH in CH$_2$Cl$_2$, then 67% EtOAc in CH$_2$Cl$_2$) to give Boc-L-{(N-2,4-dimethoxybenzyl)-(S)-Pyrrol-Ala}-E-(α-vinyl-γ-butyrolactone) as an oil (0.250 g, 60%): R$_f$=0.50 (67% EtOAc in CH$_2$Cl$_2$); IR (cm$^{-1}$) 3307, 1754, 1678; $^1$H NMR (CDCl$_3$) δ 1.42 (s, 9H), 1.46–1.68 (m, 2H), 2.02–2.13 (m, 1H), 2.18–2.30 (m, 1H), 2.44–2.56 (m, 1H), 2.91–3.04 (m, 1H), 3.15–3.27 (m, 3H), 3.80 (s, 6H), 4.34–4.43 (m, 5H), 5.63–5.69 (m, 1H), 6.42–6.47 (m, 2H), 6.48–6.53 (m, 1H), 7.09–7.13 (m, 1H).

Preparation of Product 2-{(5'-Methylisoxazole-3'-carbonyl)-L-ValΨ(COCH$_2$)-L-(4-F-Phe)-L-((S)-Pyrrol-Ala)}-E-(α-Vinyl-γ-Butyrolactone)

Boc-L-{(N-2,4-Dimethoxybenzyl)-(S)-Pyrrol-Ala}-E-(α-vinyl-γ-butyrolactone) was converted to product 2-{(5'-methylisoxazole-3'-carbonyl)-L-ValΨ(COCH$_2$)-L-(4-F-Phe)-L-((S)-Pyrrol-Ala)}-E-(α-vinyl-γ-butyrolactone) in a manner analogous to that described above for the preparation of product ethyl-3-{(5'-methylisoxazole-3'-carbonyl)-L-

ValΨ(COCH₂)-L-(4-F-Phe)-L-((S)-Pyrrol-Ala)}-E-propenoate (Example 17): $R_f$=0.28 (5% CH₃OH in CH₂Cl₂); IR (cm⁻¹) 3378 br, 1749, 1678 br; ¹H NMR (CDCl₃) δ 0.84 (d, 3H, J=6.8), 1.03 (d, 3H, J=6.8), 1.45–1.55 (m, 1H), 1.75–2.00 (m, 2H), 2.25–2.43 (m, 2H), 2.46–2.59 (m, 2H), 2.48 (s, 3H), 2.63–2.72 (m, 1H), 2.77–2.90 (m, 3H), 3.06–3.26 (m, 2H), 3.29–3.44 (m, 2H), 4.32–4.46 (m, 3H), 4.65–4.71 (m, 1H), 5.72 (s, 1H), 6.14–6.20 (m, 1H), 6.40 (s, 1H), 6.94–7.02 (m, 2H), 7.03–7.11 (m, 2H), 7.24 (d, 1H, J=9.0), 7.60 (d, 1H, J=6.2); Anal. (C₃₁H₃₇FN₄O₇) C, H, N.

Example 20

Preparation of Compound B-4: Ethyl-3-{(5'-Methylisoxazole-3'-carbonyl)-L-ValΨ(COCH₂)-L-(4-F-Phe)-L-((S)-Piper-Ala)}-E-Propenoate (B-4)

This product was prepared in analogy to product ethyl-3-{(5'-methylisoxazole-3'-carbonyl)-L-Val-L-(4-F-Phe)-L-((S)-Piper-Ala)}-E-propenoate (Example 9) and product ethyl-3-{(5'-methylisoxazole-3'-carbonyl)-L-ValΨ(COCH₂)-L-(4-F-Phe)-L-Gln}-E-propenoate (Example 10) described above: mp=161–162° C.; $R_f$=0.30 (5% CH₃OH in CH₂Cl₂); IR (cm⁻¹) 3295, 1713, 1649; ¹H NMR (CDCl₃) δ 0.84 (d, 3H, J=6.8), 1.03 (d, 3H, J=6.8), 1.30 (t, 3H, J=7.2), 1.43–1.55 (m, 2H), 1.77–1.90 (m, 2H), 1.95–2.12 (m, 2H), 2.27–2.38 (m, 1H), 2.44–2.58 (m, 2H), 2.48 (s, 3H), 2.66–2.76 (m, 1H), 2.80–2.93 (m, 2H), 3.12–3.42 (m, 3H), 4.18 (q, 2H, J=7.2), 4.39–4.49 (m, 1H), 4.65–4.72 (m, 1H), 5.50 (dd, 1H, J=15.9, 1.6), 5.80 (s, 1H), 6.38–6.41 (m, 1H), 6.62 (dd, 1H, J=15.9, 5.3), 6.94–7.02 (m, 2H), 7.08–7.28 (m, 4H).

Examples 21 through 30

For Examples 21–30, the following Compounds (A-14) through (A-23), respectively, were prepared using synthetic methods analogous to those described above for compounds of the formula I-A:

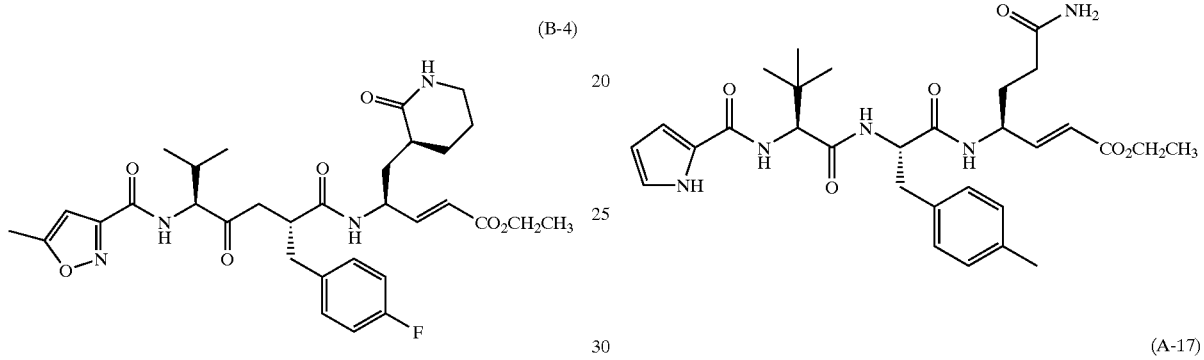

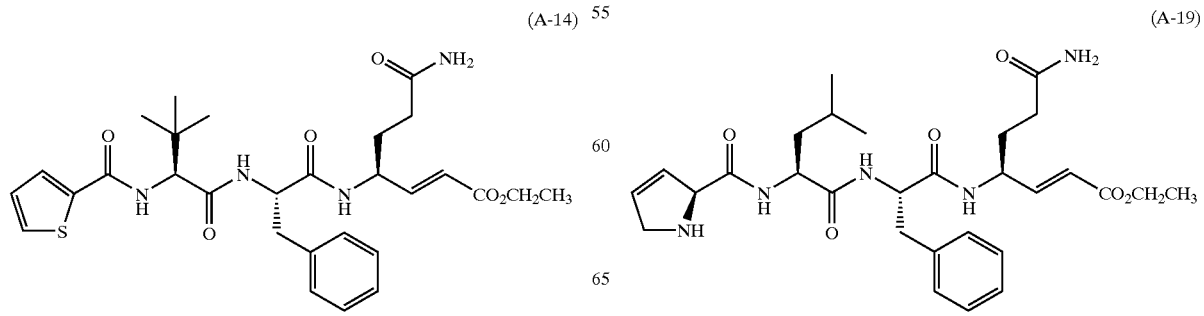

(A-20)

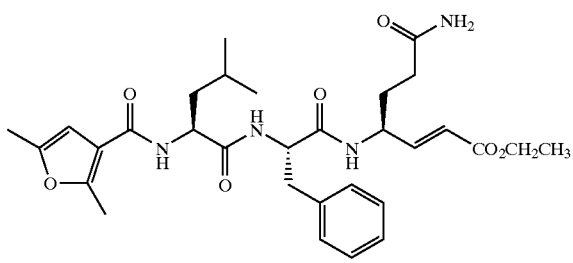

(A-21)

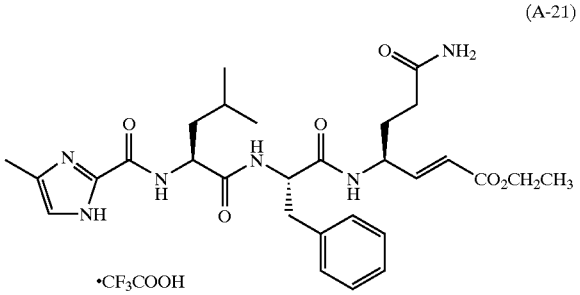

•CF₃COOH (A-22)

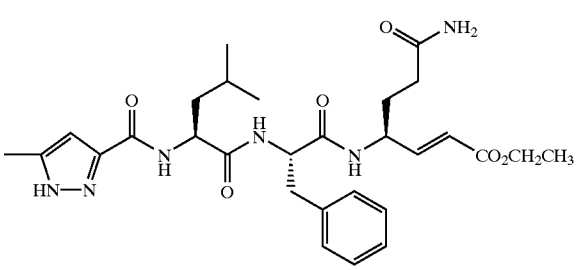

(A-23)

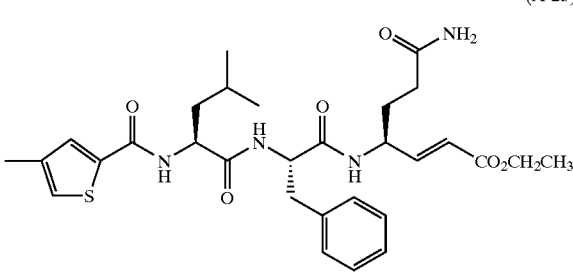

Example 31
Preparation of Comparison Compound #2: Ethyl-3-
(Cbz-L-Leu-L-Phe-L-Gln)-E-Propenoate (Comparison Compound #2)

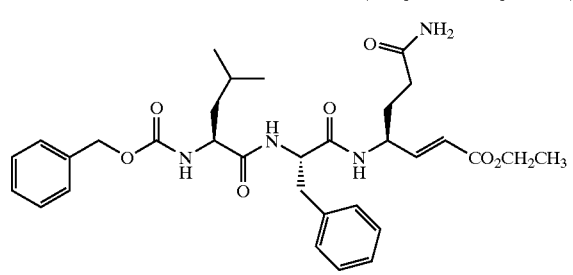

Preparation of Intermediate [Boc-L-(Tr-Gln)]—N(OMe)Me

Isobutyl chloroformate (4.77 mL, 36.8 mmol, 1.0 equiv.) was added to a solution of N-α-Boc-γ-trityl-L-glutamine (18.7 g, 36.7 mmol, 1 equiv.) and 4-methylmorpholine (8.08 mL, 73.5 mmol, 2.0 equiv.) in $CH_2Cl_2$ (250 mL) at 0° C. The reaction mixture was stirred at 0° C. for 20 minutes, and then N,O-dimethylhydroxylamine hydrochloride (3.60 g, 36.7 mmol, 1.0 equiv.) was added. The resulting solution was stirred at 0° C. for 20 minutes and at 23° C. for 2 hours, and then was partitioned between water (150 mL) and $CH_2Cl_2$ (2×150 mL). The combined organic layers were dried over $Na_2SO_4$ and were concentrated. Purification of the residue by flash column chromatography (gradient elution 40→20% hexanes in EtOAc) provided {Boc-L-(Tr-Gln)}-N(OMe)Me (16.1 g, 82%) as a white foam: IR (cm⁻) 3411, 3329, 3062, 1701, 1659; $^1$H NMR (CDCl₃) δ 1.42 (s, 9H), 1.63–1.77 (m, 1H), 2.06–2.17 (m, 1H), 2.29–2.43 (m, 2H), 3.17 (s, 3H), 3.64 (s, 3H), 4.73 (s, br, 1H), 5.38–5.41 (m, 1H), 7.20–7.31 (m, 15H); Anal. ($C_{31}H_{37}N_3O_5$) C, H, N.

Preparation of Intermediate {BOC-L-(Tr-Gln)}-H

Diisobutylaluminum hydride (50.5 mL of a 1.5 M solution in toluene, 75.8 mmol, 2.5 equiv.) was added to a solution of {Boc-L-(Tr-Gln)}-N(OMe)Me (16.1 g, 30.3 mmol, 1 equiv.) in THF at −78° C., and the reaction mixture was stirred at −78° C. for 4 h. Methanol (4 mL) and 1.0 M HCl (10 mL) were added sequentially, and the mixture was warmed to 23° C. The resulting suspension was diluted with Et₂O (150 mL) and was washed with 1.0 M HCl (3×100 mL), half-saturated NaHCO₃ (100 mL), and water (100 mL). The organic layer was dried over MgSO₄, filtered, and was concentrated to give crude {Boc-L-(Tr-Gln)}-H (13.8 g, 97%) as a white solid: mp=114–116° C.; IR (cm⁻¹) 3313, 1697, 1494; $^1$H NMR (CDCl₃) δ 1.44 (s, 9H), 1.65–1.75 (m, 1H), 2.17–2.23 (m, 1H), 2.31–2.54 (m, 2H), 4.11 (s, br, 1H), 5.38–5.40 (m, 1H), 7.11 (s, 1H), 7.16–7.36 (m, 15H), 9.45 (s, 1H).

Preparation of Intermediate Ethyl-3-{Boc-L-(Tr-Gln)}-E-Propenoate

Sodium bis(trimethylsilyl)amide (22.9 mL of a 1.0 M solution in THF, 22.9 mmol, 1.0 equiv.) was added to a solution of triethyl phosphonoacetate (5.59 g, 22.9 mmol, 1.0 equiv.) in THF (200 mL) at −78° C., and the resulting solution was stirred for 20 minutes at that temperature. Crude {Boc-L-(Tr-Gln)}-H (10.8 g, 22.9 mmol, 1 equiv.) in THF (50 mL) was added via cannula, and the reaction mixture was stirred for 2 hours at −78° C., warmed to 0° C. for 10 minutes, and partitioned between 0.5 M HCl (150 mL) and a 1:1 mixture of EtOAc and hexanes (2×150 mL). The combined organic layers were dried over Na₂SO₄ and were concentrated. Purification of the residue by flash column chromatography (40% EtOAc in hexanes) provided ethyl-3-{Boc-L-(Tr-Gln)}-E-propenoate (10.9 g, 88%) as a white foam: IR (cm⁻¹) 3321, 1710; $^1$H NMR (CDCl₃) δ 1.27 (t, 3H, J=7.2), 1.42 (s, 9H), 1.70–1.78 (m, 1H), 1.80–1.96 (m, 1H), 2.35 (t, 2H, J=7.0), 4.18 (q, 2H, J=7.2), 4.29 (s, br, 1H), 4.82–4.84 (m, 1H), 5.88 (dd, 1H, J=15.7, 1.6), 6.79 (dd, 1H, J=15.7, 5.3), 6.92 (s, 1H), 7.19–7.34 (m, 15H); Anal. ($C_{33}H_{38}N_2O_5$) C, H, N.

Preparation of Intermediate Ethyl-3-{Cbz-L-Leu-L-Phe-L-(Tr-Gln)}-E-Propenoate

A solution of HCl in 1,4-dioxane (4.0 M, 20 mL), was added to a solution of ethyl-3-{Boc-L-(Tr-Gln)}-E-propenoate (1.00 g, 1.84 mmol, 1 equiv.) in the same solvent (20 mL) at 23° C. After 3 hours, the volatiles were removed under reduced pressure. The residue was dissolved in $CH_2Cl_2$ (50 mL) and Cbz-L-Leu-L-Phe-OH (0.759 g, 1.84 mmol, 1.0 equiv.), HOBt (0.373 g, 2.76 mmol, 1.5 equiv.), 4-methylmorpholine (0.809 mL, 7.36 mmol, 4.0 equiv.), and EDC (0.529 g, 2.76 mmol, 1.5 equiv.) were added sequentially. The reaction mixture was stirred at 23° C. for 18 hours, and then was partitioned between water (150 mL) and EtOAc (2×150 mL). The combined organic layers were dried over $Na_2SO_4$ and were concentrated. Flash chromatographic purification of the residue (5% $CH_3OH$ in $CH_2Cl_2$) afforded ethyl-3-{Cbz-L-Leu-L-Phe-L-(Tr-Gln)}-E-propenoate (1.25 g, 83%) as a white solid: mp=192–194° C.; IR (cm$^{-1}$) 3295, 1696, 1678, 1655, 1519; $^1$H NMR (CDCl$_3$) δ 0.84 (d, 3H, J=6.5), 0.86 (d, 3H, J=6.5), 1.24–1.32 (m, 1H), 1.28 (t, 3H, J=7.2), 1.43–1.75 (m, 3H), 1.91–2.06 (m, 1H), 2.20–2.38 (m, 2H), 2.93–3.02 (m, 1H), 3.07–3.18 (m, 1H), 3.95–4.02 (m, 1H), 4.17 (q, 2H, J=7.2), 4.43–4.55 (m, 2H), 4.82–4.95 (m, 2H), 5.69 (d, 1H, J=15.7), 6.46 (d, 1H, J=7.5), 6.60 (d, 1H, J=8.1), 6.69 (dd, 1H, J=15.7, 5.1), 7.09–7.38 (m, 27H); Anal. ($C_{51}H_{56}N_4O_7$) C, H, N.

Preparation of Product Ethyl-3-(Cbz-L-Leu-L-Phe-L-Gln)-E-Propenoate

Trifluoroacetic acid (20 mL) was added to a solution of ethyl-3-{Cbz-LLeu-L-Phe-L-(Tr-Gln)}-E-propenoate (1.25 g, 1.49 mmol, 1 equiv.) and triisopropylsilane (1.53 mL, 7.47 mmol, 5.0 equiv.) in $CH_2Cl_2$ (20 mL) at 23° C., producing a bright yellow solution. The reaction mixture was stirred for 20 minutes at 23° C., during which time it became colorless. Carbon tetrachloride (20 mL) was added, and the volatiles were removed under reduced pressure. The residue was triturated with $Et_2O$ (20 mL), and the resulting white solid was collected by vacuum filtration, washed with $Et_2O$ (3×50 mL), and air-dried to afford ethyl-3-(Cbz-L-Leu-L-Phe-L-Gln)-E-propenoate (0.717 g, 81%): mp=219–221° C.; IR (cm$^{-1}$) 3300, 1672, 1535; $^1$H NMR (DMSO-d$_6$) δ 0.78 (d, 3H, J=6.8), 0.82 (d, 3H, J=6.5), 1.21 (t, 3H, J=7.0), 1.25–1.37 (m, 2H), 1.42–1.54 (m, 1H), 1.58–1.80 (m, 2H), 2.02–2.09 (m, 2H), 2.84 (dd, 1H, J=13.2, 8.9), 2.97 (dd, 1H, J=13.2, 5.8), 3.93–4.01 (m, 1H), 4.11 (q, 2H, J=7.0), 4.33–4.52 (m, 2H), 4.97 (d, 1H, J=12.3), 5.04 (d, 1H, J=12.3), 5.64 (d, 1H, J=15.9), 6.69 (dd, 1H, J=15.9, 5.4), 6.76 (s, 1H), 7.13–7.37 (m, 11H), 7.43 (d, 1H, J=7.8), 7.99 (d, 1H, J=8.1), 8.04 (d, 1H, J=8.1); Anal. ($C_{32}H_{42}N_4O_7$) C, H, N.

Example 32

Preparation of Comparison Compound #3: Ethyl-3-(Cbz-L-Val-L-Phe-L-Gln)-E-Propenoate (Comparison Compound #3)

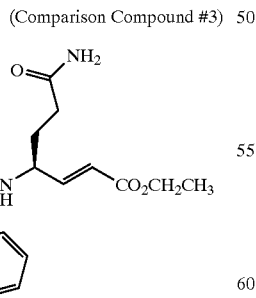

Preparation of Intermediate Ethyl-3-{Boc-L-Phe-L-(Tr-Gln)}-E-Propenoate

A solution of HCl in 1,4-dioxane (4.0 M, 10 mL) was added to a solution of ethyl-3-{Boc-L-(Tr-Gln)}-E-propenoate (prepared as described in Example 31, 3.05 g, 5.62 mmol, 1 equiv.) in the same solvent (20 mL) at 23° C. After 3 hours, the volatiles were removed under reduced pressure. The residue was dissolved in $CH_2Cl_2$ (50 mL), and Boc-L-Phe-OH (1.49 g, 5.62 mmol, 1.0 equiv.), HOBt (0.911 g, 6.74 mmol, 1.2 equiv.), 4-methylmorpholine (1.85 mL, 16.8 mmol, 3.0 equiv.) and EDC (1.29 g, 6.73 mmol, 1.2 equiv.) were added sequentially. The reaction mixture was stirred at 23° C. for 18 hours, and was then partitioned between water (150 mL) and EtOAc (2×150 mL). The combined organic layers were dried over $Na_2SO_4$ and were concentrated. Flash chromatographic purification of the residue (gradient elution, 40→50% EtOAc in hexanes) afforded ethyl-3-{Boc-L-Phe-L-(Tr-Gln)}-E-propenoate (2.77 g, 71%) as a white foam: IR (cm$^{-1}$) 3306, 1706, 1661; $^1$H NMR (CDCl$_3$) δ 1.29 (t, 3H, J=7.2), 1.38 (s, 9H), 1.65–1.76 (m, 1H), 1.87–1.99 (m, 1H), 2.25–2.27 (m, 2H), 2.94–3.01 (m, 2H), 4.14–4.26 (m, 3H), 4.48–4.53 (m, 1H), 4.95 (s, br, 1H), 5.64 (d, 1H, J=15.8), 6.29 (d, 1H, J=8.1), 6.64 (dd, 1H, J=15.8, 5.4), 6.80 (s, br, 1H), 7.14–7.32 (m, 20H); Anal. ($C_{42}H_{47}N_3O_6$) C, H, N.

Preparation of Intermediate Ethyl-3-{Cbz-L-Val-L-Phe-L-(Tr-Gln)}-E-Propenoate

A solution of HCl in 1,4-dioxane (4.0 M, 8 mL) was added to a solution of ethyl-3-{Boc-L-Phe-L-(Tr-Gln)}-E-propenoate (0.296 g, 0.429 mmol, 1 equiv.) in the same solvent (10 mL) at 23° C. After 3 hours, the volatiles were removed under reduced pressure. The residue was dissolved in $CH_2Cl_2$ (10 mL), and then Cbz-L-Val-OH (0.108 g, 0.430 mmol, 1.0 equiv.), HOBt (0.070 g, 0.518 mmol, 1.2 equiv.), 4-methylmorpholine (0.142 mL, 1.29 mmol, 3.0 equiv.) and EDC (0.099 g, 0.516 mmol, 1.2 equiv.) were added sequentially. The reaction mixture was stirred at 23° C. for 4 hours, and then was partitioned between water (100 mL) and EtOAc (2×100 mL). The combined organic layers were dried over $Na_2SO_4$ and were concentrated. Flash chromatographic purification of the residue (3% $CH_3OH$ in $CH_2Cl_2$) afforded ethyl-3-{Cbz-L-Val-L-Phe-L-(Tr-Gln)}-E-propenoate (0.220 g, 62%) as a white solid: mp=195–198° C.; IR (cm$^{-1}$) 3284, 1689, 1646; $^1$H NMR (CDCl$_3$) δ 0.69 (d, 3H, J=6.9), 0.82 (d, 3H, J=6.5), 1.28 (t, 3H, J=7.2), 1.63–1.74 (m, 1H), 1.96–2.02 (m, 2H), 2.22–2.35 (m, 2H), 2.93 (dd, 1H, J=14.0, 7.6), 3.10 (dd, 1H, J=14.0, 6.7), 3.81–3.85 (m, 1H), 4.17 (q, 2H, J=7.2), 4.48–4.58 (m, 2H), 4.87 (d, 1H, J=12.0), 4.94 (d, 1H, J=12.0), 5.06 (d, 1H, J=6.9), 5.67 (d, 1H, J=15.6), 6.43 (d, 1H, J=7.5), 6.63–6.72 (m, 2H), 7.10–7.40 (m, 26H); Anal. ($C_{50}H_{54}N_4O_7$) C, H, N.

Preparation of Product Ethyl-3-(Cbz-L-Val-L-Phe-L-Gln)-E-Propenoate

Trifluoroacetic acid (5 mL) was added to a solution of ethyl-3-{Cbz-L-Val-L-Phe-L-(Tr-Gln)}-E-propenoate (0.188 g, 0.229 mmol, 1 equiv.) and triisopropylsilane (0.300 mL, 1.46 mmol, 6.4 equiv.) in $CH_2Cl_2$ (10 mL) at 23° C., producing a bright yellow solution. The reaction mixture was stirred for 20 min. at 23° C., during which time it became colorless. Carbon tetrachloride (10 mL) was added, and the volatiles were removed under reduced pressure. The residue was triturated with $Et_2O$ (20 mL), and the resulting white solid was collected by vacuum filtration, washed with $Et_2O$ (3×50 mL), and air-dried to afford ethyl-3-(Cbz-L-Val-L-Phe-L-Gln)-E-propenoate (0.094 g, 71%): mp=240° C. (dec); IR (cm$^{-1}$) 3263, 1686, 1640; $^1$H NMR (DMSO-d$_6$) δ 0.73 (d, 6H, J=6.9), 1.21 (t, 3H, J=7.2), 1.60–1.75 (m, 2H), 1.83–1.90 (m, 1H), 2.03–2.08 (m, 2H), 2.83 (dd, 1H, J 13.6, 8.6), 2.96 (dd, 1H, J=13.6, 6.2), 3.79–3.84 (m, 1H), 4.10 (q, 2H, J=7.2), 4.37–4.49 (m, 1H), 4.51–4.56 (m, 1H), 4.99 (d, 1H, J=12.5), 5.06 (d, 1H, J=12.5), 5.61 (d, 1H, J=15.5), 6.67 (dd, 1H, J=15.5, 5.5), 6.76 (s, 1H), 7.13–7.36 (m, 12H, 8.06 (d, 2H, J=8.1); Anal. ($C_{31}H_{40}N_4O_7$) C, H, N.

Example 33

Preparation of Compound (A-24): Ethyl-3-{Cbz-L-Leu-L-Phe-L-((S)-Pyrrol-Ala)}-E-Propenoate (A-24)

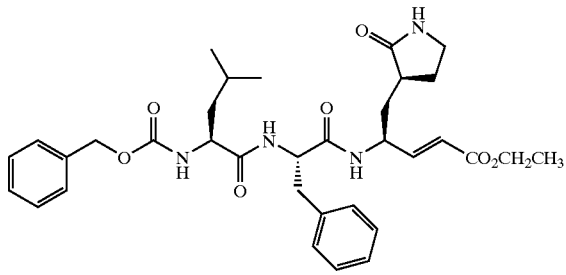

Preparation of Intermediate Ethyl-3-{Cbz-L-Phe-L-((N-2,4-Dimethoxybenzyl)(S)-Pyrrol-Ala)}-E-Propenoate A solution of HCl in 1,4-dioxane (4.0 M, 4 mL) was added to a solution of ethyl-3-{Boc-L-((N-2,4-dimethoxybenzyl)-(S)-pyrrol-Ala)}-E-propenoate (prepared as described in Example 6) (0.139 g, 0.292 mmol, 1 equiv.) in 1,4-dioxane (4 mL). After stirring 1.5 h, the volatiles were evaporated to give the crude amine salt, which was used without purification.

This amine salt was dissolved in $CH_2Cl_2$ (7 mL), and then Cbz-L-Leu-L-Phe-OH (0.156 g, 0.378 mmol, 1.3 equiv.), 4-methylmorpholine (0.128 mL, 1.16 mmol, 4 equiv.), HOBt (0.067 g, 0.50 mmol, 1.7 equiv.) and EDC (0.095 g, 0.50 mmol, 1.7 equiv) were added sequentially. After stirring 20 hours, the reaction mixture was poured into brine (15 mL) and extracted with 10% $CH_3OH$ in $CH_2Cl_2$ (3×25 mL). The combined organic phases were dried over $Na_2SO_4$ and evaporated. Purification of the residue by flash column chromatography (60% EtOAc in hexanes) provided ethyl-3-{Cbz-L-Leu-L-Phe-L-((N-2,4-dimethoxybenzyl)-(S)-Pyrrol-Ala)}-E-propenoate (0.158 g, 70%) as a foam: $^1$H NMR (CDCl$_3$) δ 0.87–0.92 (m, 6H), 1.28 (t, 3H, J=7.2), 1.46–1.68 (m, 5H), 1.74–1.86 (m, 1H), 1.97–2.19 (m, 2H), 3.02 (dd, 1H, J=13.7, 5.6), 3.11–3.24 (m, 3H), 3.78 (s, 3H), 3.79 (s, 3H), 4.17 (q, 2H, J=7.2), 4.20–4.30 (m, 2H), 4.35–4.45 (m, 2H), 4.82–4.90 (m, 1H), 5.07 (d, 1H, J=12.3), 5.13 (d, 1H, J=12.3), 5.36 (d, 1H, J=7.8), 5.82 (dd, 1H, J=15.6, 1.2), 6.42–6.46 (m, 2H), 6.72 (dd, 1H, J=15.6, 5.3), 6.88 (d, 1H, J=8.7), 7.09 (d, 1H, J=9.0), 7.13–7.20 (m, 5H), 7.29–7.37 (m, 5H), 8.09 (d, 1H, J=6.5).

Preparation of Product Ethyl-3-{Cbz-L-Leu-L-Phe-L-((S)-Pyrrol-Ala)}-E-Propenoate Ethyl-3-{Cbz-L-Leu-L-Phe-L-((N-2,4-dimethoxybenzyl)-(S)-Pyrrol-Ala)}-E-propenoate (0.156 g, 0.202 mmol, 1 equiv.) and ammonium cerium(IV) nitrate (0.277 g, 0.505 mmol, 2.5 equiv.) were combined in a mixture of THF/water 2:1 (3 mL) and stirred 2 hours. The reaction mixture was poured into brine (15 mL) and extracted with 10% $CH_3OH$ in $CH_2Cl_2$ (3×25 mL). The combined organic phases were dried over $Na_2SO_4$ and evaporated. Purification of the residue by flash column chromatography (gradient elution, 2→5% $CH_3OH$ in $CH_2Cl_2$) provided ethyl-3-{Cbz-L-Leu-L-Phe-L-((S)-Pyrrol-Ala)}-E-propenoate (0.059 g, 47%) as an off-white solid: $^1$H NMR (CDCl$_3$) δ 0.85–0.92 (m, 6H), 1.28 (t, 3H, J=7.2), 1.39–1.65 (m, 4H), 1.68–1.93 (m, 2H), 2.08–2.20 (m, 1H), 2.27–2.38 (m, 1H), 3.02–3.13 (m, 2H), 3.24–3.32 (m, 2H), 4.11–4.20 (m, 1H), 4.18 (q, 2H, J=7.2), 4.47–4.58 (m, 1H), 4.81–4.89 (m, 1H), 5.05 (d, 1H, J=12.1), 5.12 (d, 1H, J=12.1), 5.26 (d, 1H, J=8.1), 5.78 (dd, 1H, J=15.7, 1.2), 6.23 (s, 1H), 6.72 (dd, 1H, J=15.7, 5.3), 7.13–7.25 (m, 6H), 7.30–7.37 (m, 5H), 7.54 (d, 1H, J=7.2).

Example 34

Preparation of Compound (A-25): Ethyl-3-{Cbz-L-Val-L-Phe-L-((S)-Pyrrol-Ala)}-E-Propenoate (A-25)

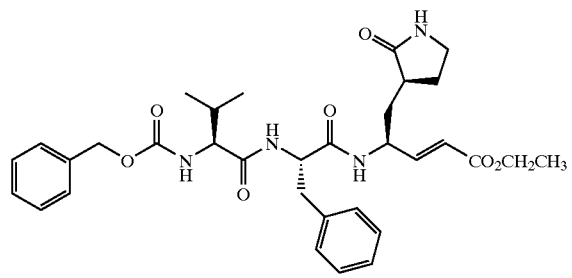

Preparation of Intermediate Ethyl-3-{Cbz-L-Val-L-Phe-L-((N-2,4-Dimethoxybenzyl)-(S)-Pyrrol-Ala)}-E-Propenoate In a manner analogous to that used for the conversion of ethyl-3-{Boc-L-(Tr-Gln)}-E-propenoate to ethyl-3-{Cbz-L-Leu-L-Phe-L-(Tr-Gln)}-E-propenoate described in Example 31, ethyl-3-{Boc-L-((N-2,4-dimethoxybenzyl)-(S)-Pyrrol-Ala)}-E-propenoate (prepared as in Example 33) was coupled with Cbz-L-Val-L-Phe-OH to afford ethyl-3-{Cbz-L-Val-L-Phe-L-((N-2,4-dimethoxybenzyl)-(S)-Pyrrol-Ala)}-E-propenoate: IR (cm$^1$) 3288, 1699,1652; $^1$H NMR (CDCl$_3$) δ 0.87 (d, 3H, J=6.8), 0.95 (d, 3H, J=6.5), 1.28 (t, 3H, J=7.2), 1.48–1.60 (m, 2H), 1.70–1.84 (m, 1H), 1.95–2.20 (m, 3H), 3.01 (dd, 1H, J=13.4, 5.6), 3.09–3.25 (m, 3H), 3.78 (s, 3H), 3.80 (s, 3H), 4.03–4.10 (m, 1H), 4.17 (q, 2H, J=7.2), 4.24 (d, 1H, J=14.2), 4.33–4.44 (m, 1H), 4.38 (d, 1H, J=14.2), 4.85–4.94 (m, 1H), 5.08 (d, 1H, J=12.1), 5.14 (d, 1H, J=12.1), 5.39 (d, 1H, J=8.1), 5.80 (dd, 1H, J=15.6, 1.2), 6.42–6.47 (m, 2H), 6.70 (dd, 1H, J=15.6, 5.3), 6.81 (d, 1H, J=9.0), 7.11–7.20 (m, 6H), 7.31–7.39 (m, 5H), 8.11 (d, 1H, J=6.2); Anal. ($C_{42}H_{52}N_4O_9$) C, H, N.

Preparation of Product Ethyl-3-{Cbz-L-Val-L-Phe-L-((S)-Pyrrol-Ala)}-E-Propenoate A suspension of ethyl-3-{Cbz-L-Val-L-Phe-L-((N-2,4-dimethoxybenzyl)-(S)-Pyrrol-Ala)}-E-propenoate (0.215 g, 0.284 mmol, 1 equiv.), DDQ (0.071 g. 0.31 mmol, 1.1 equiv.) and water (3 drops) in CHCl$_3$ (4 mL) was stirred 1 h at 23° C., and was then warmed to reflux for 6 h. After cooling overnight, more DDQ (0.019 g, 0.084 mmol, 0.3 equiv.) was added, and the mixture was warmed to 67° C. for 1 h and then evaporated. Purification of the residue by flash column chromatography (gradient elution, 2→5% $CH_3OH$ in $CH_2Cl_2$) provided slightly impure material, which was dissolved in CH$_2$Cl$_2$ (70 mL) and washed with saturated NaHCO$_3$ (2×30 mL) and brine (30 mL), and then dried over Na$_2$SO$_4$ and evaporated. The residue was stirred in Et$_2$O (10 mL) for 20 minutes, and the solid was collected by filtration and dried under vacuum to provide ethyl-3-{Cbz-L-Phe-L-((S)-Pyrrol-Ala)}-E-propenoate (0.060 g, 35%) as a an off-white solid: mp=215–217° C.; IR (cm$^{-1}$) 3413, 3295, 1696, 1649; $^1$H NMR (CDCl$_3$) δ 0.83 (d, 3H, J=6.5), 0.91 (d, 3H, J=6.8), 1.28 (t, 3H, J=7.2), 1.50–1.59 (m, 1H), 1.70–1.91 (m, 2H), 2.03–2.17 (m, 2H), 2.26–2.38 (m, 1H), 3.03 (dd, 1H, J=13.5, 6.4), 3.12 (dd, 1H, J=13.5, 6.4), 3.21–3.34 (m, 2H), 3.96 (dd, 1H, J=8.3, 6.4), 4.17 (q, 2H, J=7.2), 4.45–4.56 (m, 1H), 4.83–4.92 (m, 1H), 5.07 (d, 1H, J=12.1), 5.13 (d, 1H, J=12.1), 5.29 (d, 1H, J=8.3), 5.77 (dd, 1H, J=15.8, 1.2), 5.94 (s, 1H), 6.71 (dd, 1H, J=15.8, 5.3), 6.95 (d, 1H, J=9.0), 7.14–7.27 (m, 5H), 7.31–7.38 (m, 5H), 7.57 (d, 1H, J=7.2); Anal. (C$_{33}$H$_{42}$N$_4$O$_7$) C, H, N.

Example 35

Preparation of Compound (A-26): Ethyl-3-{Cbz-L-Leu-L-Phe-L-((S)-Piper-Ala)}-E-Propenoate

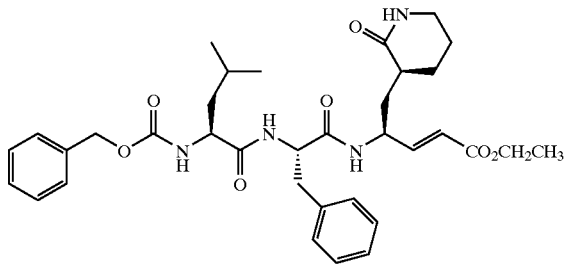

(A-26)

Preparation of Product Ethyl-3-{Cbz-L-Leu-L-Phe-L-((S)-Piper-Ala)}-E-Propenoate (1S,3'S)-{2-(1'-(2'',4''-Dimethoxybenzyl)-2'-oxo-piperidin-3'-yl)-1-hydroxy-methylethyl}-carbamic acid tert-butyl ester (prepared as described in Example 8) was converted to the product ethyl-3-{Cbz-L-Leu-L-Phe-L-((S)-Piper-Ala)}-E-propenoate in a manner analogous to the conversion of (1S,3'S)-{2-(1'-(2'',4''-dimethoxybenzyl)-2'-oxo-pyrrolidin-3'-yl)-1-hydroxymethyl-ethyl}-carbamic acid tert-butyl ester to product ethyl-3-{Cbz-L-Leu-L-Phe-L-((S)-Pyrrol-Ala)}-E-propenoate as described in Example 34: IR (cm$^{-1}$) 3422, 3307, 1713, 1649; $^1$H NMR (CDCl$_3$) δ 0.86–0.92 (m, 6H), 1.28 (t, 3H, J=7.2), 1.38–1.75 (m, 6H), 1.77–1.89 (m, 1H), 1.96–2.11 (m, 2H), 3.07 (d, 2H, J=6.2), 3.20–3.27 (m, 2H), 4.13–4.24 (m, 1H), 4.18 (q, 2H, J=7.2), 4.41–4.53 (m, 1H), 4.76–4.85 (m, 1H), 5.06 (d, 1H, J=12.1), 5.12 (d, 1H, J=12.1), 5.34 (d, 1H, J=7.8), 5.78 (dd, 1H, J=15.6, 5.4), 6.17 (s, 1H), 6.70 (dd, 1H, J=15.6, 5.4), 7.00 (d, 1H, J=8.4), 7.13–7.27 (m, 6H), 7.30–7.37 (m, 5H), 7.83 (d, 1H, J=6.8); Anal. (C$_{35}$H$_{46}$N$_4$O$_7$·0.5H$_2$O) C, H, N.

Example 36

Preparation of Compound (A-27): Ethyl-3-{Cbz-L-Leu-L-Phe-L-((R)-Pyrrol-Ala)}-E-Propenoate

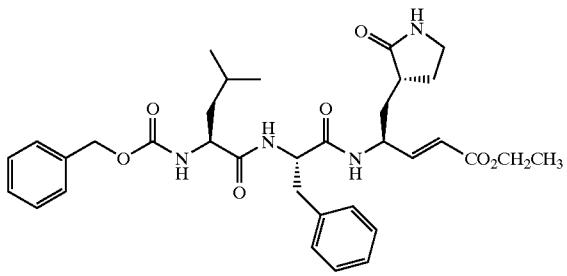

(A-27)

Preparation of Intermediate (4S,4''R)-4-{3'-(4''-Benzyl-2''-oxo-oxazolidin-3''-yl)-3'-oxopropyl}-2,2-dimethyloxazolidine-3-carboxylic Acid tert-Butyl Ester Triethylamine (6.43 mL, 46.1 mmol, 3.0 equiv.) and pivaloyl chloride (1.89 mL, 15.3 mmol, 1.0 equiv.) were added sequentially to a solution of (4S)-4-(2'-carboxyethyl)-2,2-dimethyloxazolidine-3-carboxylic acid tert-butyl ester (4.20 g, 15.3 mmol, 1 equiv.) in THF (300 mL) at 0° C. The cloudy reaction mixture was stirred at 0° C. for 3.5 h, and then lithium chloride (0.716 g, 16.9 mmol, 1.1 equiv.) and (R)-(+)-4-benzyl-2-oxazolidinone (2.59 g, 14.6 mmol, 0.95 equiv.) were added sequentially. After warming to 23° C. and stirring for 19 h, the reaction mixture was partitioned between 0.5 M HCl (150 mL) and EtOAc (2×150 mL). The combined organic layers were washed with half-saturated Na$_2$CO$_3$ (150 mL), dried over MgSO$_4$, and gravity filtered. The filtrate was concentrated under reduced pressure and the residue was purified by flash column chromatography (30% EtOAc in hexanes) to give (4S,4''R)-4-{3'-(4''-benzyl-2''-oxo-oxazolidin-3''-yl)-3'-oxopropyl}-2,2-dimethyloxazolidine-3-carboxylic acid tert-butyl ester (6.15 g, 97%) as a colorless oil: IR (cm$^{-1}$) 2978, 1783, 1694; $^1$H NMR (CDCl$_3$, mixture of isomers) δ 1.46 (s), 1.58 (s), 1.63 (s), 2.01–2.05 (m), 2.72–3.13 (m), 3.29–3.33 (m), 3.74–3.79 (m), 3.82–4.09 (m), 4.11–4.25 (m), 4.67–4.70 (m), 7.20–7.37 (m); Anal. (C$_{23}$H$_{32}$N$_2$O$_6$) C, H, N.

Preparation of Intermediate (2'R,4S,4''R)-4-{2'-(4''-Benzyl-2''-oxo-oxazolidine-3''-carbonyl)-pent-4'-enyl}-2,2-dimethyloxazolidine-3-carboxylic Acid tert-Butyl Ester A solution of (4S,4''R)-4-{3'-(4''-benzyl-2''-oxo-oxazolidin-3'-yl)-3'-oxopropyl}-2,2-dimethyloxazolidine-3-carboxylic acid tert-butyl ester (6.15 g, 14.2 mmol, 1 equiv.) in THF (25 mL) was added to a solution of sodium bis(trimethylsilyl)amide (14.2 mL of a 1.0 M solution in THF, 14.2 mmol, 1.0 equiv.) in the same solvent (50 mL) at −78° C. The reaction mixture was stirred for 15 minutes at −78° C., and then allyl iodide (3.90 mL, 42.6 mmol, 3.0 equiv.) was added. After stirring an additional 2 h at −78° C., the reaction mixture was maintained at −45° C. for 2 h, and then was partitioned between a 2:1 mixture of half-saturated NH$_4$Cl and 5% Na$_2$S$_2$O$_3$ (200 mL) and a 1:1 mixture of EtOAc and hexanes (2×150 mL). The combined organic layers were washed with H$_2$O (100 mL), dried over MgSO$_4$, and gravity filtered. The filtrate was concentrated under reduced pressure and the residue was purified by flash column chromatography (15% EtOAc in hexanes) to provide (2'R,4S,4"R)-4-{2'-(4"-benzyl-2"-oxo-oxazolidine-3"-carbonyl)-pent-4'-enyl}-2,2-dimethyloxazolidine-3-carboxylic acid tert-butyl ester (3.12 g, 46%) as a viscous foam: IR (cm$^{-1}$) 2978, 1782, 1685; $^1$H NMR (CDCl$_3$, mixture of isomers) δ 1.42 (s), 1.45 (s), 1.49 (s), 1.52 (s), 1.62–1.78 (m), 1.80–2.01 (m), 2.23–2.49 (m), 2.51–2.56 (m), 2.76 (dd, J=13.3, 9.7), 3.26 (dd, J=13.3, 3.6), 3.58–3.64 (m), 3.67 (d, J=8.7), 3.90–3.98 (m), 4.02–4.15 (m), 4.16–4.30 (m), 4.75–4.82 (m), 5.06–5.11 (m), 5.74–5.88 (m), 7.22–7.36 (m); Anal. (C$_{26}$H$_{36}$N$_2$O$_6$) C, H, N.

Preparation of Intermediate (1S,3'R)-{2-(1'-(2",4"-Dimethoxybenzyl)-2'-oxo-pyrrolidin-3'-yl)-1-hydroxymethylethyl}-carbamic Acid tert-Butyl Ester Ozone was bubbled through a solution of (2'R,4S,4"R)-4-{2'-(4"-benzyl-2"-oxo-oxazolidine-3"-carbonyl)-pent-4'-enyl}-2,2-dimethyloxazolidine-3-carboxylic acid tert-butyl ester (3.12 g, 6.60 mmol, 1 equiv.) in CH$_2$Cl$_2$ (200 mL) and CH$_3$OH (0.535 mL, 13.2 mmol, 2.0 equiv.) at −78° C. until a blue color persisted. The reaction mixture was then purged with argon until it became colorless. Methyl sulfide (4.85 mL, 66.0 mmol, 10 equiv.) was added, and the mixture was stirred at −78° C. for 3.5 h and then was maintained at 0° C. for an additional 1 h. After partitioning the reaction mixture between H$_2$O (150 mL) and a 1:1 mixture of EtOAc and hexanes (2×150 mL), the combined organic layers were dried over MgSO$_4$ and gravity filtered. The filtrate was concentrated under reduced pressure, and the residue was immediately utilized without further purification.

The above residue was dissolved in a 2:1 mixture of THF, and then EtOH (180 mL) at 23° C. and 2,4-dimethoxybenzylamine hydrochloride (5.38 g, 26.4 mmol, 4.0 equiv.), sodium acetate (2.17 g, 26.4 mmol, 4.0 equiv.), and sodium cyanoborohydride (0.829 g, 13.2 mmol, 2.0 equiv.) were added sequentially. The resulting suspension was stirred for 19 h at 23° C., and then was partitioned between 0.5 M HCl (150 mL) and EtOAc (2×100 mL). The combined organic layers were washed with half-saturated NaHCO$_3$ (100 mL), dried over Na$_2$SO$_4$, and concentrated under reduced pressure. The residue was passed through a short silica gel column (eluting with 50% EtOAc in hexanes) to give (3'R,4S)-4-{1'-(2",4"-dimethoxybenzyl)-2'-oxo-pyrrolidin-3'ylmethyl}-2,2-dimethyl-oxazolidine-3-carboxylic acid tert-butyl ester contaminated with (R)-(+)-4-benzyl-2-oxazolidinone.

This material was dissolved in CH$_3$OH (80 mL), and TsOH.H$_2$O (0.251 g, 1.32 mmol, 0.20 equiv.) was added. The reaction mixture was heated to 50° C. and was maintained at that temperature for 4 h. After cooling to 23° C., the reaction mixture was concentrated under reduced pressure to ~20 mL volume and was partitioned between half-saturated NaHCO$_3$ (150 mL) and a 9:1 mixture of CH$_2$Cl$_2$ and CH$_3$OH (2×150 mL). The combined organic layers were dried over Na$_2$SO$_4$ and concentrated under reduced pressure. Purification of the residue by flash column chromatography (3% CH$_3$OH in CH$_2$Cl$_2$) afforded (1S,3'R)-{2-(1'-(2",4"-dimethoxybenzyl)-2'-oxo-pyrrolidin-3'-yl)-1-hydroxymethylethyl}-carbamic acid tert-butyl ester (0.92 g, 34%) as a foam: IR (cm$^{-1}$) 3347 (br), 2937, 1669; $^1$H NMR (CDCl$_3$) δ 1.44 (s, 9H), 1.62–1.77 (m, 2H), 1.94–2.04 (m, 1H), 2.15–2.26 (m, 1H), 2.40–2.50 (m, 1H), 3.13–3.24 (m, 2H), 3.56–3.77 (m, 3H), 3.80 (s, 6H), 3.82–4.16 (m, 1H), 4.37 (d, 1H, J=14.3), 4.45 (d, 1H, J=14.3), 5.49 (d, 1H, J=7.8), 6.42–6.45 (m, 2H), 7.08–7.11 (m, 1H); Anal. (C$_{21}$H$_{32}$N$_2$O$_6$.0.25H$_2$O) C, H, N.

Preparation of Intermediate Ethyl-3-{Boc-L-((N-2,4-Dimethoxybenzyl)-(R)-Pyrrol-Ala)}-E-Propenoate In a manner analogous to the conversion of (1S,3'S)-{2-(1'-(2",4"-dimethoxybenzyl)-2'-oxo-pyrrolidin-3'-yl}1-hydroxymethylethyl}carbamic acid tert-butyl ester to ethyl-3-{Boc-L-((N-2,4-dimethoxybenzyl)-(S)-Pyrrol-Ala)}-E-propenoate described in Example 33, (1S,3'R){2-(1'(2",4"-dimethoxybenzyl)-2'-oxo-pyrrolidin-3'-yl)-1-hydroxymethylethyl}-carbamic acid tert-butyl ester was transformed into ethyl-3-{Boc-L-(N-2,4-dimethoxybenzyl)-(R)-Pyrrol-Ala)}-E-propenoate: IR (cm$^{-1}$) 3307, 1713, 1674; $^1$H NMR (CDCl$_3$) δ 1.28 (t, 3H, J=7.2), 1.45 (s, 9H), 1.57–1.82 (m, 2H), 2.02–2.19 (m, 2H), 2.42–2.55 (m, 1H), 3.11–3.25 (m, 2H), 3.79 (s, 3H), 3.80 (s, 3H), 4.19 (q, 2H, J=7.2), 4.32–4.50 (m, 3H), 5.97 (dd, 1H, J=15.7, 1.4), 6.38 (d, 1H, J=7.8), 6.42–6.47 (m, 2H), 6.86 (dd, 1H, J=15.7, 5.1), 7.08–7.13 (m, 1H); Anal. (C$_{25}$H$_{36}$N$_2$O$_7$) C, H, N.

Preparation of Intermediate Ethyl-3-{Cbz-L-Leu-L-Phe-L-((N-2,4-Dimethoxybenzyl)-(R)-Pyrrol-Ala)}-E-Propenoate A solution of HCl in 1,4-dioxane (4.0 M, 6 mL) was added to a solution of ethyl-3-{Boc-L-((N-2,4-dimethoxybenzyl)-(R)-Pyrrol-Ala)}-E-propenoate (0.233 g, 0.489 mmol, 1 equiv.) in 1,4-dioxane (6 mL). After stirring 1.5 h, the volatiles were evaporated to give the crude amine salt, which was used without purification.

This amine salt was dissolved in DMF (4 mL) and cooled to 0° C. Cbz-L-Leu-L-Phe-OH (0.202 g, 0.490 mmol, 1 equiv.), DIEA (0.255 mL, 1.46 mmol, 3 equiv.) and HATU (0.186 g, 0.489 mmol, 1 equiv.) were added sequentially. After stirring 1.5 h, the reaction mixture was diluted with MTBE (100 mL), washed with 5% KHSO$_4$, saturated NaHCO$_3$ and brine (10 mL), dried over MgSO$_4$, and evaporated. Purification of the residue by flash column chromatography (gradient elution, 60→75% EtOAc in hexanes) provided ethyl-3-{Cbz-L-Leu-L-Phe-L-((N-2,4-dimethoxybenzyl)-(R)-Pyrrol-Ala)}-E-propenoate (0.208 g, 55%) as a white solid (after evaporation from Et$_2$O): mp=174–176° C.; IR (cm$^{-1}$) 3287, 1713, 1649; $^1$H NMR (CDCl$_3$) δ 0.84–0.91 (m, 6H), 1.29 (t, 3H, J=7.2), 1.42–1.66 (m, 4H), 1.67–1.77 (m, 1H), 1.84–1.95 (m, 1H), 2.20–2.12 (m, 1H), 2.33–2.45 (m, 1H), 3.04–3.23 (m, 4H), 3.78 (s, 3H), 3.79 (s, 3H), 4.15–4.29 (m, 1H), 4.17 (q, 2H, J=7.2), 4.31 (d, 1H, J=14.5), 4.40 (d, 1H, J=14.5), 4.67–4.84 (m, 2H), 5.05 (d, 1H, J=12.1), 5.11 (d, 1H, J=12.1), 5.35 (d, 1H, J=8.1), 5.76 (dd, 1H, J=15.6, 1.6), 6.42–6.46 (m, 2H), 6.74–6.81 (m, 1H), 6.75 (dd, 1H, J=15.6, 5.0), 7.06–7.10 (m, 1H), 7.15–7.24 (m, 5H), 7.29–7.36 (m, 5H), 8.79 (d, 1H, J=5.9); Anal. (C$_{43}$H$_{54}$N$_4$O$_9$) C, H, N.

Preparation of Product Ethyl-3-{Cbz-L-Leu-L-Phe-L-((R)-Pyrrol-Ala)}-E-Propenoate Ethyl-3-{Cbz-L-Leu-L-Phe-L-((N-2,4-dimethoxybenzyl)-(R)-Pyrrol-Ala)}-E-propenoate was converted to the product ethyl-3-{Cbz-L-Leu-L-Phe-L-((R)-Pyrrol-Ala)}-E-propenoate in a manner analogous to the conversion of ethyl-3-{Cbz-L-Leu-L-Phe-L-((N-2,4-dimethoxybenzyl)-(S)-Pyrrol-Ala)}-E-propenoate to product ethyl-3-{Cbz-L-Leu-L-Phe-L-((S)-Pyrrol-Ala)}-E-propenoate described in Example 34: IR (cm$^{-1}$) 3290, 1702, 1642; $^1$H NMR (CDCl$_3$) δ 0.85–0.92 (m, 6H), 1.30 (t, 3H, J=7.2), 1.35–1.49 (m, 1H), 1.52–1.71 (m, 3H), 1.73–1.94 (m, 2H), 2.15–2.26 (m, 1H), 2.32–2.43 (m, 1H), 3.02–3.18 (m, 2H), 3.19–3.29 (m, 2H), 4.15–4.27 (m, 1H), 4.18 (q, 2H, J=7.2), 4.65–4.74 (m, 1H), 4.76–4.85 (m, 1H), 5.07 (d, 1H, J=12.3), 5.12 (d, 1H, J=12.3), 5.18–5.25 (m, 1H), 5.76–5.84 (m, 2H), 6.64–6.78 (m, 2H), 7.15–7.40 (m, 10H), 7.91–7.98 (m, 1H); Anal. ($C_{34}H_{44}N_4O_7$) C, H, N.

Example 37

Preparation of Compound (A-28): Ethyl-3-{Cbz-L-Leu-L-Phe-L-1-(2-imidazolidone)Ala}-E-Propenoate

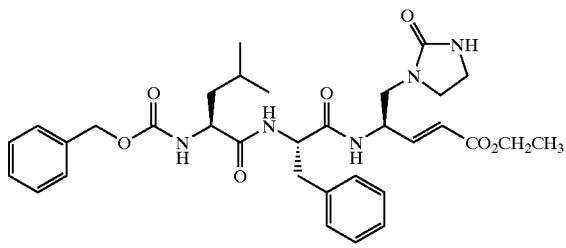

(A-28)

Preparation of Intermediate Ethyl-3-{Cbz-L-Leu-L-Phe-L-Boc-aminoAla}-E-Propenoate (Carbethoxymethlene)triphenylphosphorane (1.20 g, 3.28 mmol, 1.2 equiv.) was added to a solution of Cbz-L-Leu-L-Phe-L-N-Boc-aminoalaninal (prepared as described in Webber et al., *J. Med. Chem.* 1998, vol. 41, 2786) (1.60 g, 2.73 mmol, 1 equiv.) in THF (55 mL), and the reaction was stirred at room temperature overnight. The volatiles were then removed in vacuo, and the residue was purified by flash column chromatography eluting (gradient elution, 0→1.5% $CH_3OH$ in $CH_2Cl_2$) to give ethyl-3-{Cbz-L-Leu-L-Phe-L-N-Boc-aminoAla}-E-propenoate (0.968 g, contaminated with triphenylphosphine oxide). This material was used without further purification.

Preparation of Intermediate Ethyl-3-{Cbz-L-Leu-L-Phe-L-(2-Boc-2-aminoethyl)aminoAla}-E-Propenoate A solution of HCl in 1,4-dioxane (4.0 M, 10 mL) was added to a solution of ethyl-3-{Cbz-L-Leu-L-Phe-L-Boc-aminoAla}-E-propenoate (0.95 g, 1.46 mmol, 1 equiv.) in the same solvent (20 mL) at 23° C. The reaction mixture was stirred at that temperature for 1.5 h, and then additional HCl in 1,4-dioxane (4.0 M, 10 mL) was added. After stirring overnight, the volatiles were removed in vacuo and the residue was triturated with $Et_2O$ (20 mL). The resulting solids were filtered and were washed with $Et_2O$ (3×10 mL) to give the crude amine salt (0.63 g 73%, 1.05 mmol) as a white solid.

This material was dissolved in $CH_3OH$ (10 mL), and then N-Boc-2-aminoethanal (prepared as described in Bischofberger et al., *J. Org. Chem.* 1988, vol. 53, 3457) (0.19 g, 1.16 mmol, 1.1 equiv.) and $NaBH_3CN$ (0.069 g, 1.05 mmol, 1.0 equiv.) were added sequentially. The reaction mixture was stirred at 23° C. overnight, and then the volatiles were removed under reduced pressure. The residue was dissolved in EtOAc (25 mL) and the organic layer was washed with water (25 mL) and brine (25 mL), and then dried over $MgSO_4$ and concentrated. The residue was purified by flash column chromatography (gradient elution, 0→3% $CH_3OH$ in $CH_2Cl_2$) to provide ethyl-3-{Cbz-L-Leu-L-Phe-L-(2-Boc-2-aminoethyl)aminoAla}-E-propenoate (0.32 g, 44%) as a white amorphous solid: $R_f$=0.20 (5% $CH_3OH$ in $CHCl_3$); IR ($cm^{-1}$) 1712, 1649, 1537, 1252, 1175; $^1H$ NMR (DMSO-$d_6$) δ 0.79 (d, 3H, J=6.6), 0.82 (d, 3H, J=6.6), 1.21 (t, 3H, J=7.0), 1.26–1.37 (m, 13H), 1.46–1.54 (m, 1H), 2.56–2.60 (m, 2H), 2.82–2.97 (m, 4H), 3.98–4.04 (m, 1H), 4.10 (q, 2H, J=7.0), 4.42–4.49 (m, 2H), 4.98 (d, 1H, J=12.5), 5.04 (d, 1H, J=12.9), 5.59 (d, 1H, J=15.8), 6.73–6.75 (m, 1H), 6.77 (dd, 1H, J=15.8, 4.8), 7.20–7.34 (m, 10H), 7.41 (d, 1H, J=8.1), 7.97 (d, 1H, J=7.0), 8.07 (d, 1H, J=7.0); Anal. ($C_{37}H_{53}N_5O_8$·0.5$OH_2O$) C, H, N.

Preparation of Product Ethyl-3-{Cbz-L-Leu-L-Phe-L-1-(2-imidazolidone)Ala}-E-Propenoate TFA (0.8 mL) was added to a solution of ethyl-3-{Cbz-L-Leu-L-Phe-L-(2-Boc-2-aminoethyl)aminoAla}-E-propenoate (0.29 g, 0.42 mmol, 1 equiv.) in $CH_2Cl_2$ (8 mL), and the reaction mixture was stirred at 23° C. for 2 h. The volatiles were removed in vacuo, and the residue was dissolved in EtOAc (25 mL) and washed with saturated $NaHCO_3$ solution (25 mL), water (25 mL), and brine (25 mL). The organic layer was dried over $MgSO_4$ and was concentrated to give the crude diamine (0.23 g, 92%, 0.39 mmol) as a tan amorphous solid.

This material was dissolved in THF (4 mL), carbonyldiimidazole (0.06 g, 0.36 mmol, 0.92 equiv.) was added, and the reaction mixture was stirred at 23° C. for 3.5 h. The solvent was removed in vacuo, and the residue was purified by flash column chromatography (gradient elution, 0→2% $CH_3OH$ in $CH_2Cl_2$) to give ethyl-3-{Cbz-L-Leu-L-Phe-L-1-(2-imidazolidone)Ala}-E-propenoate (0.12 g, 54%) as a white amorphous solid: mp=161–164° C.; $R_f$=0.21 (5% $CH_3OH$ in $CHCl_3$); IR ($cm^{-1}$) 1701, 1647, 1535, 1277; $^1H$ NMR (DMSO-$d_6$) δ 0.79 (d, 3H, J=6.6), 0.82 (d, 3H, J=6.6), 1.21 (t, 3H, J=7.0), 1.27–1.35 (m, 2H), 1.48–1.52 (m, 1H), 2.79–2.86 (m, 1H), 2.92–3.05 (m, 3H), 3.14–3.19 (m, 2H), 3.25–3.30 (m, 2H), 3.98–4.03 (m, 1H), 4.10 (q, 2H, J=7.0), 4.47–4.49 (m, 1H), 4.59–4.63 (m, 1H), 4.97–5.02 (m, 2H), 5.72 (d, 1H, J=15.8), 6.37 (s, 1H), 6.71 (dd, 1H, J=15.8, 5.5), 7.15–7.39 (m, 10H), 7.42 (d, 1H, J=8.1), 8.00 (d, 1H, J=8.1), 8.18 (d, 1H, J=8.1); Anal. ($C_{33}H_{43}N_5O_7$) C, H, N.

Example 38

Synthesis of Intermediates Q1, Q2, and Q3

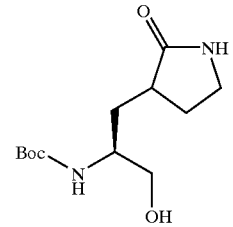

Q1

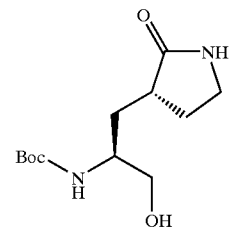

Q2

Q3

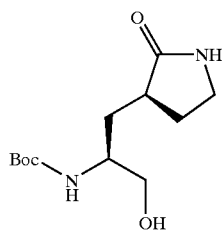

Preparation of Intermediate 1-Acetyl-3-(triphenylphosphanylidine)-pyrrolidin-2-one 2,4-Dibromobutyride (prepared according to Ikuta et al., J. Med. Chem, 1987, vol. 30, 1995) (46.1 g, 188.2 mmol) in THF (1 L) was cooled to 0° C. and treated with a solution of lithium bis(trimethylsilylamide) (40.9 g, 244.6 mmol) in THF (200 mL). The solution was held at 0° C. for 2.5 h, and then poured into brine (800 mL), extracted with ethyl acetate (2 L), and dried ($MgSO_4$). Evaporation yielded 25.5 g of 3-bromo-pyrrolidin-2-one as a brown oil. This material was treated with $Ac_2O$ (76 mL) and refluxed 5 hours. Evaporation followed by purification (silica gel filtration, EtOAc elutant) yielded 28 g of 1-acetyl-3-bromo-pyrrolidin-2-one as a dark oil. THF (272 mL) and triphenylphosphine (42.8 g, 163.3 mmol) were added and the resulting solution was refluxed for 8 hours. Upon cooling to 23° C., a precipitate of 1-acetyl-3-(triphenylphosphanyl)-pyrrolidin-2-one bromide formed and was collected by filtration (27.1 g). Concentration of the mother liquor, followed by cooling to 0° C., yielded an additional 6.6 g. The combined material in $CH_2Cl_2$ (1 L) was washed with 1N NaOH (100 mL) and then brine (2×100 mL). Evaporation of the organic layer yielded 26.9 g (37% overall) of 1-acetyl-3-(triphenylphosphanylidine)-pyrrolidin-2-one as a tan oil. $^1H$ NMR ($CDCl_3$) δ 7.76–7.32 (15H, m), 3.90–3.85 (2H, m), 2.50 (3H, s), 2.56–2.30 (2H, m).

Preparation of Intermediate 2-t-Butoxycarbonyl-3-(t-butyldimethylsilanoxy)-propionic acid methyl ester Boc-D-serine methyl ester (20.0 g, 91.2 mmol) in DMF (300 mL) was treated with imidazole (18.6 g, 273.7 mmol) and then TBSCl (13.0 g, 86.7 mmol). The solution was held at room temperature (rt) for 8 h, and then washed with saturated aqueous ammonium chloride (300 mL), and extracted with ethyl acetate (800 mL). The organic layer was washed with brine (300 mL) and then dried ($MgSO_4$), to yield 30.2 g (100%) of 2-t-butoxycarbonyl-3-(t-butyldimethylsilanoxy)-propionic acid methyl ester as a colorless oil. $^1H$ NMR ($CDCl_3$) δ 5.32 (1H, d, J=8.3), 4.33 (1H, dt, J=8.8, 2.7), 4.02 (1H, dd, J=10.1, 2.6), 3.80 (1H, dd, J=9.8, 3.1), 3.72 (3H, s), 1.43 (9H, s), 0.85 (9H, s), 0.0 (6H, s).

Preparation of Intermediate {1-(1-Acetyl-2-oxo-pyrrolidin-3-ylidenemethyl)-2-(t-butyldimethylsilanyloxy)-ethyl}-carbamic acid t-butyl ester 2-t-Butoxycarbonyl-3-(t-butyldimethylsilanoxy)-propionic acid methyl ester (12.7 g, 38.0 mmol) in toluene (190 mL) was cooled to −78° C. and treated with a solution of diisobutylaluminum hydride (15.6 mL, 87.4 mmol) in toluene (175 mL). The internal temperature was kept below −70° C. The solution was held at −78° C. for an additional 90 min., and then methanol (7.7 mL, 190 mmol) was added. 1-Acetyl-3-(triphenylphosphanylidine)-pyrrolidin-2-one (11.1 g, 28.6 mmol) in $CH_2Cl_2$ (50 mL) was added at −78° C., and the resulting solution was allowed to warm to room temperature and held for 30 minutes. A solution of sodium potassium tartrate (150 g) in water (600 mL) was added, and stirred vigorously for 30 minutes. The mixture was extracted with ethyl acetate (4×250 mL), dried ($MgSO_4$), and evaporated. Purification by silica gel chromatography yielded 7.04 g (60%) of {1-(1-acetyl-2-oxo-pyrrolidin-3-ylidenemethyl)-2-(t-butyldimethylsilanyloxy)-ethyl}-carbamic acid t-butyl ester as a colorless oil. $^1H$ NMR ($CDCl_3$) δ 6.59 (1H, dt, J=8.7, 2.9), 4.98 (1H, d, J=6.8), 4.37–4.25 (1H, m), 3.77 (2H, t, J=7.3), 3.70–3.58 (2H, m), 2.90–2.80 (1H, m), 2.75–2.60 (1H, m), 5.53 (3H, s), 1.41 (9H, s), 0.87 (9H, s), 0.04 (6H, s).

Preparation of Intermediate {2-Hydroxy-1-(2-oxo-pyrrolidin-3-ylidenemethyl)-ethyl}-carbamic acid t-butyl ester {1-(1-Acetyl-2-oxo-pyrrolidin-3-ylidenemethyl)-2-(t-butyldimethylsilanyloxy)-ethyl}-carbamic acid t-butyl ester (9.18 g, 22.2 mmol) in TBF (150 mL) was treated with TBAF (22.2 mL of a 1M solution in THF, 22.2 mmol) at 0° C., and held for 1 hour. A solution of saturated aqueous ammonium chloride was added and stirred for 10 min., and then the solution was extracted with ethyl acetate (2×200 mL). The organic layer was dried ($MgSO_4$) and then evaporated. Purification by silica gel chromatography yielded 4.82 g (73%) of a colorless oil. This material was taken up in methanol (160 mL), treated with potassium carbonate (223 mg, 1.62 mmol), and held for 1 h at rt. The mixture was then treated with solid citric acid (311 mg, 1.62 mmol), and ethyl acetate (800 mL) was added. The solution was filtered through silica gel. Evaporation yielded 4.30 g (73% overall) of {2-hydroxy-1-(2-oxo-pyrrolidin-3-ylidenemethyl)-ethyl}-carbamic acid t-butyl ester as a colorless oil. $^1H$ NMR ($CDCl_3$) δ 7.03 (1H, br s), 6.35 (1H, dt, J=8.6, 2.6), 5.37 (1H, d, J=6.5), 4.40–4.20 (1H, m), 3.66 (br s, 3H), 3.4 (2H, t, J=6.7), 3.10–2.80 (1H, m), 2.80–2.70 (1H, m), 1.41 (9H, s).

Preparation of Intermediate {2-Hydroxy-1-(2-oxy-pyrrolidin-3-ylmethyl)-ethyl}-carbamic acid t-butyl ester (mixture of diastereomers) (Q1)

{2-Hydroxy-1-(2-oxo-pyrrolidin-3-ylidenemethyl)-ethyl}-carbamic acid t-butyl ester (4.30 g, 16.8 mmol) in ethyl acetate (168 mL) was treated with 5% palladium on carbon (1.78 g), and hydrogenated at ambient pressure for 1 h. The mixture was filtered and then evaporated to yield 3.92 g (91%) of {2-hydroxy-1-(2-oxy-pyrrolidin-3-ylmethyl)-ethyl}-carbamic acid t-butyl ester as a colorless oil (1.5:1 mixture of diastereomers): $^1H$ NMR ($CDCl_3$) δ 6.99 (1H, s), 5.49 (1H, d, J=8.4), 3.70–3.50 (3H, m), 3.38–3.20 (2H, m), 2.60–2.20 (2H, m), 2.00–1.70 (2H, m), 1.65–1.45 (1H, m), 1.37 (9H, s).

Preparation of Intermediate {2-Hydroxy-1-(R-2-oxy-pyrrolidin-3-ylmethyl)-ethyl}-carbamic acid t-butyl ester (Q2)

{2-Hydroxy-1-(2-oxo-pyrrolidin-3-ylidenemethyl)-ethyl}-carbamic acid t-butyl ester (98 mg, 0.39 mmol) in methanol (5 mL) was treated with (R)-BINAP-RuCl (19 mg, 0.02 mmol), and then put under a hydrogen atmosphere (1200 psi) at 50° C. for 48 h. The solution was evaporated and then filtered through silica gel (10% MeOH-EtOAc elutant). Evaporation yielded 75 mg (75%) of {2-hydroxy-1-(R-2-oxy-pyrrolidin-3-ylmethyl)-ethyl}-carbamic acid t-butyl ester as a colorless oil (9:1 mixture of diastereomers): $^1$H NMR (CDCl$_3$) δ 6.32 (1H, br s), 5.40(1H, d, J=7.5), 3.82 (1H, br s), 3.71–3.63 (2H, m), 3.34–3.31 (2H, m), 2.45–2.30 (2H, m), 2.09–1.86 (2H, m), 1.70–1.63 (1H, m), 1.42 (9H, s).

Preparation of Intermediate {2-Hydroxy-1-(S-2-oxy-pyrrolidin-3-ylmethyl)-ethyl}-carbamic acid t-butyl ester (Q3)

{2-Hydroxy-1-(2-oxo-pyrrolidin-3-ylidenemethyl)-ethyl}-carbamic acid t-butyl ester (0.10 g, 0.39 mmol) in methanol (5 mL) was treated with (S)-BINAP-RuCl (19 mg, 0.02 mmol), and then put under a hydrogen atmosphere (1200 psi) at 50° C. for 48 h. The solution was evaporated and then filtered through silica gel (10% MeOH-EtOAc elutant). Evaporation yielded 74 mg (74%) of {2-hydroxy-1-(S-2-oxy-pyrrolidin-3-ylmethyl)-ethyl}-carbamic acid t-butyl ester as a colorless oil (9:1 mixture of diastereomers): $^1$H NMR (CDCl$_3$) δ 6.66 (1H, br s), 5.51 (1H, d, J=8.2), 3.72–3.57 (3H, m), 3.34–3.31 (2H, m), 2.52–2.33 (2H, m), 2.20–1.86 (1H, m), 1.86–1.70 (1H, m), 1.62–1.50 (1H, m), 1.40 (9H, s).

Results of biochemical and biological tests conducted using various compounds of the invention are described below.

BIOCHEMICAL AND BIOLOGICAL EVALUATION

Inhibition of Rhinovirus 3C Protease

Stock solutions (50 mM, in DMSO) of various compounds were prepared; dilutions were in the same solvent. Recombinant rhinovirus 3C proteases (see Birch et al., "Purification of recombinant human rhinovirus 14 3C protease expressed in *Escherichia coli*," Protein Expr. Pur. 1995, 6(5), 609–618) from serotypes 14, 16, and 2 were prepared by the following standard chromatographic procedures: (1) ion exchange using Q Sepharose Fast Flow from Pharmacia; (2) affinity chromatography using Affi-Gel Blue from Biorad; and (3) sizing using Sephadex G-100 from Pharmacia. Each assay sample contained 2% DMSO, 50 mM tris pH 7.6, 1 mM EDTA, a test compound at the indicated concentration, approximately 1 μM substrate, and 50–100 nM protease. The $k_{obs}$/I values were obtained from reactions initiated by addition of enzyme rather than substrate. RVP activity was measured in the fluorescence resonance energy transfer assay. The substrate was (N-terminal) DABCYL-(Gly-Arg-Ala-Val-Phe-Gln-Gly-Pro-Val-Gly)-EDANS (SEQ ID NO. 1). In the uncleaved peptide, the EDANS fluorescence was quenched by the proximal DABCYL moiety. When the peptide was cleaved, the quenching was relieved, and activity was measured as an increase in fluorescence signal. Data were analyzed using standard non-linear fitting programs (Enzfit), and are shown in Tables 1 and 2 below. In Table 1, all data are for rhinovirus 3C protease from HRV serotype-14 (produced from the infectious cDNA clone constructed by Dr. Robert Rueckert, Institute for Molecular Virology, University of Wisconsin, Madison, Wis.). Table 2 shows protease-inhibiting activity of compounds against proteases from several rhinovirus of serotype other than RVP serotype-14. The data in the column designated $k_{obs}$/[I] were measured from progress curves in enzyme start experiments.

Antirhinoviral H1-HeLa Cell Culture Assay

In this cell protection assay, the ability of compounds to protect cells against HRV infection was measured by the XTT dye reduction method, which is described in Weislow et al., *J. Natl. Cancer Inst.* 1989, vol. 81, 577–586.

H1-HeLa cells were infected with HRV-14 at a multiplicity of infection (m.o.i.) of 0.13 (virus particles/cell) or mock-infected with medium only. Infected or mock-infected cells were resuspended at 8×10$^5$ cells per mL, and incubated with appropriate concentrations of the compounds to be tested. Two days later, XTT/PMS was added to test plates and the amount of formazan produced was quantified spectrophotometrically at 450/650 nm. The EC$_{50}$ value was calculated as the concentration of compound that increased the percentage of formazan production in compound-treated, virus-infected cells to 50% of that produced by compound-free, mock-infected cells. The 50% cytotoxic dose (CC$_{50}$) was calculated as the concentration of compound that decreased the percentage of formazan produced in compound-treated, mock-infected cells to 50% of that produced by compound-free, mock-infected cells. The therapeutic index (TI) was calculated by dividing the CC$_{50}$ value by the EC$_{50}$ value.

All strains of human rhinovirus (HRV) for use in this assay were purchased from American Type Culture Collection (ATCC), except for HRV serotype-14 (produced from the infectious cDNA clone constructed by Dr. Robert Rueckert, Institute for Molecular Virology, University of Wisconsin, Madison, Wis.). HRV stocks were propagated and viral assays were performed in H1-HeLa cells (ATCC). Cells were grown in minimal essential medium with 10% fetal bovine serum, available from Life Technologies (Gaithersburg, Md.).

The compounds were tested against control compounds WIN 51711, WIN 52084, and WIN 54954 (obtained from Sterling-Winthrop Pharmaceuticals), Pirodavir (obtained from Janssen Pharmaceuticals), and Pleconaril (prepared according to the method described in Diana et al., *J. Med. Chem* 1995, vol. 38, 1355). Antiviral data obtained for the test compounds are shown in Tables 1 and 3, where all data are for HRV serotype-14 unless otherwise noted in parentheses. The designation "ND" indicates that a value was not determined for that compound.

TABLE 1

Activity vs. HRV Serotype-14

| Compound | Protease Inhibition $k_{obs}$/[I] (M$^{-1}$sec$^{-1}$) | Cell Protection EC$_{50}$ (μM) |
|---|---|---|
| Example 31 (Comparison Compound #2) | 25,000 | 0.61 |
| Example 35 (A-26) | 239,000 | 0.03 |
| Example 33 (A-24) | 257,000 | 0.10 |
| Example 36 (A-27) | 18,000 | 1.6 |
| Example 32 (Comparison Compound #3) | 62,500 | 0.38 |
| Example 34 (A-25) | 500,000 | 0.03 |
| Example 5 (A-4) | 270,000 | 0.10 |
| Example 8 (A-7) | 980,000 | 0.004 |
| Example 7 (A-6) | 248,000 | 0.42 |
| Example 9 (A-8) | 900,000 | ND |
| Example 6 (A-5) | 1,500,000 | 0.005 |
| Example 12 (C-1) | 68,400 | 0.10 |
| Example 18 (C-2) | 270,000 | 0.002 |
| Example 10 (B-1) | 240,000 | 0.10 |
| Example 20 (B-4) | 500,000 | <0.03 |
| Example 17 (B-2) | 1,090,000 | 0.005 |
| Example 1 (Comparison Compound #1) | 573 | >320 |
| Example 2 (A-1) | 260,000 | 0.25 |
| Example 3 (A-2) | 46,900 | 1.6 |
| Example 4 (A-3) | 310,000 | 0.05 |
| Example 11 (A-10) | 108,000 | 0.14 |
| Example 13 (A-11) | 108,000 | 0.03 |

TABLE 1-continued

Activity vs. HRV Serotype-14

| Compound | Protease Inhibition $k_{obs}/[I]$ ($M^{-1}sec^{-1}$) | Cell Protection $EC_{50}$ ($\mu M$) |
|---|---|---|
| Example 14 (A-9) | 66,000 | 1.8 |
| Example 15 (A-12) | 59,300 | 0.40 |
| Example 16 (A-13) | 95,800 | 0.20 |
| Example 19 (B-3) | 465,000 | 0.18 |
| Example 21 (A-14) | 54,500 | 0.48 |
| Example 22 (A-15) | 237,100 | 0.22 |
| Example 23 (A-16) | 172,800 | 0.45 |
| Example 24 (A-17) | 167,000 | 0.06 |
| Example 25 (A-18) | 292,000 | 1.5 |
| Example 26 (A-19) | 27,750 | 25.1 |
| Example 27 (A-20) | 1,020 | 12.6 |
| Example 28 (A-21) | 17,800 | 2.5 |
| Example 29 (A-22) | 2,400 | nd |
| Example 30 (A-23) | 26,000 | nd |

TABLE 2

Activity vs. Other HRV Serotypes

| Compound | Rhinovirus Serotype | $k_{obs/I}$ ($M^{-1}sec^{-1}$) |
|---|---|---|
| Comparison Compound #2 | (16) | 6,500 |
| " | (89) | 3,400 |
| " | (2) | 2,000 |
| Comparison Compound #3 | (2) | 8,000 |
| " | (16) | 16,900 |
| (A-24) | (2) | 31,000 |

TABLE 3

Anti-Rhinovirus Activity

| # | HRV | $EC_{50}$ ($\mu M$) | $CC_{50}$ ($\mu M$) | TI |
|---|---|---|---|---|
| Comparison Compound #1 | | >320 | >320 | — |
| (A-1) | | 0.25 | >100 | >400 |
| " | (2) | 0.41 | " | >243 |
| " | (1A) | 1.0 | " | >100 |
| " | (89) | 0.22 | " | >450 |
| (A-2) | | 1.6 | >100 | >63 |
| (A-3) | | 0.05 | >10 | >200 |
| (A-4) | | 0.10 | >100 | >1000 |
| (A-5) | | 0.005 | >10 | >2000 |
| " | (2) | 0.01 | " | >1000 |
| " | (16) | 0.02 | " | >500 |
| " | (39) | 0.02 | " | >500 |
| " | (89) | 0.02 | " | >500 |
| " | (10) | 0.05 | " | >200 |
| " | (1A) | 0.03 | " | >333 |
| " | (3) | 0.05 | " | >200 |
| " | (9) | 0.04 | " | >250 |
| " | (12) | 0.06 | " | >166 |
| " | (13) | 0.02 | " | >500 |
| " | (17) | 0.02 | " | >500 |
| " | (25) | 0.18 | " | >55 |
| " | (30) | 0.06 | " | >166 |
| " | (38) | 0.13 | " | >76 |
| " | (87) | 0.21 | " | >47 |
| (A-6) | | 0.42 | >100 | >237 |
| (A-7) | | 0.004 | >10 | >2500 |
| " | (2) | 0.02 | " | >500 |
| " | (16) | 0.04 | " | >250 |
| " | (39) | 0.02 | " | >500 |
| " | (89) | 0.02 | " | >500 |
| " | (10) | 0.06 | " | >166 |
| " | (1A) | 0.03 | " | >333 |

TABLE 3-continued

Anti-Rhinovirus Activity

| # | HRV | $EC_{50}$ ($\mu M$) | $CC_{50}$ ($\mu M$) | TI |
|---|---|---|---|---|
| " | (3) | 0.02 | " | >500 |
| " | (9) | 0.04 | " | >250 |
| " | (12) | 0.07 | " | >143 |
| " | (13) | 0.03 | " | >333 |
| " | (17) | 0.02 | " | >500 |
| " | (25) | 0.20 | " | >50 |
| " | (30) | 0.09 | " | >111 |
| " | (38) | 0.17 | " | >58 |
| " | (87) | 0.59 | " | >16 |
| (A-8) | | ND | ND | ND |
| (B-1) | | 0.10 | >100 | >1000 |
| " | (1A) | 0.30 | " | >333 |
| " | (10) | 0.40 | " | >250 |
| (A-10) | | 0.14 | >100 | >714 |
| (C-1) | | 0.10 | >10 | >100 |
| (A-11) | | 0.03 | 50 | 1667 |
| (A-9) | | 1.8 | >100 | >55 |
| (A-12) | | 0.40 | >100 | >250 |
| (A-13) | | 0.20 | >10 | >50 |
| (B-2) | | 0.005 | >100 | >20000 |
| " | (2) | 0.02 | " | >5000 |
| " | (16) | 0.01 | " | >10000 |
| " | (39) | 0.05 | " | >2000 |
| " | (89) | 0.009 | " | >11111 |
| " | (10) | 0.02 | " | >5000 |
| " | (1A) | 0.02 | " | >5000 |
| " | (3) | 0.02 | " | >5000 |
| " | (9) | 0.006 | " | >16666 |
| " | (12) | 0.05 | " | >2000 |
| " | (13) | 0.01 | " | >10000 |
| " | (17) | 0.01 | " | >10000 |
| " | (25) | 0.03 | " | >3333 |
| " | (30) | 0.04 | " | >2500 |
| " | (38) | 0.07 | " | >1428 |
| " | (87) | 0.06 | " | >1666 |
| (C-2) | | 0.002 | >10 | >5000 |
| " | (2) | 0.004 | " | >2500 |
| " | (16) | 0.01 | " | >1000 |
| " | (39) | 0.01 | " | >1000 |
| " | (89) | 0.004 | " | >2500 |
| " | (10) | 0.02 | " | >500 |
| " | (1A) | 0.01 | " | >1000 |
| " | (3) | 0.02 | " | >500 |
| " | (9) | 0.01 | " | >1000 |
| " | (12) | 0.04 | " | >250 |
| " | (13) | 0.007 | " | >1428 |
| " | (17) | 0.007 | " | >1428 |
| " | (25) | 0.07 | " | >142 |
| " | (30) | 0.03 | " | >333 |
| " | (38) | 0.05 | " | >200 |
| " | (87) | 0.02 | " | >500 |
| (B-3) | | 0.18 | >100 | >543 |
| (B-4) | | <0.03 | >100 | >3333 |
| (A-14) | | 0.48 | >100 | >208 |
| (A-15) | | 0.22 | >100 | >454 |
| " | (1A) | 7.1 | " | >14 |
| " | (10) | 2.7 | " | >37 |
| (A-16) | | 0.45 | >100 | >222 |
| " | (1A) | 4.8 | " | >21 |
| " | (10) | 4.5 | " | >22 |
| (A-17) | | 0.06 | >100 | >1786 |
| " | (1A) | 1.8 | " | >56 |
| " | (10) | 3.3 | " | >30 |
| (A-18) | | 1.5 | >100 | >67 |
| (A-19) | | 25.1 | >100 | >4 |
| (A-20) | | 12.6 | >100 | >8 |
| (A-21) | | 2.5 | >100 | >40 |
| (A-22) | | ND | ND | ND |
| (A-23) | | ND | ND | ND |
| Comparison Compound #2 | | 0.61 | >320 | >524 |
| Comparison Compound #2 | (16) | 2.3 | >320 | >139 |
| Comparison Compound #2 | (89) | 6.3 | >320 | >50 |

TABLE 3-continued

Anti-Rhinovirus Activity

| # | HRV | EC$_{50}$ ($\mu$M) | CC$_{50}$ ($\mu$M) | TI |
|---|---|---|---|---|
| Comparison Compound #2 | (10) | 0.60 | >320 | >533 |
| Comparison Compound #3 | | 0.38 | >320 | >842 |
| (A-24) | | 0.10 | >100 | >1000 |
| (A-25) | | 0.030 | >100 | >3333 |
| (A-26) | | 0.030 | >100 | >3333 |
| (A-27) | | 1.6 | >100 | >62 |
| WIN 51711 | | 0.78 | >60 | >77 |
| WIN 52084 | | 0.07 | >10 | >143 |
| WIN 54954 | | 2.13 | >63 | >30 |
| Pirodavir | | 0.03 | >10 | >300 |
| Pleconaril | | 0.11 | >10 | >1000 |

Anticoxsackieviral Cell Culture Assay

Coxsackievirus types A-21 (CAV-21) and B3 (CVB-3) were purchased from American Type Culture Collection (ATCC, Rockville, Md.). Virus stocks were propagated and antiviral assays were performed in H1-HeLa cells (ATCC). Cells were grown in minimal essential medium with 10% fetal bovine serum (Life Technologies, Gaithersburg, Md.).

The ability of compounds to protect cells against either CAV-21 or CVB-3 infection was measured by the XTT dye reduction method. This method is described in Weislow et al., *J. Natl. Cancer Inst.* 1989, vol. 81, 577–586. H1-HeLa cells were infected with CAV-21 or CVB-3 at a multiplicity of infection (m.o.i.) of 0.025 or 0.075, respectively, or mock-infected with medium only. H1-HeLa cells were plated at $4\times10^4$ cells per well in a 96-well plate and incubated with appropriate concentrations of the test compound. One day (CVB-3) or two days (CAV-21) later, XTT/PMS was added to test plates and the amount of formazan produced was quantified spectrophotometrically at 450/650 nm. The EC$_{50}$ was calculated as the concentration of compound that increased the formazan production in compound-treated, virus-infected cells to 50% of that produced by compound-free, uninfected cells. The 50% cytotoxic dose (CC$_{50}$) was calculated as the concentration of compound that decreased formazan production in compound-treated, uninfected cells to 50% of that produced in compound-free, uninfected cells. The therapeutic index (TI) was calculated by dividing the CC$_{50}$ by the EC$_{50}$.

The compounds were tested against control compounds WIN 54954 (obtained from Sterling-Winthrop Pharmaceuticals), Pirodavir (obtained from Janssen Pharmaceuticals), and Pleconaril (prepared according to Diana et al., *J. Med. Chem.* 1995, 38, 1355). Antiviral data obtained for the test compounds against CAV-21 and CVB-3 are shown in Table 4.

TABLE 4

Anti-Coxsackievirus Activity

| Compound | Strain | EC$_{50}$ ($\mu$M) | CC$_{50}$ ($\mu$M) | TI |
|---|---|---|---|---|
| (A-5) | CAV-21 | 0.23 | >10 | >43 |
| " | CVB-3 | 1.0 | " | >10 |
| (B-2) | CAV-21 | 0.16 | >100 | >625 |
| " | CVB-3 | 0.18 | " | >555 |
| WIN 54954 | CAV-21 | >100 | >100 | |
| " | CVB-3 | >100 | " | |

TABLE 4-continued

Anti-Coxsackievirus Activity

| Compound | Strain | EC$_{50}$ ($\mu$M) | CC$_{50}$ ($\mu$M) | TI |
|---|---|---|---|---|
| Pirodavir | CAV-21 | >100 | >100 | |
| " | CVB-3 | >100 | " | |
| Pleconaril | CAV-21 | 0.09 | >10 | >107 |
| " | CVB-3 | >10 | " | |

Anti-Echoviral and -Enteroviral Cell Culture Assays

Echovirus type 11 (EV 11) and enterovirus type 70 (EV 70) were purchased from ATCC (Rockville, Md.). Virus stocks were propagated and antiviral assays were performed in MRC-5 cells (ATCC). Cells were grown in minimal essential medium with 10% fetal bovine serum (Life Technologies, Gaithersburg, Md.).

The ability of compounds to protect cells against either EV 11 or EV 70 infection was measured by the XTT dye reduction method (Weislow et al., *J. Natl. Cancer Inst.* 1989, vol. 81, 577–586). MRC-5 cells were infected with EV 11 or EV 70 at an m.o.i. of 0.003 or 0.004, respectively, or mock-infected with medium only. Infected or uninfected cells were added at $1\times10^4$ cells per well and incubated with appropriate concentrations of compound. Four days later, XTT/PMS was added to test plates, and the amount of formazan produced was quantified spectrophotometrically at 450/650 nm. The EC$_{50}$ was calculated as the concentration of compound that increased the formazan production in compound-treated, virus-infected cells to 50% of that produced by compound-free, uninfected cells. The 50% cytotoxic dose (CC$_{50}$) was calculated as the concentration of compound that decreased formazan production in compound-treated, uninfected cells to 50% of that produced in compound-free, uninfected cells. The therapeutic index (TI) was calculated by dividing the CC$_{50}$ by the EC$_{50}$.

The compounds were tested against control compounds Pirodavir (obtained from Janssen Pharmaceuticals) and Pleconaril (prepared according to Diana et al., *J. Med. Chem.* 1995, vol. 38, 1355). Antiviral data obtained for the test compounds against strain EV 11 and EV 70 are shown below in Table 5.

TABLE 5

Anti-Echovirus and Anti-Enterovirus Activity

| Compound | Strain | EC$_{50}$ ($\mu$M) | CC$_{50}$ ($\mu$M) | TI |
|---|---|---|---|---|
| (A-5) | EV-11 | 0.08 | >10 | >125 |
| " | EV-70 | 0.04 | " | >250 |
| (B-2) | EV-11 | 0.01 | >100 | >10000 |
| " | EV-70 | 0.003 | " | >33333 |
| Pirodavir | EV-11 | 3.7 | >10 | >3 |
| " | EV-70 | 0.06 | " | >167 |
| Pleconaril | EV-11 | 0.16 | >10 | >62 |
| " | EV-70 | ND | ND | ND |

While the invention has been described in terms of preferred embodiments and specific examples, those skilled in the art will recognize that various changes and modifications can be made without departing from the spirit and scope of the invention. Thus, the invention should be understood as not being limited by the foregoing detailed description, but as being defined by the appended claims and their equivalents.

What is claimed is:

1. A compound of the formula I:

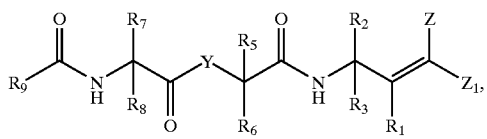

(I)

wherein:

Y is —C($R_y$)($R_y$)— where each $R_y$ is independently H or lower alkyl;

$R_1$ is H, F, an alkyl group, OH, SH, or an O-alkyl group;

$R_2$ and $R_3$ are each independently H;

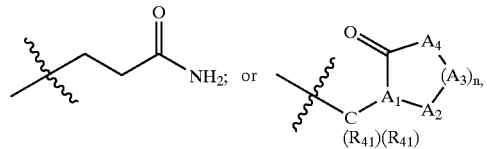

where n is an integer from 0 to 5, $A_1$ is CH or N, $A_2$ and each $A_3$ are independently selected from C($R_{41}$)($R_{41}$), N($R_{41}$), S, S(O), S(O)$_2$, and O, and $A_4$ is NH or NR$_{41}$, where each $R_{41}$ is independently H or lower alkyl, provided that no more than 2 heteroatoms occur consecutively in the ring formed by $A_1$, $A_2$, ($A_3$)$_n$, $A_4$ and C=O; and provided that at least one of $R_2$ and $R_3$ is

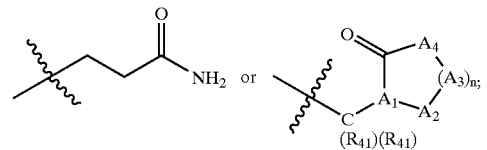

$R_5$ and $R_6$ are each independently H, F, an alkyl group, a cycloalkyl group, a heterocycloalkyl group, an aryl group or a heteroaryl group;

$R_7$ and $R_8$ are each independently H, an alkyl group, a cycloalkyl group, a heterocycloalkyl group, or an aryl group, or a heteroaryl group, —OR$_{17}$, —SR$_{17}$, —NR$_{17}$R$_{18}$, —NR$_{19}$NR$_{17}$R$_{18}$, or —NR$_{17}$OR$_{18}$, where $R_{17}$, $R_{18}$, and $R_{19}$ are each independently H, an alkyl group, a cycloalkyl group, a heterocycloalkyl group, an aryl group, a heteroaryl group, or an acyl group;

$R_9$ is a five-membered heterocycle having from one to three heteroatoms selected from O, N, and S, or $R_9$ is

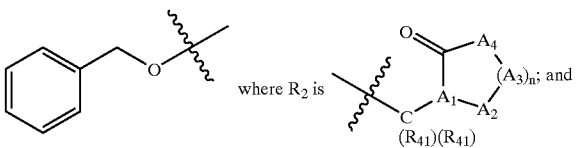

where $R_2$ is

Z and $Z_1$ are each independently H, F, an alkyl group, a cycloalkyl group, a heterocycloalkyl group, an aryl group, a heteroaryl group, —C(O)R$_{21}$, —CO$_2$R$_{21}$, —CN, —C(O)NR$_{21}$R$_{22}$, —C(O)NR$_{21}$OR$_{22}$, —C(S) R$_{21}$, —C(S)NR$_{21}$R$_{22}$, —NO$_2$, —SOR$_{21}$, —SO$_2$R$_{21}$, —SO$_2$NR$_{21}$R$_{22}$, —SO(NR$_{21}$)(OR$_{22}$), —SONR$_{21}$, —SO$_3$R$_{21}$, —PO(OR$_{21}$)$_2$, —PO(R$_{21}$)(R$_{22}$), —PO(NR$_{21}$R$_{22}$)(OR$_{23}$), PO(NR$_{21}$R$_{22}$)(NR$_{23}$R$_{24}$), —C(O)NR$_{21}$NR$_{22}$R$_{23}$, or —C(S)NR$_{21}$NR$_{22}$R$_{23}$, where $R_{21}$, $R_{22}$, $R_{23}$, and $R_{24}$ are each independently H, an alkyl group, a cycloalkyl group, a heterocycloalkyl group, an aryl group, a heteroaryl group, an acyl group, or a thioacyl group, or any two of $R_{21}$, $R_{22}$, $R_{23}$, and $R_{24}$, together with the atom(s) to which they are bonded, form a heterocycloalkyl group, provided that Z and $Z_1$ are not both H;

or $Z_1$ and $R_1$, together with the atoms to which they are bonded, form a cycloalkyl or heterocycloalkyl group;

or Z and $Z_1$, together with the atoms to which they are bonded, form a cycloalkyl or heterocycloalkyl group; or solvate thereof.

2. A compound or solvate according to claim 1, wherein $R_2$ and $R_3$ are each independently H;

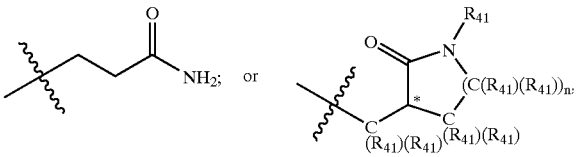

where n is an integer from 0 to 5, each $R_{41}$ is independently H or lower alkyl, and the stereochemistry at the carbon denoted with an asterisk (*) may be R or S; provided that at least one of $R_2$ and $R_3$ is

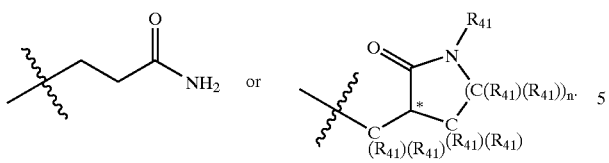

3. A compound or solvate according to claim 1, wherein Y is —N(R$_y$)—, where R$_y$ is H or lower alkyl.

4. A compound or solvate according to claim 3, wherein: Z and Z$_1$ are each independently selected from H, F, lower alkyl, —CO$_2$R$_{21}$, and —C(O)NR$_{21}$R$_{22}$, where R$_{21}$ and R$_{22}$ are each independently H, an alkyl group, a cycloalkyl group, a heterocycloalkyl group, an aryl group, a heteroaryl group, an acyl group, or a thioacyl group, or R$_{21}$ and R$_{22}$, together with the atom(s) to which they are bonded, form a heterocycloalkyl group, provided that Z and Z$_1$ are not both H;

or Z$_1$ and R$_1$, together with the atoms to which they are bonded, form a cycloalkyl or heterocycloalkyl group;

or Z and Z$_1$, together with the atoms to which they are bonded, form a cycloalkyl or heterocycloalkyl group.

5. A compound or solvate according to claim 3, wherein R$_1$ is H, F, or methyl.

6. A compound or solvate according to claim 3, wherein at least one of R$_2$ or R$_3$ is

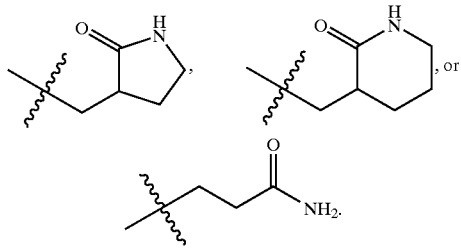

7. A compound or solvate according to claim 6, wherein one of R$_5$ and R$_6$ is H and the other is alkyl or aryl.

8. A compound or solvate according to claim 3, wherein one of R$_5$ and R$_6$ is H and the other is alkyl or aryl.

9. A compound or solvate according to claim 3, wherein one of R$_5$ and R$_6$ is H and the other is unsubstituted or substituted phenylmethyl.

10. A compound or solvate according to claim 3, wherein R$_7$ and R$_8$ are each independently H, an alkyl group, a cycloalkyl group, a heterocycloalkyl group, an aryl group, or a heteroaryl group.

11. A compound or solvate according to claim 3, wherein one of R$_7$ and R$_8$ is H and the other is alkyl or aryl.

12. A compound or solvate according to claim 3, wherein one of R$_7$ and R$_8$ is H and the other is 2-propyl, 2-methyl-2-propyl, 2-methyl-1-propyl, phenylmethyl, or naphthylmethyl.

13. A compound or solvate according to claim 3, wherein R$_9$ is a five-membered heterocycle having at least one nitrogen heteroatom and one oxygen heteroatom.

14. A compound or solvate according to claim 3, wherein R$_9$ is selected from substituted and unsubstituted 1,2-oxazolyl, 1,3-oxazolyl, and 1,2,4-oxadiazolyl.

15. A compound or solvate according to claim 3, wherein R$_9$ is 3-isoxazolyl or 5-isoxazolyl unsubstituted or substituted with one or two substituents selected from methyl and halogens.

16. A method of inhibiting picornavirus replication in a mammal afflicted with meningitis or hepatitis A comprising administering a compound according to claim 1 to a mammal for a time and under conditions effective to inhibit picornavirus replication.

17. A compound according to claim 1 of the formula:

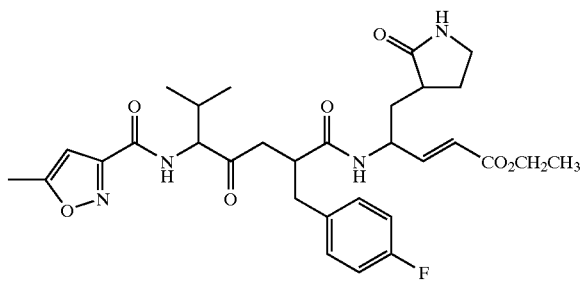

or a solvate thereof.

18. A compound which is a metabolite of a compound according to claim 1, wherein said metabolite is effective to inhibit replication of a picornavirus.

19. A composition comprising an acceptable carrier and a compound according to claim 1 in an amount effective to inhibit replication of a picornavirus.

20. A compound or solvate according to claim 1, wherein Y is —CH$_2$—.

21. A compound or solvate according to claim 20, wherein one of R$_5$ and R$_6$ is H and the other is alkyl or aryl.

22. A compound or solvate according to claim 20, wherein one of R$_5$ and R$_6$ is H and the other is unsubstituted or substituted phenylmethyl.

23. A compound or solvate according to claim 20, wherein R$_7$ and R$_8$ are each independently H, an alkyl group, a cycloalkyl group, a heterocycloalkyl group, an aryl group, or a heteroaryl group.

24. A compound or solvate according to claim 20, wherein one of R$_7$ and R$_8$ is H and the other is alkyl or aryl.

25. A compound or solvate according to claim 20, wherein one of R$_7$ and R$_8$ is H and the other is 2-propyl, 2-methyl-2-propyl, 2-methyl-1-propyl, phenylmethyl, or naphthylmethyl.

26. A compound or solvate according to claim 20, wherein R$_9$ is a five-membered heterocycle having at least one nitrogen heteroatom and one oxygen heteroatom.

27. A compound or solvate according to claim 26, wherein R$_9$ is unsubstituted or substituted 1,2-oxazolyl, 1,3-oxazolyl, or 1,2,4-oxadiazolyl.

28. A compound or solvate according to claim 27, wherein R$_9$ is 3-isoxazolyl or 5-isoxazolyl unsubstituted or substituted with one or two substituents selected from methyl and halogens.

29. A compound or solvate according to claim 20, wherein at least one of R$_2$ and R$_3$ is

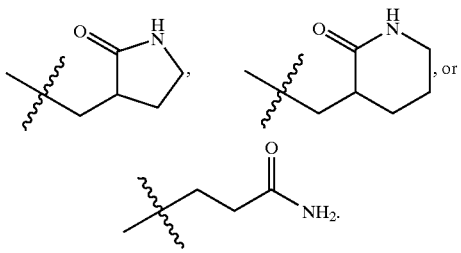

30. A compound or solvate according to claim 29, wherein one of R$_5$ and R$_6$ is H and the other is alkyl or aryl.

31. A compound or solvate according to claim 20, wherein R$_1$ is H, F, or methyl.

32. A compound or solvate according to claim 20, wherein Z and $Z_1$ are each independently selected from H, F, lower alkyl, —$CO_2R_{21}$, and —$C(O)NR_{21}R_{22}$, where $R_{21}$ and $R_{22}$ are each independently H, an alkyl group, a cycloalkyl group, a heterocycloalkyl group, an aryl group, a heteroaryl group, an acyl group, or a thioacyl group, or $R_{21}$ and $R_{22}$, together with the atom(s) to which they are bonded, form a heterocycloalkyl group, provided that Z and $Z_1$ are not both H;

or $Z_1$ and $R_1$, together with the atoms to which they are bonded, form a cycloalkyl or heterocycloalkyl group;

or Z and $Z_1$, together with the atoms to which they are bonded, form a cycloalkyl or heterocycloalkyl group.

33. A compound according to claim 20 of the formula I-B":

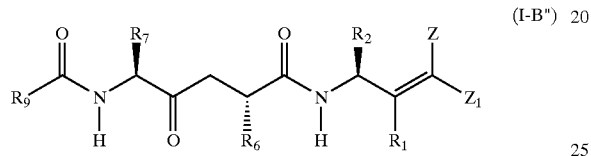
(I-B")

wherein $R_1$, $R_2$, $R_6$, $R_7$, $R_9$, Z, and $Z_1$ are as defined in claim 20, or a solvate thereof.

34. A compound or solvate according to claim 33, wherein $R_1$ is H and:

$R_2$ is $CH_2CH_2C(O)NH_2$, $R_6$ is

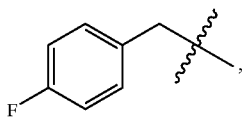, $R_7$ is $CH(CH_3)_2$, Z is H, $Z_1$ is $CO_2CH_2CH_3$, and $R_9$ is

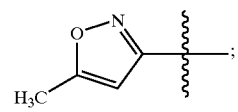;

$R_2$ is

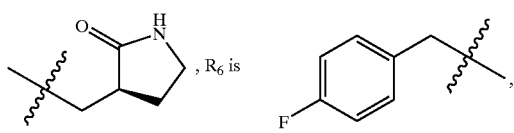

$R_7$ is $CH(CH_3)_2$, Z is H, $Z^1$ is $CO_2CH_2CH_3$, and $R_9$ is

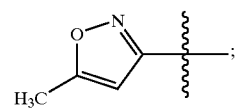;

$R_2$ is 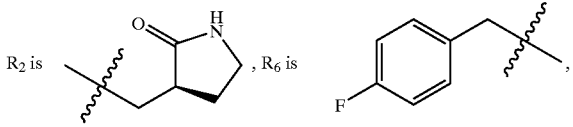, $R_6$ is $R_7$ is $CH(CH_3)_2$, Z and $Z_1$ together are

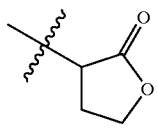

where the carbonyl group is cis to the $R_1$ hydrogen, and $R_9$ is

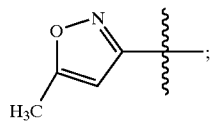;

or $R_2$ is 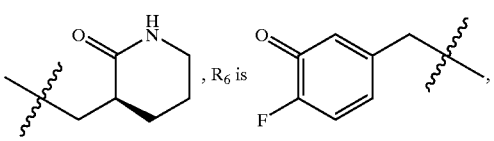, $R_6$ is $R_7$ is $CH(CH_3)_2$, Z is H, $Z_1$ is $CO_2CH_2CH_3$, and $R_9$ is

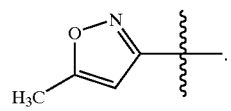.

35. A compound or solvate according to claim 33, wherein $R_2$ is

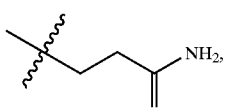 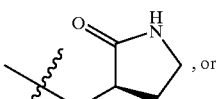, or

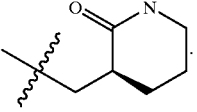.

36. A compound or solvate according to claim 33, wherein:

$R_1$ is H, F, or methyl;

Z and $Z_1$ are each independently selected from H, F, —$CO_2R_{21}$, —CN, and —$C(O)NR_{21}R_{22}$, where $R_{21}$ and $R_{22}$ are each independently H, an alkyl group, a cycloalkyl group, a heterocycloalkyl group, an aryl group, a heteroaryl group, an acyl group, or a thioacyl group, or $R_{21}$ and $R_{22}$, together with the atom(s) to which they are bonded, form a heterocycloalkyl group, provided that Z and $Z_1$ are not both H;

or $Z_1$ and $R_1$, together with the atoms to which they are bonded, form a cycloalkyl or hererocycloalkyl group;

or Z and $Z_1$, together with the atoms to which they are bonded, form a cycloalkyl or heterocycloalkyl group;

$R_2$ is selected from

[structures: -CH2CH2-C(O)NH2; a 2-oxopyrrolidinyl-methyl group; and a 2-oxopiperidinyl-methyl group]

$R_6$ is unsubstituted or substituted phenylmethyl;

$R_7$ is alkyl or aryl; and $R_9$ is 3-isoxazolyl or 5-isoxazolyl unsubstituted or substituted with one or two substituents selected from methyl and halogens.

37. A compound or solvate according to claim 36, wherein $R_7$ is selected from 2-propyl, 2-methyl-2-propyl, 2-methyl-1-propyl, phenylmethyl, and naphthylmethyl.

38. A compound having a formula:

[structure]

wherein:

$R_1$ is H, F, an alkyl group, OH, SH, or an O-alkyl group;

Z and $Z_1$ are each independently H, F, an alkyl group, a cycloalkyl group, a heterocycloalkyl group, an aryl group, a heteroaryl group, —C(O)$R_{21}$, —CO$_2$$R_{21}$, —CN, —C(O)NR$_{21}$R$_{22}$, —C(O)NR$_{21}$OR$_{22}$, —C(S)R$_{21}$, —C(S)NR$_{21}$R$_{22}$, —NO$_2$, —SOR$_{21}$, —SO$_2$R$_{21}$, —SO$_2$NR$_{21}$R$_{22}$, —SO(NR$_{21}$)(OR$_{22}$), —SONR$_{21}$, —SO$_3$R$_{21}$, —PO(OR$_{21}$)$_2$, —PO(R$_{21}$)(R$_{22}$), —PO(NR$_{21}$R$_{22}$)(OR$_{23}$), PO(NR$_{21}$R$_{22}$)(NR$_{23}$R$_{24}$), —C(O)NR$_{21}$NR$_{22}$R$_{23}$, or —C(S)NR$_{21}$NR$_{22}$R$_{23}$, where $R_{21}$, $R_{22}$, $R_{23}$, and $R_{24}$ are each independently H, an alkyl group, a cycloalkyl group, a heterocycloalkyl group, an aryl group, a heteroaryl group, an acyl group, or a thioacyl group, or any two of $R_{21}$, $R_{22}$, $R_{23}$, and $R_{24}$, together with the atom(s) to which they are bonded, form a heterocycloalkyl group, provided that Z and $Z_1$ are not both H;

or $Z_1$ and $R_1$, together with the atoms to which they are bonded, form a cycloalkyl or heterocycloalkyl group;

or Z and $Z_1$, together with the atoms to which they are bonded, form a cycloalkyl or heterocycloalkyl group;

n is 1 or 2;

$R_y$ is H or lower alkyl, $R_6$ is alkyl, cycloalkyl, heterocycloalkyl, aryl, arylalkyl, arylthiomethyl or heteroaryl;

$R_7$ is alkyl, cycloalkyl, heterocycloalkyl, aryl, heteroaryl, —OR$_{17}$, —SR$_{17}$, —NR$_{17}$R$_{18}$, —NR$_{19}$NR$_{17}$R$_{18}$, or —NR$_{17}$OR$_{18}$, where $R_{17}$, $R_{18}$, and $R_{19}$ are each independently H, alkyl, cycloalkyl, heterocycloalkyl, aryl, heteroaryl, or acyl; and $R_9$ is a five-membered heterocycle having one to three heteroatoms selected from O, N, and S, or $R_9$ is

[structures: benzyloxy; and where $R_2$ is a cyclic structure with $A_1, A_2, A_3, A_4$ and $(R_{41})(R_{41})$]

or a solvate thereof.

39. A compound or solvate according to claim 38, wherein:

$R_1$ is H, F, or alkyl;

$R_y$ is H or methyl;

$R_6$ is alkyl, arylalkyl or arylthiomethyl;

$R_7$ is alkyl, cycloalkyl, heterocycloalkyl, aryl, or heteroaryl;

$R_9$ is a five-membered heterocycle having from one to three heteroatoms selected from O, N, and S, where at least one of the heteroatoms is nitrogen, that is unsubstituted or substituted with one or two substituents selected from lower alkyl groups and halogens;

or a solvate thereof.

40. A compound or solvate according to claim 38, wherein:

$R_6$ is arylmethyl or arylthiomethyl;

$R_7$ is an alkyl group;

$R_9$ is 3-isoxazolyl or 5-isoxazolyl unsubstituted or substituted with one or two substituents selected from methyl and halogens; and Z is H and $Z_1$ is —CO$_2$R$_{21}$, —CN, or —C(O)NR$_{21}$R$_{22}$, where $R_{21}$ and $R_{22}$ are each independently H, an alkyl group, a cycloalkyl group, a heterocycloalkyl group, an aryl group, a heteroaryl group, an acyl group, or a thioacyl group, or $R_{21}$ and $R_{22}$ together with the atom(s) to which they are bonded form a heterocycloalkyl group, or Z and $Z_1$ together form a cyclic ester or amide.

41. A compound or solvate according to claim 40, wherein:

$R_1$ is H or F;

$R_6$ is arylmethyl or arylthiomethyl; and $R_7$ is selected from 2-propyl, 2-methyl-2-propyl, 2-methyl-1-propyl, and arylmethyl.

42. A compound or solvate according to claim 41, wherein $R_6$ is phenylmethyl, where the phenyl moiety optionally has one to three substituents selected from halogen, lower alkyl, and lower alkoxy.

43. A compound according to claim 38, selected from the group consisting of

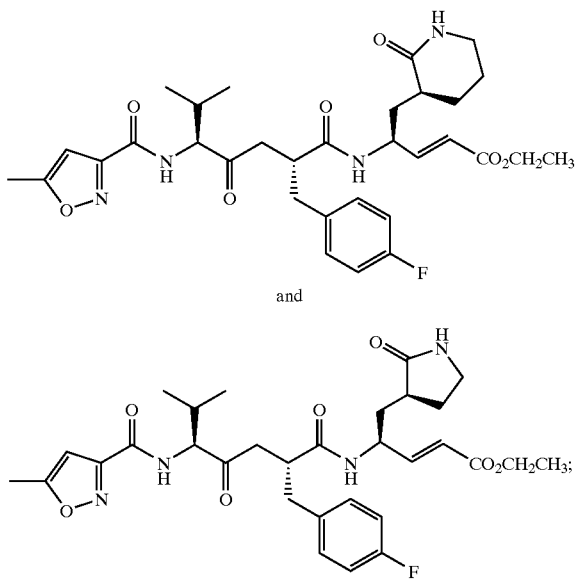

or a solvate thereof.

44. A compound according to claim 38, wherein $R_6$ is arylalkyl or arylthiomethyl and the aryl moiety thereof is substituted with a halogen, alkyl or alkoxy group.

45. A compound according to any one of claim 9, 22 or 36, wherein $R_6$ is substituted phenylmethyl, wherein the phenyl moiety thereof is substituted with a halogen.

46. A method of inhibiting picornavirus replication in a mammal in need thereof comprising administering a compound according to claim 1 to a mammal for a time and under conditions effective to inhibit picornavirus replication.

47. A method of inhibiting picornavirus replication in a mammal comprising administering a compound according to claim 1 to a mammal for a time and under conditions effective to inhibit picornavirus replication, wherein said mammal is infected with a picornavirus.

48. A method of inhibiting a picornaviral 3C protease in a mammal that is infected with a picornavirus comprising administering to said mammal a compound according to claim 1, for a time and under condition effective to inhibit picornaviral 3C protease.

49. A method of inhibiting replication of a picornavirus comprising: contacting a picornavirus with a compound or solvate as defined in claim 1 for a time and under conditions effective to inhibit picornavirus 3C protease.

50. A method as defined in claim 49, wherein the picornaviral 3C protease is a rhinoviral protease.

* * * * *